United States Patent
Hoffer

(10) Patent No.: US 10,984,128 B1
(45) Date of Patent: *Apr. 20, 2021

(54) SPECIALLY ADAPTED SERVING NETWORKS TO AUTOMATICALLY PROVIDE PERSONALIZED RAPID HEALTHCARE SUPPORT BY INTEGRATING BIOMETRIC IDENTIFICATION SECURELY AND WITHOUT RISK OF UNAUTHORIZED DISCLOSURE; METHODS, APPARATUSES, SYSTEMS, AND TANGIBLE MEDIA THEREFOR

(71) Applicant: Steven Miles Hoffer, Mill Valley, CA (US)

(72) Inventor: Steven Miles Hoffer, Mill Valley, CA (US)

( * ) Notice: Subject to any disclaimer, the term of this patent is extended or adjusted under 35 U.S.C. 154(b) by 422 days.

This patent is subject to a terminal disclaimer.

(21) Appl. No.: 15/881,789

(22) Filed: Jan. 28, 2018

Related U.S. Application Data

(63) Continuation of application No. 12/283,099, filed on Sep. 8, 2008, now Pat. No. 9,928,379.

(51) Int. Cl.
*G06F 21/62* (2013.01)
*G06F 16/951* (2019.01)

(52) U.S. Cl.
CPC ........ *G06F 21/6245* (2013.01); *G06F 16/951* (2019.01)

(58) Field of Classification Search
CPC .......................... G06F 21/6245; G06F 16/951
See application file for complete search history.

(56) References Cited

U.S. PATENT DOCUMENTS

| 4,074,006 A | 2/1978 | Boldebuck et al. |
| 5,136,646 A | 8/1992 | Haber |

(Continued)

FOREIGN PATENT DOCUMENTS

FR 2945693 A1 5/2013

OTHER PUBLICATIONS

Schulzrinne, et al, Discovering Location-to-Service Translation (LoST) Servers Using the Dynamic Host Configuration Protocol (DHCP), RFC 5223, [citing RFC 5222], (Network Working Group, Internet Engineering Task Force ( NWG IETF) Aug. 2008) pp. 1-8.

(Continued)

*Primary Examiner* — Dung K Chau

(57) ABSTRACT

These solutions concern transforming a communication network into a scalable network to also automate personalized rapid healthcare support. They integrate biometric identification capabilities into a network entity of, or a resource communicably connectible with, a serving network by using computers to mediate biometric identification and location data. Network operators will provide always on enhanced emergency connectivity for mobility and roaming for user equipment to leverage biometric identification for rapid healthcare support and to produce a unified result set, without risk of undue disclosure of raw biometric data or of selected portions of health profile information. These techniques also support personalized, urgency-supported, healthcare to optimize biometrically-link identifiers/network keys (PUSH TO BLINK), even over a visited operator's IP services. Some facilitate backwardly compatibility across 2G, 3G, 4G, and other networks, whether a mission critical communication, even one with intermodal content via backhaul, is sent via a network that is wireless in any part, or not.

72 Claims, 18 Drawing Sheets

(56) References Cited

U.S. PATENT DOCUMENTS

| | | | |
|---|---|---|---|
| 5,136,647 A | 8/1992 | Haber | |
| 5,721,820 A | 2/1998 | Abali | |
| 5,909,542 A | 6/1999 | Paquette | |
| 6,237,096 B1 | 5/2001 | Bisbee | |
| 7,170,863 B1 | 1/2007 | Denman | |
| 7,181,017 B1* | 2/2007 | Nagel | H04L 9/0825 380/282 |
| 7,194,431 B1 | 3/2007 | Land | |
| 7,287,030 B2 | 10/2007 | Margolus | |
| 7,606,261 B2 | 10/2009 | Salovouri | |
| 7,630,986 B1* | 12/2009 | Herz | G06Q 10/10 |
| 7,751,877 B2* | 7/2010 | Flaherty | A61B 5/0031 600/544 |
| 7,756,633 B2* | 7/2010 | Huang | G06Q 30/0283 701/517 |
| 8,121,068 B2 | 2/2012 | Zhu | |
| 8,144,591 B2 | 3/2012 | Ghai | |
| 8,238,298 B2 | 8/2012 | Zhao | |
| 8,284,756 B2 | 10/2012 | Tay | |
| 8,289,920 B2 | 10/2012 | Wang | |
| 8,295,830 B1 | 10/2012 | Faccin | |
| 8,340,627 B2 | 12/2012 | Edge | |
| 8,457,635 B2 | 6/2013 | Bachmann | |
| 8,521,170 B2 | 8/2013 | Buckley | |
| 8,532,649 B2 | 9/2013 | Carter | |
| 8,543,107 B1 | 9/2013 | Berts | |
| 8,675,630 B2 | 3/2014 | Cherian | |
| 8,695,679 B2 | 4/2014 | Boast et al. | |
| 8,706,122 B2 | 4/2014 | Vikberg | |
| 8,817,741 B2 | 8/2014 | Shaheen | |
| 9,148,769 B2 | 9/2015 | Mahendran | |
| 9,258,179 B2 | 2/2016 | Przybysz | |
| 9,338,710 B2 | 5/2016 | Johansson | |
| 9,521,110 B2 | 12/2016 | Choi | |
| 9,706,378 B2 | 7/2017 | Mahendran | |
| 9,706,557 B2 | 7/2017 | Pantaleo | |
| 2003/0225693 A1* | 12/2003 | Ballard | G06F 21/6245 705/42 |
| 2004/0243567 A1* | 12/2004 | Levy | G06F 21/10 |
| 2007/0106531 A1* | 5/2007 | Deakter | G06Q 10/10 705/2 |
| 2007/0121186 A1 | 5/2007 | Kniveton | |
| 2007/0133435 A1 | 6/2007 | Eneroth | |
| 2007/0232301 A1 | 10/2007 | Kueh | |
| 2007/0258384 A1 | 11/2007 | Sammour | |
| 2007/0294114 A1* | 12/2007 | Urali | G06F 21/6245 705/3 |
| 2008/0002820 A1 | 1/2008 | Shtiegman | |
| 2008/0095114 A1 | 4/2008 | Dutta | |
| 2008/0095362 A1 | 4/2008 | Blom | |
| 2008/0171533 A1 | 7/2008 | Sharp | |
| 2008/0205267 A1 | 8/2008 | El Barachi | |
| 2008/0207206 A1 | 8/2008 | Taniuchi | |
| 2008/0247445 A1 | 10/2008 | Guo | |
| 2008/0306872 A1* | 12/2008 | Felsher | G06Q 20/3674 705/51 |
| 2008/0320149 A1 | 12/2008 | Faccin | |
| 2009/0054029 A1 | 2/2009 | Hogberg | |
| 2009/0070146 A1* | 3/2009 | Haider | G06Q 50/18 705/3 |
| 2009/0106385 A1 | 4/2009 | Sarikaya | |
| 2009/0177942 A1 | 7/2009 | Hannuksela | |
| 2009/0185673 A1 | 7/2009 | Erhart | |
| 2009/0239527 A1 | 9/2009 | Forsten | |
| 2009/0279463 A1 | 11/2009 | Kuliner | |
| 2009/0298456 A1 | 12/2009 | Bakker | |
| 2009/0303904 A1 | 12/2009 | Liu | |
| 2009/0325681 A1 | 12/2009 | Englman | |
| 2010/0054547 A1* | 3/2010 | Tagscherer | G06K 9/6251 382/115 |
| 2010/0111002 A1 | 5/2010 | Xu | |
| 2010/0003954 A1 | 10/2010 | Greene | |
| 2011/0083048 A1 | 4/2011 | Yan | |
| 2011/0151906 A1 | 6/2011 | Kronestedt | |
| 2011/0161504 A1 | 6/2011 | Zhou | |
| 2011/0238822 A1 | 9/2011 | Weniger | |
| 2015/0363586 A1* | 12/2015 | Klevan | G06F 21/32 726/19 |

OTHER PUBLICATIONS

Simon, et al., The EAP-TLS Authentication Protocol, RFC 5216, at Appendix A, updating RFC 2716.(NWG IETF Mar. 2008) pp. 1 and 32.

WEIS, The Use of RSA/SHA-1 Signatures within Encapsulating Security Payload (ESP) and Authentication Header (AH), (NWG IETF Feb. 2008) pp. 1-12.

McCabe, IEEE-SA Marketing Director, "IEEE Approves Standard for Mobile Broadband Wireless Access (MBWA)". News release. IEEE Standards Association. Jun. 12, 2008, accessed from Internet Archive Wayback Machine.

3rd Generation Partnership Project; Technical Specification Group Services and System Aspects; General Packet Radio Service (GPRS) enhancements for Evolved Universal Terrestrial Radio Access Network (E-UTRAN) access (Release *), 3GPP TS 23.401 V8.2.0 (Jun. 2008), at pp. 1, 12-13,15, 19-20, and 131-132. published by 3GPP, 650 Route des Lucioles—Sophia Antipolis Valbonne—France.

* cited by examiner

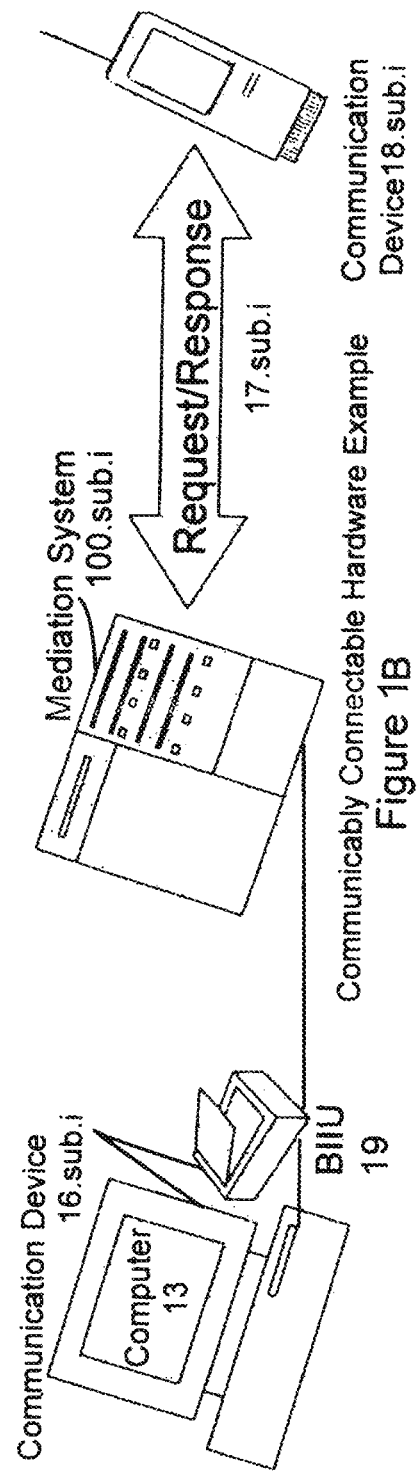

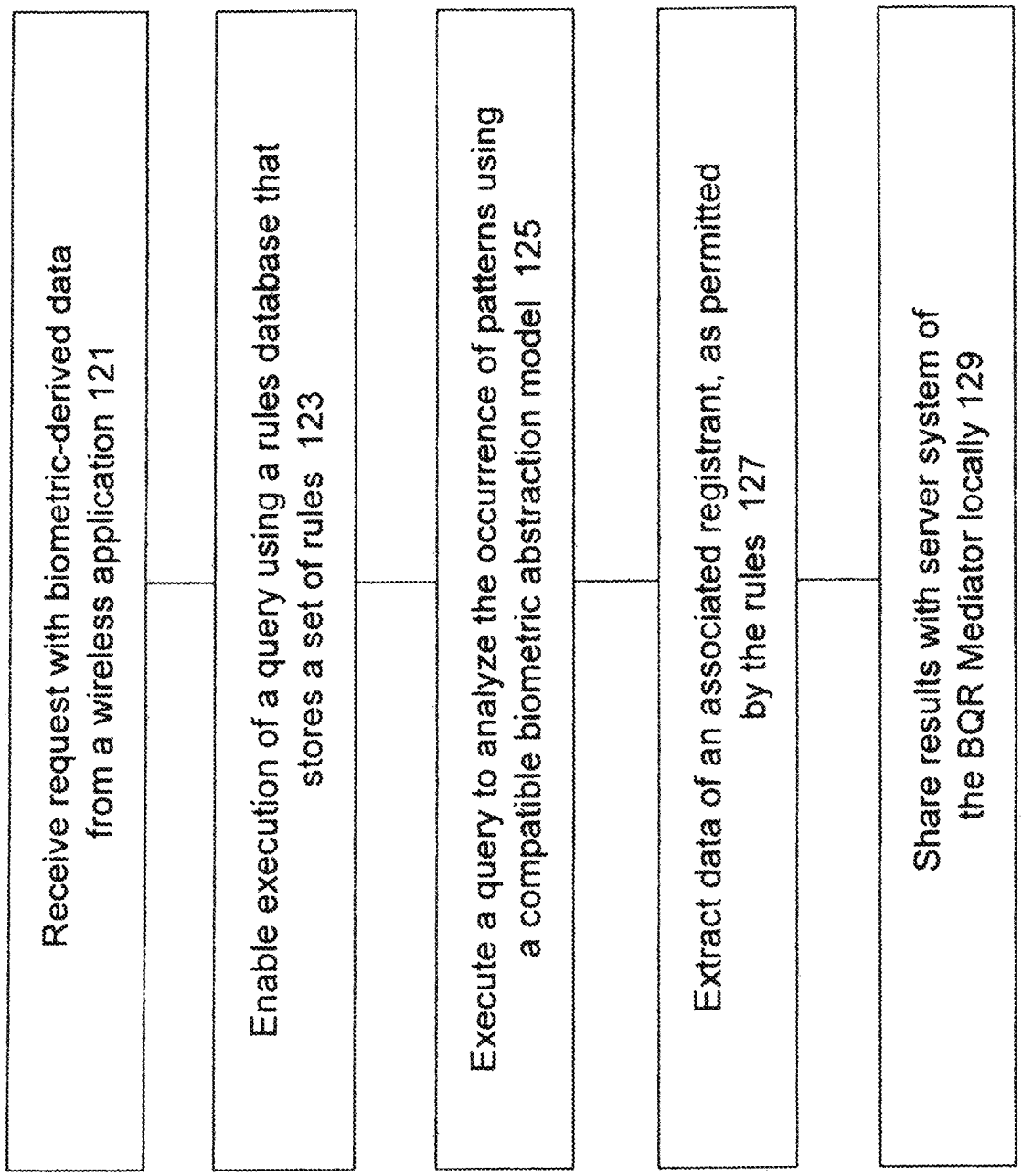

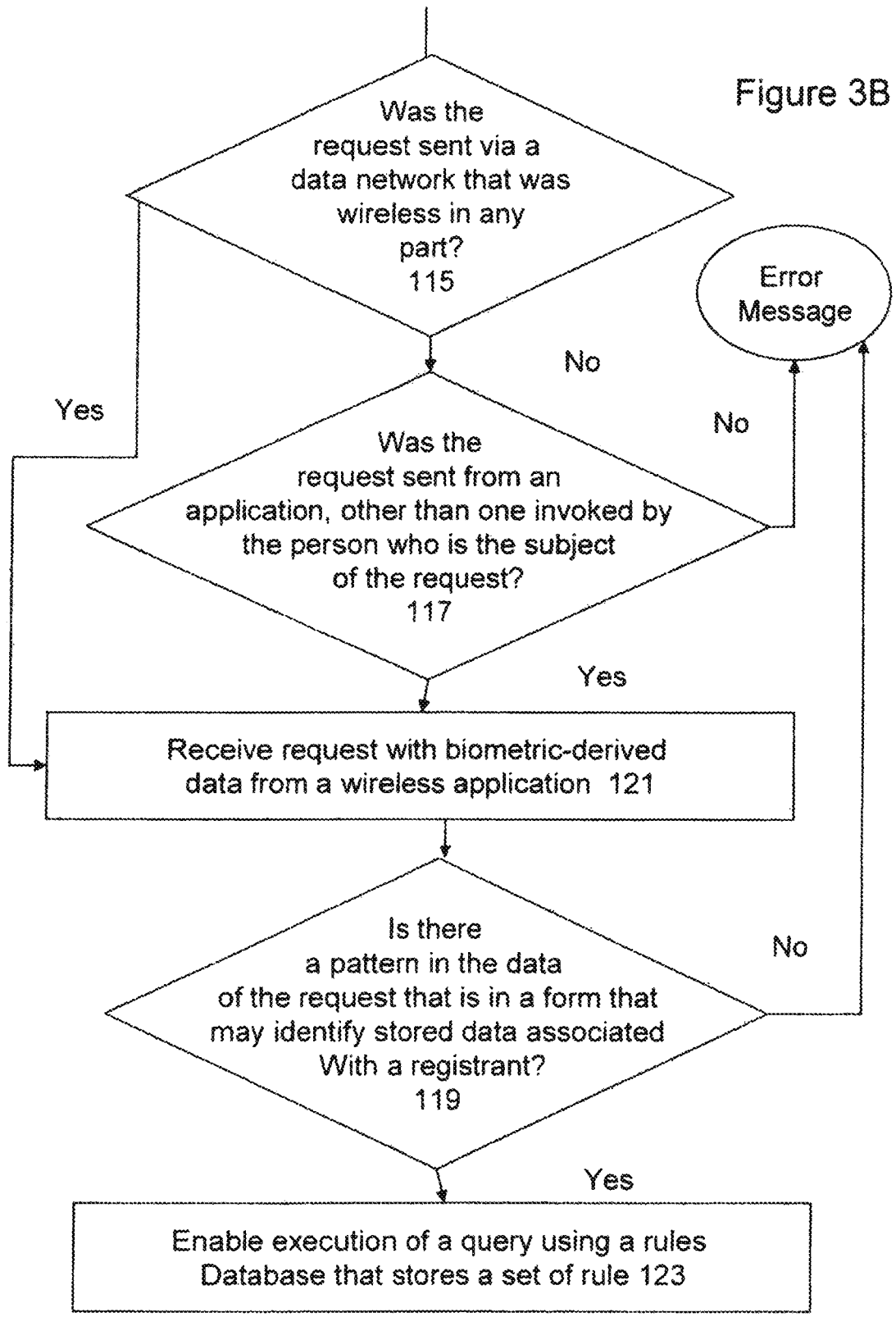

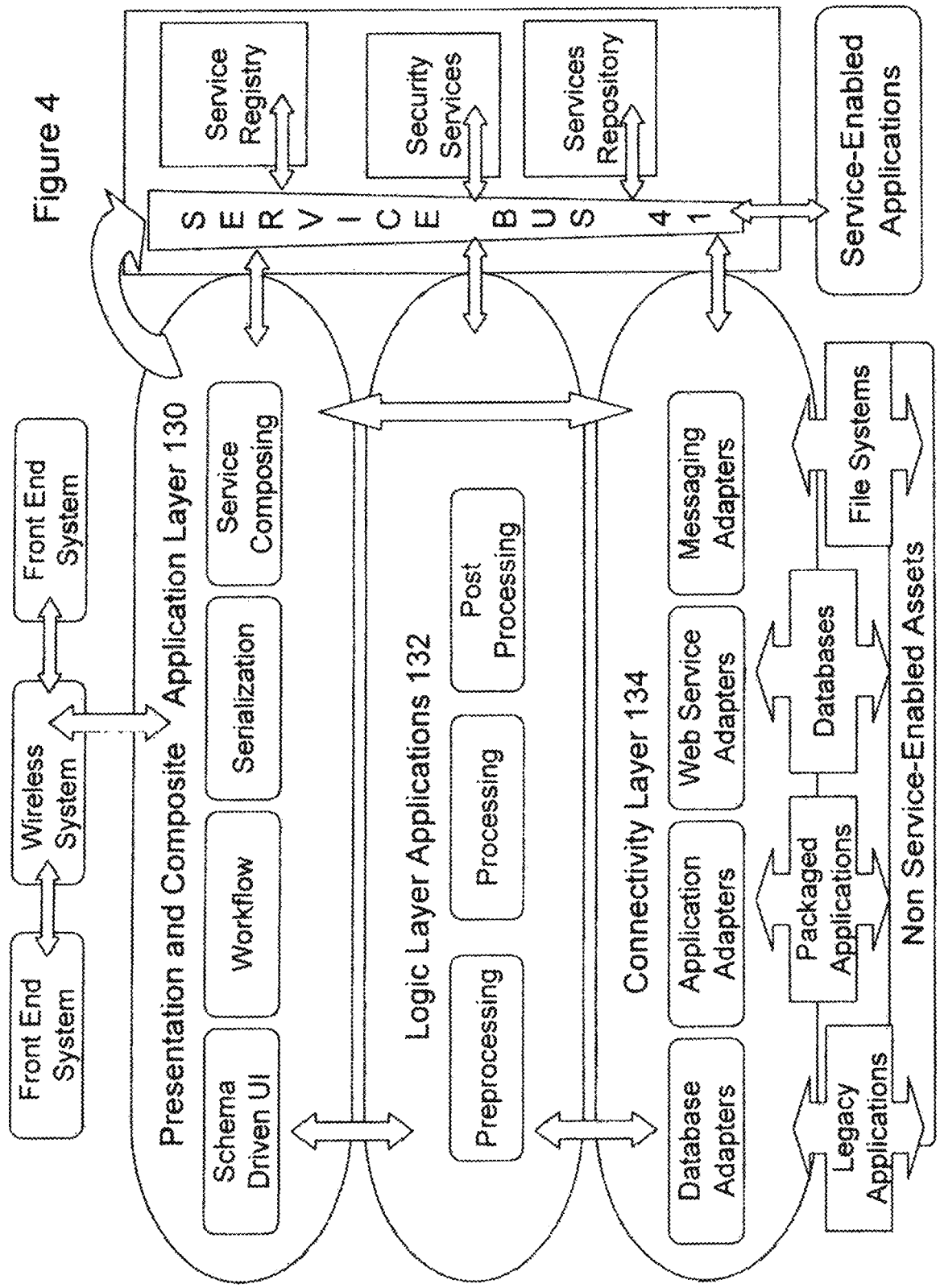

| Mediator Data Structures 101 | Mediator Privacy Procedures 102A | Mediator Security Procedures 102B |
|---|---|---|
| Set Up Rules | Privacy Officer Procedures | Wireless Security Procedures |
| Query Processing Rules | Rule Definition Proc. | Secure Wireless Channel Mgr. |
| Result Processing Rules | Rejected Query Handling Proc. | Rejected Query Handling Proc. |
| Defined Dictionaries | Rejected Result Handling Proc. | Rejected Result Handling Proc. |
| Biometric Abstraction Model Rules | ... | WPA-2 |
| Log Files (one for each UserGroup) | Query Processing Proc. | Query Processing Proc. |
| ... | Result Processing Proc. | Result Processing Proc. |
| | Database Access Proc. | 802.11i Access Proc. |
| | Log File Writing Proc. | RADIUS Proc. AES |
| | ... | Mobility Network |
| Figure 6A | Figure 6B | Figure 6C |

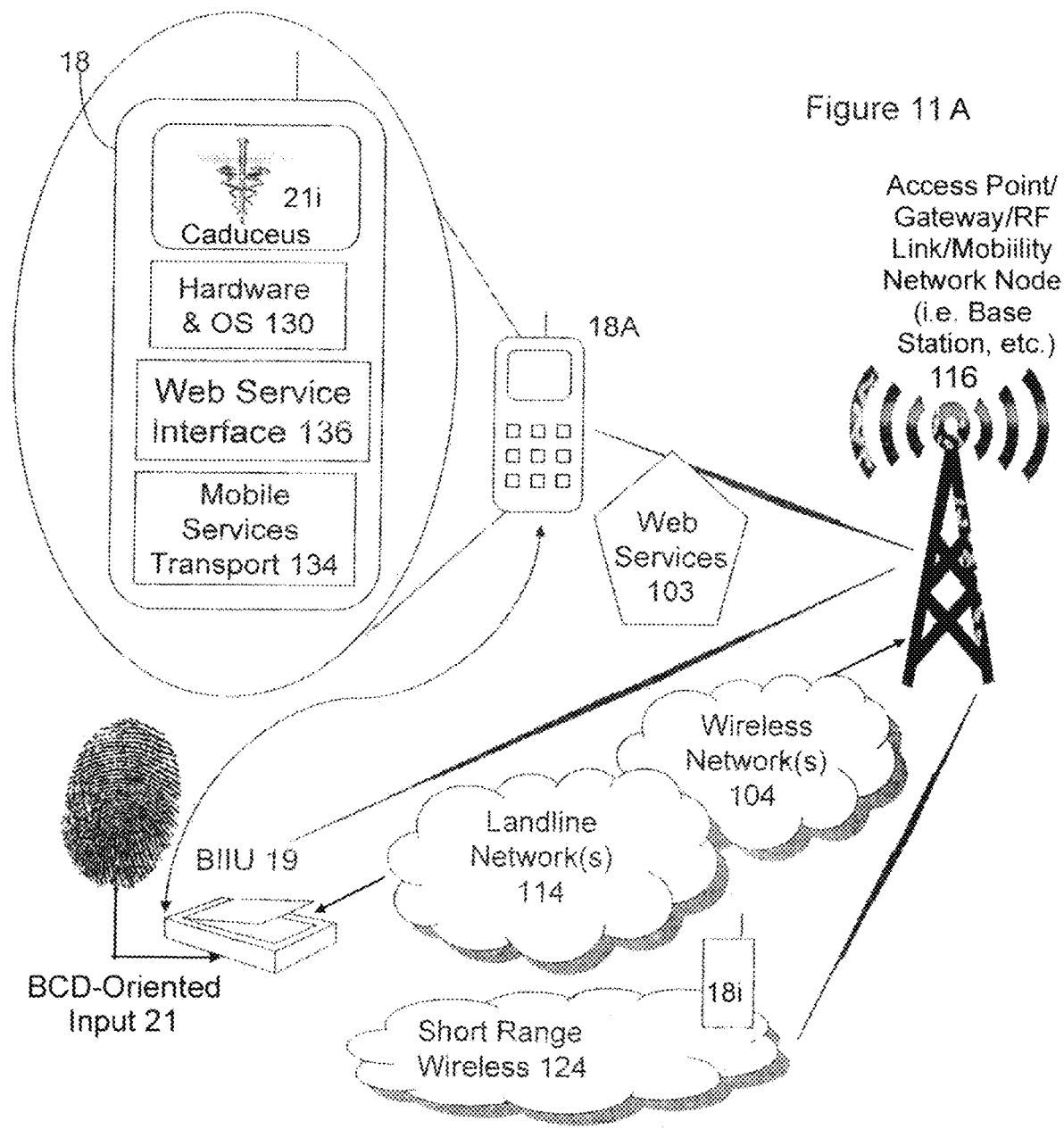

SPECIALLY ADAPTED SERVING NETWORKS TO AUTOMATICALLY PROVIDE PERSONALIZED RAPID HEALTHCARE SUPPORT BY INTEGRATING BIOMETRIC IDENTIFICATION SECURELY AND WITHOUT RISK OF UNAUTHORIZED DISCLOSURE; METHODS, APPARATUSES, SYSTEMS, AND TANGIBLE MEDIA THEREFOR

CROSS-REFERENCE TO RELATED APPLICATIONS

This is a continuation of application Ser. No. 12/283,099 filed, with title "Methods using mediation software for rapid health care support over a secured wireless network; methods of composition; and computer program products therefor" and naming as inventor Steven M. Hoffer, granted as U.S. Pat. No. 9,928,379, the entire content of which is hereby incorporated herein by reference in its entirety.

BACKGROUND OF THE INVENTION

Field of Invention

The present invention relates to an integration of capabilities associated with certain specialized software for mediation, biometric abstraction processes, and wireless communications to produce a unified result set.

The invented methods use mediation software to produce a unified result set ("result set" or "result") by utilizing a registrant's transformed biometric data to advance query resolution, upon remote request from an application, other than one operated by the registrant, which privately seeks the registrant's personal data. Mediation integrates a number of layers of computer and network technology to transform and find data by applying knowledge about resources, search strategies, or requirements for usage. By using data communications over one or more networks that at least partly include a wireless network, a method of mediation enables a qualified requester, described hereafter as an Emergency Medical Responder or Requester ("EMR"), to request to (a) identify otherwise unidentifiable persons, or (b) verify the identity of persons to find personal information. Processing a query may be conducted for identification or verification as separate operations, as needed, or may be performed by messaging that consolidates into one operation the processes for identification and verification. In all events, such query processing may be referred to as resolution. Security may include, without limitation, secure end-to-end transmission of personal data, even over wireless facilities, under conventional practices or standards. Results or outputs may refer to personal information or data that may comprise either "profiles" that summarize registrant data, personal health records (PHRs), "in case of emergency" data, advanced directives, digital signatures, other content, or data used to retrieve information specific to a registrant. Preferably, each registrant may modify privacy rules and audit each request, access, and resolution to confirm adherence to privacy rules, as needed.

Description of Related Art

1. Biometric Character Data ("BCD")

There are many different conventional biometric-based solutions. Some are based on matching, at the point of transaction, the information obtained by the scan of a "live" biometric sample to a pre-stored, static "match template" created when the registrant originally registered data or stored files. Some of these processes or systems simply store raw biometric sample files. This poses privacy risks associated with storage or access of both the biometric data and the content files. Others refrain from using the raw biometric samples, but rely upon some transformation or abstraction of the raw biometric data instead. Those that employ approaches that prevent reconstruction of raw biometric data are generally preferable to those that do not do so. For example, some biometric solution providers use biometric data to generate data that helps descramble an encrypted code to produce a key, often in the form of an alphanumeric string. Still other biometric solutions often use other approaches to abstract raw biometric data irreversibly, especially to advance more stringent security or privacy goals.

Physical features, such as thumbprints, fingerprints, iris, retina, hand configuration, vascular patterns, genetic or genomic data like DNA or RNA (i.e. profiling, markers, samples, etc.) or behavioral features, such as signature, voice, gait, or keystroke, must fulfill a certain criteria to qualify for use in biometric-aided identification. They must be unique, universal, acceptable, collectable, and convenient to the person, in addition, to demonstrating reliability for identification, resolution, or anti-circumvention. However, most commonly, permanence is a key feature for biometrics. The biometric character data (hereinafter generally "BCD") typically must retain all the above features, and in particular the uniqueness, either unchanged or acceptably changed, over the lifetime of the individual.

By reusing existing technologies in new combinations, generic content delivery enablers or intermediaries should be capable of delivering content of any kind, where only the service or content metadata is used directly by enabling entities, so that delivered content, until reaching an intended recipient, may remain undisclosed, encrypted, or opaquely packaged, through the operator of the database or enabler. Computer server systems deployed to deliver content may limit access by requiring a key. The BCD may be used as a link to a key, a Unique Patient Identifier (UPI) or translated into a unique uniform identifier (UUID) code, an alphanumeric string ("string"), or a similar code, (collectively hereafter "registrant-specific identifier" or RSI). RSIs may be comprised of digital or binary data. The key or other indicator may signify either an access right or non-repudiation of the request by, or on behalf of, a registrant, or both. To reduce risks that personalized identifiers may be copied, spoofed, impersonated, compromised, or pirated by unauthorized parties, many have introduced cancelable biometric or other abstraction techniques to blend the attributes of biometrics with the cancellation and replacement properties of often less robust passwords or PIN numbers. Some related, but often distinguished, configurations, may use biometric encryption (BE) techniques. See, e.g., A. G. J. Teoh and T. S. Ong, Secure Biometric Template Protection via Randomized Dynamic Quantization Transformation, Biometric and Security Technologies, April, 2008, ISBAST ("BE has been reported by several groups of researchers with different names such as private template, BioCrypt, fuzzy commitment, fuzzy vault, BioHashing, and helper data." (citations omitted)). [Teoh & Ong Article]

BE techniques, cancellation biometric (CB), and many newer abstraction techniques, often replace vulnerable passcodes like passwords subject to dictionary attacks, without storing biometric samples. These biometric techniques commonly rely upon biometric abstraction models, but also usually entail an enrollment phase and a verification phase.

See, e.g., C. Soutar, D. Roberge, A. Stoianov, R. Gilroy, and B. V. K. Vijaya Kumar, Biometric Encryption™, ICSA Guide to Cryptography, at Chapter 22 (McGraw-Hill 1999). BE typically entails enrolling a person using biometric data to generate an identification code and a personal biometric encryption template that can be used with a live biometric sample to reproduce the identification code, even though tools for precisely replicating BCD, like fingerprints, etc., are inexact. The verifying data captured from a finger pattern or other BCD, however, may be used with increasing reliability to unscramble an alphanumeric string to release a key.

Focusing on fingerprints momentarily, for some illumination by an example, the key, or BCD-deciphered string, is irreversible to detect without the finger pattern. Since the key is decoded by a finger pattern, the unscrambling template does not have to be encrypted or kept secret in order that the key is kept secure. The key can only be descrambled by placing the correct live finger pattern with the template, such as by using the biometric sensor, like one communicably connected to a medium, database, or repository, with access to the scrambled data. The operation of successfully descrambling releases the key, typically a string of alphanumerics. The key can thereafter be used so as to verify a person's identity (i.e., upon producing a string, reproducing a private key, resolving a query with data of a key, allowing access, or generating a result set, etc.), or so as to access personal data, whether in an encrypted form or not. Hereafter "biometric" and "BCD" shall be used to encompass, without limitation, cancelable biometric (CB) techniques, or biometric encryption (BE) technologies, or one or more other biometric abstraction models as needed. BCD measurements often use statistical, averaging, or other image analyses techniques to produce accurate associations and reliable matching results.

2. Most Common Biometric Applications are Based Upon an Identity of Interest in Both Personal Control and Access to Protect Privacy Rights Most transactional applications of biometrics have been designed for personal use only. These methods, that protect some privacy interests, have envisioned an individual actively controlling the submission of his BCD to a database with a "match template" to ensure his proper identity, or verify it, to allow him to authorize a transaction or complete another operation (i.e. entry, access, upload, download, execute, request, response, etc.). Data storage may be configured using one or more information storage units, databases, registries, repositories, and archives, network channels, as well as other techniques (hereafter collectively "databases").

Some mobile phones and laptops were equipped with sensor plates for fingerprint extract and transmission to remote databases by the late 1990s. Similar devices continue today to support Near Field Communications and often to leverage a person's control over his BCD in electronic payment transactions. In these contexts, there is almost always an "identity of interest" between the individual who seeks to submit or use his "live" BCD, and the same individual who thereby seeks to gain access or authorization upon matching the live data extracted with a stored template.

More generally, BCD processing or matching, typically by an unattended or attended server computer system, may advance either identification (one of many, 1:N) or verification (one of one, 1:1) (hereinafter collectively "query resolution" or just "resolution"). Resolution, as used herein, may accordingly encompass identification or verification, or both, usually through data processing, transmission, or mediation. Often such resolution techniques are applied to support methods that associate, find, match, access, or retrieve an individual's data. Sometimes they are applied to transfer data subject to encryption, for instance, using cryptographic keys. Many rely upon public key, symmetric key, asymmetric key, or other secure management processing of, or retrieval of, confidential data, private content, PINs, or crytpokeys, etc.

a. Government Security Applications as a Broad Exception

Other applications that depart from the paradigm of self-controlled use of ones own BCD, based upon the "identity of interest" premise, have recently evolved rapidly for government security, customs, or border control. These spin-off applications have expanded mainly in the sphere of certain security measures. The U.S. and other governments have deployed biometric applications to ensure security from airports to immigration, criminal matters to terrorist exclusion, in a manner where agencies demand or require an individual to relinquish control over the use of their own BCD, particularly for limited purposes or contexts.

b. Employers' Reliance on Biometrics for Security is Another Growing Exception

Another exception to the private individual control rule has expanded in private employer-employee relations. Until the U.S. instituted its US VISIT program, the Walt Disney Company was reputed to operate one of the largest and most pervasive systems to secure access to its facilities solely to its employees, who had relinquished control to their employer. Conventional biometric applications intrinsically teach away from reliance upon others, aside from exceptional ones sponsored by public agencies and employers. Other third-party applications have been sharply criticized for overreaching and breaching privacy rights.

In the health field, the sharing of simple personal, but non-biometric, information has typically required prior clearance by an express waiver from a patient, with few variances. In the wake of laws like the Health Insurance Portability and Accountability Act (HIPAA), biometric applications that share data without securing a waiver from a person are often unpopular, unduly risky, or sharply criticized, if not unlawful. Still others have witnessed the upward spiral of victims of medical identity theft. This often includes impersonations to attain insurance by ones not insured, where culprits have attained medical services unlawfully, or, for instance, fraudulently, by using the private personal health information of others improperly. The FTC's 2006 Identity Theft Survey Report indicates the number of incidents reached nearly 250,000 in 2005. When hospitals use biometrics of patients who are provided health care under an agreement with the hospital, the hospital often acts as a proxy for the biometrically registered patient so as to extend the basic "identity of interest" paradigm to approve certain known and trusted medical service providers, acting on the behalf of the patient with the latter's consent.

3. Conventional Identification Methods Using Emergency Health Cards

Without elaborate technical requirements, the Red Cross offers guidance for creating an emergency health card. To customize a card, it suggests "[a]n emergency health information card communicates to rescuers what they need to know about you if they find you unconscious or incoherent, or, if they need to quickly help evacuate you. An emergency health information card should contain information about medications, equipment you use, allergies and sensitivities, communications difficulties you may have, preferred treatment and treatment-medical providers, and important contact people." It suggests that people make multiple copies of the card and place them in places including behind the drivers license or primary identification card. On the front of the card, the Red Cross' suggestion adds, put items like name, street address, city, state, zip, phone (home, work), fax no., birthdate, blood type, social security number, health insurance carrier and individual and group number, physicians contact info, and on the back note your emergency contacts, conditions, disability, medication, assistance needed, allergies, and immunization dates. This kind of card stores a set of data often dubbed "In Case of Emergency" data ("ICE data").

a. Universal MRA™

Similarly, some private, tax-exempt, or non-profit organizations, like Yellow Courtyard, offer expanded systems like Universal MRA™ (Medical Records Access). The latter deploys a "secure database (within multiple physical locations) allowing for universal access of medical records to both Explorers [members] and their authorized health care providers. With the Explorer's discretionary consent, any medical/healthcare practitioners within the Yellow Courtyard Network, or outside, will be able to review these records, allowing for true continuity of care and efficiency of collaborations. Explorers will be given a wallet-sized ID card, with access instructions for emergency medical providers offering restricted access to relevant medical information should the Explorers be unable to communicate in case of accident or disaster."

This kind of system also stores "ICE data", like that suggested by the Red Cross, but, like others of its ilk, presupposes that a member can invariably retain and present his or her card. Sometimes, as during trauma or mass casualties, however, a member may be unable to do so.

b. "Mobile Phone ICE"

Several variations on this approach have emerged with renewed energy since a British paramedic, Bob Brotchie, began promoting one program called "In Case of Emergency", or ICE, in May, 2005. ICE encourages people to enter emergency contacts in their cell phone address book under the name "ICE." Brotchie, when interview on Jul. 12, 2005, explained:

"I was reflecting on some difficult calls I've attended, where people were unable to speak to me through injury or illness and we were unable to find out who they were. I discovered that many people, obviously, carry mobile phones and we were using them to discover who they were. It occurred to me that if we had a uniform approach to searching inside a mobile phone for an emergency contact then that would make it easier for everyone." BBC Radio 4 Today Programme, The idea of ICE is that everyone should put an emergency contact name and number into their mobile phone under the headword "ICE." It expanded with the distribution of a "sticker" applied to convey an alert to EMRs. Still others have issued other tangible cards in an attempt to consolidate material health data or records that had not been centralized or normalized across formats for rapid access.

c. PersonalMD Emergency Cards

Cerner, for instance, is a company that sponsors a fee-based service called PersonalMD. PersonalMD promises to "enable you to manage all your medical and health records in one convenient, secure site." Moreover, Cerner's FirstNet offering reportedly leverages an "Electronic Medical Record" that attempts to integrate multiple records (i.e. from doctors, hospitals, laboratories, radiology, and pharmacy, etc.) into a single data repository to reduce the risk of medical errors. Cerner's suite of offerings provides clinicians with one source for obtaining vital patient information, such as allergies, medication administration records, and past medical history. In addition, it asserts that embedded data from "our network of partners help support the clinical decision making process." Its PersonalMD Emergency Card, it claims, "serves as the vital link between our online record and medical professionals around the world. Your card includes your name and how to gain access to specifically marked 'emergency information'" when you are unable to do so yourself 4. "Unique Patient Identifiers" (UPI), Smart Cards, and Implantable Chips Several organizations have sought to develop an array of new systems or stop-gap measures after the events of Sep. 11, 2001 when New York firemen were writing their badge ID numbers on their chests in case they were found injured or unconscious. As in New York, FEMA and other rescuers in New Orleans were also at a loss to help identify scores of victims during Hurricane Katrina relief efforts. FEMA had insufficient safeguards in place to identify the wounded, unconscious, or disoriented. FEMA could not identify individuals' emergency health data in a timely manner to minimize the human suffering, even if DoD workers did attend to 700 victims within the first 24 hours. It was evident again, that emergencies do not always neatly leave victims with their voices, faculties, ID cards, wallets, HMO cards, cell phones, or drivers' license in tact to allow prompt identification. Moreover, over 25 million Americans do not even carry ID. Accordingly, there remains a critical need for better, faster personal identification and access to each individual victim's personal health information in urgent care or emergency situations.

Many of the next generation services were based upon such devices for those like security guards, without such risks of acute prior conditions, but who mainly consider themselves at risk of some accident or injury. These offered a bit of transient hope for them too on the job, but were suboptimal in practice since they required one or more layers of unnecessary hardware, software, easily lost cards, or managed services lacking in privacy or dependability.

In the private sector, some commercial services were introduced to save mainly high-risk subscribers' lives though personal identification devices, or tangible accoutrements, like ones for carrying an identification card with embedded tags, wearing medical bracelets with either GSM location capabilities or alert monitors for vital data, attaching alert systems to wallets or mobile phones, or using an implantable microchip, that providers claimed could make a difference and reduce the risk of protracted and dangerous personal identification lags. Some distress alert mechanisms have shown benefits in limited recent trials for diabetics patients. Beyond these trials, others too have promoted implantables, especially when no better alternatives existed. Many others, however, decline to use anything so invasive or tangible.

One private solution provider aptly quotes an emergency medicine physician who described the hurdles that are not uncommon "Trying to identify unidentified patients is torture—you go through pockets, computer records, and make phone calls. It can take well over an hour. A good medical history would really expedite care."

Joseph Feldman, M D, Chairman, Emergency Medicine, Hackensack University Medical Center Paramedics in metropolitan areas like Santa Monica, Calif., often estimate that this persistent, and sometimes severe, problem arises in nearly one-eighth of their emergency responses daily, and even without any mass casualties.

5. Biometric Abstraction Approaches and Privacy Optimization Techniques

Several biometric abstraction models are more promising because they irreversibly decouple the raw biometric data sets from their powerful properties that advance individual recognition. Some biometric-based solutions that may be used as building blocks across many health and non-health applications alike. Some may rely upon BCD transformations, such as biometric cancellation solutions, or biometric encryption approaches, or other programs (See e.g., remarks by Dr. George J Tomko, September 1996). Some solutions to safeguard sensitive information use either key management techniques, BCD-alphanumeric string translations, or dynamically selected algorithms, bioscripts, fuzzy vault technology, image abstraction, data transformation, or other biometrics-aided techniques. Many developers of these biometric recognition advances underscore that the storage of a "biometric template" poses far higher security risks than storing of "biometric encryption templates", for instance, that cannot expose raw biometric images or samples. The former can become vulnerable to exposing raw biometric images or samples, especially when centrally stored.

6. Biometric Encryption (BE)

In recent Congressional testimony, Peter Swire, a former leading GAO privacy official and professor, observed that progress has been made since Dr. Tomko's earlier work on biometric encryption (BE), and Professor Swire explained:

"Fortunately, slightly more sophisticated biometric technology can greatly reduce these identity theft and other privacy risks. Ann Cavoukian, the Privacy Commissioner for Ontario, has been a global leader in promoting what is called "biometric encryption." With biometrics expert Alex Stoianov, she has published: "Biometric Encryption: A Positive-Sum Technology that Achieves Strong Authentication, Security AND Privacy." [(March 2007)["Cavoukian Paper"]] As explained by a prominent biometrics researcher:

'In Biometric Encryption, you can use the biometric to encrypt a PIN, a password, or an alphanumeric string, for numerous applications-to gain access to computers, bank machines, to enter buildings, etc. The PINS can be 100s of digits in length; the length doesn't matter because you don't need to remember it. And most importantly, all one has to store in a database is the biometrically encrypted PIN or password, not the biometric template.'[Id. at 16 (quoting Dr. George Tomko).]

The privacy and security advantages of this approach are large. The system owner, such as an employer, gains the advantages of traditional biometrics approaches, such as being confident that only the correct person can gain access. For the individual, there is the large privacy advantage that a breach by the system owner will not compromise the fingerprint or other biometric. Only that one PIN is lost, and the individual can generate a new PIN/password using the same fingerprint or other biometric. In the long run, systems owners also benefit, because this approach is much less likely to be based on a compromised fingerprint than under the current, flawed approach.

After careful review of the technical and policy literature, Cavoukian and Stoianov highlighted six advantages of the biometric encryption approach:
NO retention of the biometric image or template
Multiple/cancelable/revocable identifiers
Improved authentication security: stronger binding of user biometric and identifier
Improved security of personal data and communications
Greater public confidence, acceptance, and use; greater compliance with privacy laws
Suitable for large-scale applications In terms of legislative action, this Committee should support a careful federal examination of this promising approach, which appears likely to be better from both a privacy and a security perspective."

Some approaches under the rubric of Biometric Encryption, it is worth digressing, have been developed to extend certain authentication processes, including Public Key Encryption or other security conventions. For database access, conventional systems often issue authentication assertions. Some developers of computing domains avoided complexities introduced by the advent of mobility networks by basing a requester's eligibility for authentication on conventional techniques, while relying on access for data communications solely over landline networks (i.e. these techniques may include two-stage authentication, public key management, pretty good privacy (PGP), OpenPGP, GnuPG, public key infrastructure (PKI), etc.). PKI, for instance, unlike public key encryption between two parties, typically relies upon a trusted third party (TTP) (i.e. such as a certificate authority (CA), trusted authority, etc.). The TTP has the ability to match a registrant's identity from either a PIN or another registrant-specific identifier from transformed biometric data, or some abstraction thereof, or associated metadata with that stored by a registration authority (RA), and to issue an identity certificate. These other deployments may include ones that apply biometric encryption (BE), as discussed below, so as to enable a requester acting to retrieve a registrant's private data, by descrambling a registrant's PIN accessible at runtime, on the fly, or remotely as needed, through PKI or various other configurations.

Yet, a closer look at the Cavoukian and Stoianov study further illuminates a generalized context for achieving these advantages in various scenarios including ones described in the first two exemplary case studies, as follows:

The Cavoukian Paper illustrates a basic application as follows:

"Case Study #1: Small-scale use of Biometric Encryption

To demonstrate the power of BE, we will briefly present a biometric authentication protocol (remote or local) with third party certification. We use a simplified and reworded description from Boyen's paper on Fuzzy Extractors.[1] Suppose that Alice wishes to authenticate herself to Bob using biometrics. Due to privacy concerns, she does not wish to reveal any biometric information to Bob. Conversely, for the authentication to be meaningful, Bob wants some assurance that Alice is in fact in possession of her purported biometrics at the time the authentication is taking place (i.e., that no one is impersonating her). We assume that there is a third party (often called the Trusted Authority), Trent, whom Bob trusts to honestly certify Alice's biometrics, and to whom Alice will temporarily grant access to her biometrics for the purpose of generating such a certificate. Alice will want to be able to obtain as many or as few of those certificates as she wants, and to reuse as many of them with multiple Bobs, some of whom may be even dishonest, without fear of privacy leaks or risk of impersonation. The protocol is as follows:

[1] X. Boyen, "Reusable cryptographic fuzzy extractors," CCS 2004, pp. 82-91, ACM Press. (revised footnote number supplied); also on file with the Stanford Artificial Intelligence Lab. (footnote original).

Enrollment and certification: Under Trent's supervision, and using Alice's own biometric:

1. Alice creates a Biometric Encryption template from her biometric and a randomly selected PIN. Neither the biometric nor the PIN can be recovered from the template;
2. The PIN is used to generate a pair of keys called public and private keys;
3. The biometric, the PIN, and the private key are discarded;
4. If Trent is satisfied that Alice has executed the steps honestly, he certifies the binding between Alice's name and the public key, i.e., he digitally signs the pair ["Alice," public key]. At this point, Alice may send the public key to Bob, or even publish it for all to see.

Verification: A challenge/response scheme is used to verify Alice:

1. At any time when appropriate (e.g. whenever Alice desires to authenticate herself to Bob), Bob sends Alice a fresh random challenge;
2. By obtaining her new biometric sample and applying it to her Biometric Encryption template, Alice recovers on-the-fly her PIN, which, in turn, regenerates her private key;
3. Alice signs the challenge with her private key and gives Bob the signature;
4. Bob authenticates Alice by checking the validity of the signature under her authentic public key.

The protocol does not require Alice to remember or store her PIN or her private key. The Biometric Encryption template may be stored on a smart card or in Alice's laptop that also has a biometric sensor. . . . The system based on digital signatures may be adopted both for a remote and local access. The important point is that the most critical part of any cryptosystem, the PIN (or a password), is securely bound to the biometrics. . . . . Neither Alice's biometric nor her PIN are stored or revealed. As a result, the system is both secure and highly privacy protective.[2]

[2] See also, Y. Wang, J. Hu, K. Xi and B. V. K. Vijaya Kumar, "Investigating correlation-based fingerprint authentication schemes for mobile devices using J2ME technology." IEEE Workshop on Automatic Identification Advanced Technologies, AutoID 2007, Alghero, Italy 7-8 June; and F. Jan, J. Hu, L. He and Y Wang, "Generation of reliable PINS from fingerprints. Security Symposium," IEEE International Conference on Communications (ICC), Glasgow, Scotland, June, 2007. (footnote original).

The Cavoukian Paper illustrates another salient example involving medical records, more specifically, as follows:

Case Study #2: Anonymous database; large or medium-scale applications

Suppose that a clinic, a hospital, or a network of hospitals maintains a database of medical records. Alice does not want her record to be accessed by unauthorized personnel or third parties, even for statistical purposes. For that the latter, her record is made anonymous and encrypted (by conventional means). The only public entry in the database is her personal identifier, which may be her real name or, in certain cases (e.g. drug addiction clinic), an alias ("Jane Doe"). The link between Alice's identifier and her medical record is controlled by Biometric Encryption: On enrolment, a BE template is created from Alice's biometric and a randomly generated PIN (Alice does not even know the PIN). The PIN is used to generate a pointer to Alice's medical record and a crypto-key that encrypts the record, and also a pair of keys called public and private keys (similar to case study 1). The BE template and the public key are associated with Alice's ID and stored in the database (they can be also stored on Alice's smart card); other temporary data, such as Alice's biometric, the PIN, the private key, the pointer, and the crypto-key, are discarded.

Suppose that Alice visits a doctor, to whom she wants to grant remote access to her medical record, or part of it, if the record is structured. From the doctor's office, Alice makes a request to the database administrator, Bob. The authentication procedure using challenge/response scheme is similar to that in case study 1:

1. If Alice does not have her smart card with her (e.g. in the case of an emergency), Bob sends Alice's BE template to the doctor's office;
2. Alice applies her new biometric sample to the BE template and recovers on-the-fly her PIN;
3. The PIN is used to regenerate her private key, the pointer to her medical record, and the crypto-key;
4. Bob sends Alice a fresh random challenge;
5. Alice signs the challenge with her private key and gives Bob the signature;
6. Bob authenticates Alice by checking the validity of the signature under her public key;
7. Alice securely sends Bob the pointer to her medical record;
8. Bob recovers Alice's encrypted medical record (or a part of it, also encrypted) and sends it to Alice;
9. Using her crypto-key, which was regenerated from her PIN, Alice decrypts her medical record for the doctor;
10. Alice's biometric, the PIN, the private key, the pointer, and the crypto-key, are discarded.

In summary, Bob (the database administrator) has an assurance that Alice is, in fact, who she claims to be (she was able to unlock her BE template in the doctor's office); he is also assured that her medical record was sent to the right person. On the other hand, Alice retains full control over her medical record, so that even Bob (the database administrator) has no access to it, since he does not have the crypto-key to decrypt it. *The privacy protection is embedded into the system at a very basic technological level.* Id. at. pp. 26-30.

While the case studies illustrate how biometric encryption and public key management can be complementary, and mutually reinforcing, when Alice is present before her doctor, it does not adequately suggest or describe how the method may be automated so that a method using software can enable a server system to operate to advance urgent or emergency medical assistance for her any place at any time, when Alice is unidentifiable, as when she is unconscious, incoherent, or disoriented without her wallet. Specifically, an EMR may seek the support of a service or method using software and abstracted biometric data to identify her and attain her profile, but will not find any available, much less ones used as a method of first resort. When someone like an EMR, other than Alice or her primary doctor at her local hospital, is seeking her private and protected content on her behalf securely, they should be able to invoke a method using software to enable requesting it and to resolve Alice's access so as to generate certain data of her profile within authorized privileges, subject to audit under the principle of least privilege, discussed below. As Peter Swire has also noted, the solution for limited access should also be provisioned so that "[a]ccess to biometric databases should thus be subject to effective audit systems."

In other words, many of the safeguards or precepts of biometric encryption are necessary but not sufficient and must be complemented with processes or provisions for mediation on behalf of registrants who need EMR support, but are unidentifiable at the crucial time when timely health care is a matter of the greatest gravity. New methods are needed to enable EMRs to indirectly use a stronger and more secure binding of Alice's user biometric and identifier, particularly via data communications over wireless facilities or mobility networks. In 1996, NTIA published a report underscoring that the use of radio spectrum for public safety requires vast improvement, and observed that: "Emergency medical providers desire the ability to transmit images and other vital statistics about the injured from the paramedic unit back to trauma centers or hospitals to aid in diagnosis and pre-arrival treatment." Final Report of the Public Safety Wireless Advisory Committee to F.C.C. Chairman Reed E Hundt and NTIA (Sep. 11, 1996) at p. 15. Such health support information technologies must be carefully extended to anticipate the unidentifiable person in distress by galvanizing techniques of biometric transformation, wireless security, encryption, and accounting practices for audit (i.e. AAA best current practices, etc.). Multiple capabilities need to be integrated to offer a method or application in the field of remote rapid medical care support services.

6. Undue Complexity of Smart Cards, Mobile Phones, and Distress Alert Devices

Other conventional services rely primarily upon identification or smart cards. However, services using a card, in lieu of a device, again simply add a different extraneous layer of complexity and uncertainty. Many are not consonant with the principle of "zero storage and zero transmission", described below, since they sometimes combine biometrics, but only do so in a way that stores or transmits raw biometric data or images as biometric templates. All that is truly needed is a reliable link or pointer to the registrant's ID, RS1, or relevant PHRs, which are network accessible. That simple link or pointer may be discerned elegantly from one or more irreversible transformations or abstractions or the registrant's raw BCD. Each raw BCD source is less separable, if not inseparable, from a victim's person, than is a card. Some emergencies, and often the most dangerous, again, leave persons unconscious, speech impaired, disabled, or in shock, without a driver's license, card, purse, mobile phone, ID document, or wallet in close proximity. Each year there will be still more incidents that leave victims without the ability to gain any truly informed assistance of others in real-time, such as EMRs. Often they are impaired from offering their own identification at the scene, much less any of their 10E data or PHRs content. A better approach would be to enable data access by a biometric-aided mechanisms or cascading set of biometric techniques that can perform, even if, or when, these other conventional approaches do not.

7. Supporting Customized Medical Care Responses Across Age Groups

America is aging. The aged will face special needs in urgent or emergency care. In the United States, the elderly segment of the population is growing fast. With 24 million emergency patient encounters each year, across all age groups, utilizing roughly 40,000 ambulances, there is a burgeoning need to design and use more tailored solutions for emergency responses and urgent health care particularly for the elderly. This upward spiraling demand for rapid remote access to personal data may be viewed separately from the morass of broader health care demands, health care websites, or general PHR archives, such as ones not particularly amenable to priority or privileged wireless access, nor extensible to security and privacy safeguards.

Increasingly, new emergency medical care safeguards and methods will need to be designed, implemented, and operated for specialized classes of emergency responses and treatments associated with other specific medical conditions, distinct emergency circumstances, or personalized directions. They often may need to be designed compatibly to use to build-out ancillary offering of non-emergency health or medical services, PHR archives, or support systems. Field tests for certain devices and procedures that rely on monitoring analogous vital signs for diabetes patients who require urgent care have shown some promise in their use of BCD techniques calibrated for a specialized class of emergencies associated with diabetes. As the median age in this nation rises, with the graying of Americans, it is likely that a broader approach conducive to more specialized customization is needed. For instance, the leading cause of death soon will be from strokes. A stroke is an emergency care matter.

Yet, the elderly and others susceptible to a wider range of relatively predictable or anticipated emergencies have not been afforded access to an advanced set of truly intelligent solutions for informed and personalized assistance. We are unaccustomed to having customized responses for distinct urgent care cases, which concern either identification or verification. Emergency medical responders (EMRs) responses are insufficiently driven by mobile BCD use or PHR accessibility, to deploy personalized responses tailored to registrant directives or instructions. Reliance on the "one size fits all" default response prevalent currently is ultimately inadequate, often dangerous.

9. Customizing Emergency Responses and PHR Access: An Example for Strokes

Today, stroke is the third-leading cause of death in this country, behind heart disease and cancer, killing 150,000 Americans a year, leaving many more permanently disabled, and costing the nation $62.7 billion in direct and indirect costs, according to the American Stroke Association. But from diagnosis to treatment to rehabilitation to preventing it altogether, a stroke is, according to experts, a litany of missed opportunities.

Many patients with stroke symptoms are examined by emergency room doctors who are uncomfortable deciding whether the patient is really having a stroke—a blockage or rupture of a blood vessel in the brain that injures or kills brain cells,—or is suffering from another condition. Doctors are therefore reluctant to give the only drug shown to make a real difference for some kinds of strokes, which is tissue plasminogen activator (tPA).

Although tPA was shown in 1996 to save lives and prevent brain damage, and although the drug could help half of all stroke patients, only 3 to 4 percent receive it. Most patients, denying or failing to appreciate their symptoms, wait too long to seek help—tPA must be given within three hours. And even when patients call 911 promptly, most hospitals, often uncertain about stroke diagnosis, do not provide the drug. (Many ER doctors also fear liability for risks of tPA adverse side effects, without advanced directives or waivers). Some hospitals have neither the MRI equipment nor the needed medical specialist available on staff to administer tPA.

Some elderly people are predisposed to the risk of a stroke due to smoking, diabetes, high cholesterol, coronary artery disease (CAD), or an irregular heartbeat known as atrial fibrillation. Currently, as many have noted, "emergency medical service is not able to respond in the timeframe to save stroke and heart attack victims. New drugs and therapies are available to save these individuals. However they must be administered soon after a stroke. Currently, emergency response is only able to deliver a small percentage of these patients to the emergency room within the treatment window." See G. Kolata, "Lost Chances for Survival Before and After Stroke", New York Times (May 28, 2007). Most folks do not want to "roll the dice" on the more general directive or community customs that concern responses, paramedic procedures, and routing for ambulances. However, without being able to support BCD-driven access by EMRs to rapidly access self-authored directives to get them to the nearest or desired stroke centers, even persons predisposed to suffer a stroke may have no meaningful choice or control when time is of the essence.

To improve the personalization of EMR services, an EMR should be enabled by methods using software to obtain a set of personal emergency health information, preferably with standardized data fields, that is accessible wirelessly, digitally, privately, securely, accurately, and rapidly upon demand. A core set of patient information may be summarized in a patient profile. A patient profile (hereinafter "profile") would preferably be comprised of at least one of the following: the person's name, password, PIN, facial photograph, emergency personal health record file data, one or more fields of ICE data, PHR data, customized advanced directives, special ICE instructions, and other self-entered identifying health, insurance coverage, or financial information.

Current solutions are inadequate. They do not standardize the use of registrant-specific biometric indicators derived from people's physical features or bodies, such that the link between the BCD and an identifier for the rapid identification or verification can become a virtual pointer to the registrant's profile for portability, if only by default. They do not harness collaborative computing to use BCD to generate pointers to accessible files, as needed, rather than files directly and locally stored as consolidated on a single domain. They do not use distributed computing to permit biometric abstraction using software on either client or server sides of the network, as needed. Doing so could allow EMRs to identify rapidly even unknown, unconscious, speech impaired, or disoriented patients by capturing a raw BCD sample for transformation in volatile memory of an EMR's mobile or portable device, by using a biometric information input unit (BIIU), sometimes called a biometric sensor.

These portable devices may include, without limit, either a cellular phone, laptop, Personal Digital Assistant (PDA), Kindle™-like readers, or PDA, mobile terminal, etc., with a camera, image capture apparatus, BIIU, BCD extractor, sensor plate, biometric sensor, or other BCD reader. Biometric abstraction programs may be distributed to these devices, or updated, via data networks. Requests to servers that process the transformed BCD input, or reproduce cryptographic strings from BCD entry, may provoke server result sets or outputs with the patient's specific identifier. An "ID to PHRs" instruction set, or any other resolving program that associates identity and PHRs, may also proceed in two operations, or may be combined into one.

10. Building Upon Related Arts

To surmount such inadequacies, new solutions may build upon certain know-how, or "building blocks", widely used in the prior art. These building blocks may include, without limitation, conventional know-how that concerns either wireless networks, access networks, network security, mobility networks, biometric analyses, pattern recognition, biometrics, image analysis, biometric techniques (i.e., extraction, matching, measurement, cancellation, indexing, encryption, cryptography, classification, etc.), authentication challenges, key management, security measures, or failure recovery mode safeguards, or some combination thereof. Some biometric approaches rely on specialized analyses of samples, and several use pattern recognition or image analyses at one or more stages.

a. Wireless Networks

Wireless networks typically comprise one or more of either the Global System for Mobile Communications (GSM), Universal Mobile Telecommunications System (UMTS), Personal Communications Service (PCS), Time Division Multiple Access (TDMA), Code Division Multiple Access (CDMA), or General Packet Radio Service (GPRS). Often web services for mobility workers are supported by enterprise computing domains that are logically centralized but physically distributed using Wireless Local Area Network (WLAN) technologies, and typically additional wireless network management software. See, e.g., R. Kilan Kehr, et al, U.S. Pat. No. 7,391,060, Mobile exchange infrastructure (Jun. 24, 2008). Still, the artisan in the field could include other mobile networks, mobility networks, cellular systems, RF frequencies, white spaces, or other wireless transmission technologies as well.

b. Access Networks

More generally, an access network may be used for communications with a secure computing environment controlled by a server system. An access network may transport requests from outside the core domain with a connected network that is controlled by a server system. Access networks may be communicable with wireless networks, or more conventional telecommunications systems such as the Internet or the public switched telephone network (PSTN) used for plain old telephone service (POTS), integrated services digital network (ISDN), or virtual private network (VPN). Other access networks are provided, in the form of public or private networks, that are communicably connectable with one or more wireless networks, and include without limit networks compatible with GPRS, such as GSM network, UMTS network, the Internet, VPNs (i.e., mobile VPN, OpenVPNs, provider provisioned VPNs or customer provisioned VPN, etc.), PLMN (Private Line Mobile Network), and PSTN or ISDN. A server system in a domain may communicably connect with wireless communication devices through one or more kinds of networks that also include without limitation many other networks (i.e., OpenVPN, IPv4, IPv6, Ethernet, LAN, WiFi, WAN, etc.). Some IP network software programs that secure data and manage handoffs between networks use IPsec as a security protocol. For other networks, IPsec is not always sufficient as in some OpenVPNs, etc., and further conditioning is required for security.

c. Cryptography and AAA Key Management

Cryptography may be conventional, progressive, or interactive with variables that include, without limitations, time-synchronized data elements, spectrum-specific data structures, data interfaces, or algorithms, whether biometric or not. The AAA Key Management History, in the Appendix to RFC 4962, included by reference herein, reflects how a welter of different and improving Protocols for Authentication, Authorization, and Accounting (AAA) were originally developed to support deployments of Network Access Servers (NASes). [The 4692 Appendix] The RFCs show that there are a growing number of Extensible Authentication Protocol (EAP) methods that may be deployed to wirelessly access database, websites, or other connectible resources. EAP is a universal authentication framework often used in wireless networks, which defines message formats. See, e.g., RFC 3748. Various technologies used with EAP methods are better than others in reducing the risks of impersonators requesting data.

The 4692 Appendix confirms that "[i]n theory, public key authentication mechanisms such as EAP-TLS [RFC 2716] are capable of supporting mutual authentication and key derivation between the EAP peer and NAS without requiring AAA key distribution. However, in practice, such pure two-parry schemes are rarely deployed. Operation of a centralized AAA server significantly reduces the effort required to deploy certificates to NASes, and even though an AAA server may not be required for key derivation and possibly authentication, its participation is required for service authorization and accounting."

Many modern commercial platforms rely upon a recent generation of Advanced Encryption Systems (AES). Since Housley wrote RFC 4962 and its appendix, he has proposed "Using AES-CCM and AES-GCM Authenticated Encryption in the Cryptographic Message Syntax (CMS), under RFC 5083 and 5084. (November 2007). Similarly, X. Boyen, cited in the Cauvokian Paper above, proposed an "Identity-Based Cryptography Standard (BCS) #1: Supersingular Curve Implementations of the BF and BB1 Cryptosystems." (December 2007).

The debate over the optimal improvements will likely continue to rage on, but many upgrades tend to obsolete earlier standards. See, i.e. RFC 5280 Internet X.509 Public Key Infrastructure Certificates and Certificate Revocation List (May 2008). The area is fragmented leading those who rely upon such techniques for patentable methods or devices often to discuss them as a class of interchangeable AAA key management techniques, with certain exceptions in specialized contexts. Where backward compatibility is desired, many Wireless LAN (WLAN) Security configurations apply WPA-2 as the touchstone, or use Advanced Encryption System (AES) with Remote Authentication User Dial-In Service (RADIUS), to protect against rogue access points, man-in-the-middle attacks, and the most common of wireless vulnerabilities.

d. Protecting Customer Data Over Wireless Systems

Using state of the art systems, that are extensible to use with customized software, there are a wide range of Wireless LAN platforms that have improved security to enterprise levels. Some have modular architecture that support 802.11i or WPA-2 Security. Security at this level is generally maintained by ensuring that all equipment is also provisioned for compliance with these or more advanced standards. While allowing operators of such LANs or Mobility Networks to unify communications over certain personal, private, or public networks, the protection of customer data over a variety of wireless systems is commonly managed by employing stronger encryption, authentication, and prevention techniques. By using AES, added safeguards arise including ones that are associated with longer encryption keys and frequently changed keys. Many conventional LANs deploy RADIUS servers that ensure a dynamic IP address may be given to a requester at login time, and deploy one of the more popular EAP types, often to ensure security across the transport or other layers. See, White Paper, 'EAP-TLS Deployment Guide for Wireless LAN Networks' by Cisco, on file with Cisco under as a technologies white paper number 09186a008009256. Many of these measures, along with further Security policies, including special security procedures for wireless transport 102B in turn, help to avoid putting registrant data at risk by denial of server attacks, eavesdropping, and rogue access points. See also, Krishna Sankar, Wireless LAN Security (Cisco Feb. 16, 2008). Modern enterprise security levels are generally security measures at least as robust as AES with either 802.11i or WPA-2 Security. The artisan in the field of Wireless LAN Security will also appreciate that there are several other configuration choices that offer similar security protection.

e. Conventional Registration Through Storing Files, Pointers, or Metadata, Etc.

The registration storing task for many enterprise computing environments or configurations that use database extraction mechanisms presuppose that prospective registrants can avail themselves of conventional or new technologies, especially ones that are backwardly compatible with operating personal computers, telephones, and other workstations, etc. These configurations envision prospective registrants using a registration or enrollment client program (i.e. browser, FTP client program, other application, etc.) to register personal information, or securely upload other data or files, via a remote server or database using the Internet, Web, VPN, or another communication network. The other data or files may include encrypted profile data, links to heath records, robust PINS that can only be descrambled or deciphered using extracted biometric information, biometric patterns, or BCD-related data strings that contain or are derived from some of the registrant's captured data.

f. Fragmented Approaches to Authentication, Authorization, and Accounting (AAA) Systems of Key Management In certain other security spheres, where systemic intrusion at response delivery time poses a more serious risk to data, (i.e., spoofing, impersonations, etc.) some have raised the conundrum of securing content passed through untrusted intermediaries under more stringent assumptions like those common in Homeland Security or financial account scenarios. Special security measures, designed mainly for such untrusted data brokers, intermediaries, and conduits, are highly likely to remain extraneous in most contexts when a medical-oriented or PHR platform is envisaged primarily to enable or enhance rapid health record retrieval remotely. Ordinarily, as far as health profile access is concerned, certain public key methods, other cryptographic methods for communications between two or more parties, or public key infrastructure (i.e. using a trusted authority for certification of signatures, etc) may help provide security which is satisfactory to most prospective registrants, especially when raw biometric samples are neither transmitted from client to server nor stored via the server system.

This is especially so when either a trusted enabling entity may assume the role of the intermediary. The content may remain, for instance, confidentially handled under key management techniques, as when one such as a primary health provider (already entrusted with a registrant's health records or reliably able to bring another intermediary under its privacy policies, etc.) may ensure adherence to privacy policies as a condition precedent to content service. Similar the content may be safeguarded autonomously or under applicable law by the intermediary if it is (a) encapsulated and encrypted but accessible while so opaquely packaged only by a requester with metadata or a cryptographic key, or (b) otherwise transcoded between source and requester. Compare, Nagel, "System and Method for Secure Three-Party Communications", U.S. Pat. No. 7,181,017 (Feb. 20, 2007).

In July, 2007, a consensus on the "best current practice" was memorialized as RFC 4962, entitled "Guidance for Authentication, Authorization, and Accounting (AAA) Key Management, by R. Housely, B. Adoba, et al. RFC 4962 contains an Appendix entitled "AAA Key Management History." It notably reflects that certain reliable conventional authentication processes also exist beyond those AAA Key management techniques surveyed under the rubric of "best current practices." While RFC 4962 did not necessarily alter certain discretely and sole managed security realms or independently controlled solutions that were already conforming to the newly heralded best current practice (i.e., implementing methods applying the "least privileged principle" without plaintext passwords, etc.) it ushered in a new paradigm for better ensuring secure interoperability between distinctly owned, secured or managed domains or realms. Yet, care needs to be taken to ensure personal consent for onward transfers of personal data, beyond a registrant's consent for access or use, in many scenarios.

Without verifiable assurances for common adherence to a standard set of best current practices of authentication, authorization and accounting (AAA), before July 2007, Nagel and others proposed solutions that were commonly designed to surmount some hurdles of untrusted intermediaries, by using multiple communication protocol security mechanisms. With the recent advent of baseline AAA best practices last year (2007-08), discussed below, service providers and database operators alike may now often extend networks more openly, more simply upon verification of security using authentication and related safeguards compliant with such AAA practices of the primary service provider to render qualified corresponding nodes as benign or trusted, to an extent sufficient for encrypted content like profiles and biometric abstraction data.

g. Biometric Analysis: Multiple Techniques for Each Biometric Sources and Pattern Recognition Biometric analysis is one of the building blocks of the new set of methods. Many techniques have evolved to design or use corresponding methods for the automated recognition of a pattern, or, when appropriate, image analysis. Included hereunder are systems that transform an image for the purpose of (a) enhancing its visual quality prior to recognition, (b) locating and registering the image relative to a sensor or stored prototype, or reducing the amount of image data by discarding irrelevant data, and (c) measuring significant characteristics of the image. Image analysis, when utilized, may be extended to encompass certain systematic operation or series of operations performed on data representative of an observed or observable image with the aim of measuring a characteristic of the image, detecting variations and structure in the image, or transforming the image in a way that facilitates its interpretation.

Unlike the limited range of image analysis in some references, our expanded scope of image analysis, however, extends images obtained by a camera, scanner, or image detector), wherein the image represents the actual scene, to the presentation or generation of images that are (a) computer generated or otherwise artificial, or (b) a combination of computer-generated images and real images, including for computer graphics and control of data presentation with creation or manipulation of graphic objects or text performed by a computer or processor, and operator interfaces. Similarly, in this context, image analysis also extends to reading or sensing of coded indicia, which does not include the recognition of any alphanumeric character or pattern, including coded indicia that are designed specifically to facilitate reading by machine and are not intended to be read by humans. Moreover, we include under the extended rubric of image analysis certain adjacent arts that pertain to the processes that concern pattern recognition or the encryption of data, including character data.

While the artisan of ordinary skill is aware of the more extensive range, it is helpful to point out features of some of the related arts that are associated with the "building block" of pattern recognition methods or image analysis applications that may support the purpose of recognizing an individual or verifying a person's identity while protecting privacy and maintaining security.

A pattern is any form in an image having discernable characteristics that provide a distinctive identity when contrasted with other forms. Pattern recognition is any procedure for ascertaining differences, or similarities, between patterns under observation. It may entail partitioning the patterns into appropriate categories based on these perceived differences or similarities; or any procedure for correctly identifying a discrete pattern or class of patterns, such as an alphanumeric character or coded indicia associated with pattern or characteristic, as a member of a predefined pattern category. As to biometric patterns, biometric character data may evince patterns that manifest themselves to detection by human senses, computers, sensors, or other machines, or a combination thereof; in various ways, and are often subject to classification in some original or transformed state or format using metadata, with or without an ontology.

In biometric processes, including many used to support identification, verification, or authentication, it has been shown that algorithms designed for 1:1 verification traditionally scaled poorly when used for 1:N identification tasks. See e.g., R. Cappelli, D. Maio and D. Maltoni, "Indexing Fingerprint Databases for Efficient 1:N Matching", in proceedings Sixth International Conference on Control, Automation, Robotics and Vision (ICARCV2000), Singapore, December 2000.

While many experiments have been conducted to perfect biometric pattern recognition, with ever-increasing performance capabilities and higher confidence levels, the studies have tended to show a trade-off between accuracy and rejection rate. Still, biometrics is rapidly replacing traditional token and password methods. There is insufficient space to survey all the biometric sources, recognition applications, or techniques here. Many are functionally interchangeable for health care support purposes with the most universally deployed ones like fingerprints. Of all the biometric modalities, fingerprints have emerged as a popular choice due to their universality, distinctiveness, permanence and acceptability. Another reason for their popularity is the wide range and variety of implementations of recognition algorithms that are already available. A limited summary of thumbprint or fingerprint biometrics, below, is useful to exemplify how biometrics may provide support for certain acts of the mediation processing, and particularly when reliance upon some biometric abstraction model advances a result. The artisan in the field will appreciate that further citations of the crowded field of biometric techniques, that may be used in place of fingerprints, and beyond the citations included herein, would be of diminishing value, since salient principles of functionality in the inventive context are common to most biometric sources, but may vary as to degree, acceptability, or ease of use.

The website of the Biometric Systems Laboratory, DEIS—University of Bologna, Italy (BSL), explains that "Fingerprint recognition is a complex pattern recognition problem; designing algorithms capable of extracting salient features and matching them in a robust way is quite hard, especially in poor quality fingerprint images. There is a popular misconception that automatic fingerprint recognition is a fully solved problem since it was one of the first applications of machine pattern recognition almost fifty years ago. On the contrary, fingerprint recognition is still a challenging and important pattern recognition problem." See, e.g., Zhengmau Yo, Yongmao Ye, H. Moamadian Biometric Identification via PCA and ICA Based Pattern Recognition, ICCA 2007, IEEE Intl Conf. on Control and Automation.

The BSL explains that "[a] fingerprint is the reproduction of a fingertip epidermis, produced when a finger is pressed against a smooth surface. The most evident structural characteristic of a fingerprint is a pattern of interleaved ridges and valleys; in a fingerprint image, ridges (also called ridge lines) are dark, whereas valleys are bright. Ridges and valleys often run in parallel; sometimes they bifurcate and sometimes they terminate. When analyzed at the global level, the fingerprint pattern exhibits one or more regions where the ridge lines assume distinctive shapes (characterized by high curvature, frequent termination, etc.)." These regions (called singularities or singular regions) may be classified into distinct typologies, which include the loop, delta, and whorl.

The BSL continues: "At the local level, other important features, called minutiae, can be found in the fingerprint patterns. Minutia refers to various ways that the ridges can be discontinuous. For example, a ridge can suddenly come to an end (termination), or can divide into two ridges (bifurcation). Although several types of minutiae can be considered, usually only a coarse classification is adopted to deal with the practical difficulty in automatically discerning the different types with high accuracy. At very-fine level, intra ridge details can be detected. These are essentially the finger sweat pores whose position and shape is considered to be highly distinctive." The BSL also explains associated advances in feature extraction through conventional techniques of binary representation and thinning using various algorithms, as well as newer techniques like gray-scale Minutia Detection Approach.

Today, even in the sub-field of biometrics dedicated to fingerprints, there are scores of algorithms available to support identification or verification. In U.S. Patent Application No. 20070297653, dated Dec. 27, 2007, Bolle; Rudolf Maarten, et al, have proposed, for instance, a "Fingerprint representation using localized texture features" and they describe many of the kinds of algorithms and key deficiencies of conventional analytic techniques, as follows "Existing fingerprint matching algorithms may be broadly classified into the following categories based on fingerprint representation.
1. Correlation based: In this representation, the fingerprint image itself is used as a template. Matching is performed by measuring the result of cross correlation between the two images. This . . . is very fast, since correlation may also be implemented through optical techniques. . . .
2. Minutiae Representation: Minutiae represent local fingerprint ridge discontinuities and mark the position where a ridge comes to an end or bifurcates into two. Given target and reference fingerprints and their corresponding minutiae features, the process of matching is a point pattern matching problem. This is by far the most popular approach to fingerprint recognition.
3. Texture Descriptors: A fingerprint image can also be viewed as a pattern of oriented texture formed by the gray scale variation of the ridges. Therefore, texture descriptors provide a good representation for the ridge content in the image. A global texture descriptor scheme called 'finger code' utilizes both global and local ridge descriptions."

In fact, numerous comparison processes have relied upon the aforesaid characteristics as well as others like the observance of motifs such as deltas, bifurcations, terminations, pores, ridges, and valley, and others. Often motifs are measured in relation to one another or some estimated center of the thumb.

The BSL also properly frames how some of the remaining challenge are being surmounted using classification: "The identification of a person requires the comparison of his/her fingerprint with all the fingerprints in a database, which in large scale applications may be very large (several million fingerprints). A common strategy to reduce the number of comparisons during fingerprint retrieval and, consequently, to improve the response time of the identification process, is to divide the fingerprints into some predefined classes. Fingerprint classification means assigning each fingerprint to a class in a consistent and reliable way, such that an unknown fingerprint to be searched needs to be compared only with the subset of fingerprints in the database belonging to the same class. While fingerprint matching is usually performed according to fingerprint micro-features, such as ridge terminations and bifurcations (minutiae), fingerprint classification is usually based on macro-features, such as global ridge structure. All the classification schemes currently used by police agencies are variants of the so-called Henry's classification scheme. Five classes (Arch, Tented arch, Left loop, Right loop and Whorl) are commonly used by today's fingerprint classification techniques. In reality, fingerprints are not uniformly distributed among these five classes: the proportions have been estimated as 3.7%, 2.9%, 33.8%, 31.7% and 27.9% for Arch, Tented arch, Left loop, Right loop and Whorl, respectively. Aside from the Tented Arch, each of the others usually has a center or "core." Notably one variant of the Whorl, called a Whorl (Twin Loop) has a double core. *Biometric System Laboratory, DEIS—University of Bologna, Fingerprint Classification, on file with Biometric System Laboratory.* See also, ISO/IEC 19794-2, et seq., on Fingerprint standard templates, revisions thereto at ISO/IEC WD 19794-2; and compare, ISO/IEC 24713-1 (2008) [Biometric profiles for interoperability and data interchange]; ISO/IEC 19795-4(2008) [Biometric performance testing and reporting—Interoperability Performance testing.]. Many approaches embrace either all five variants while other rely on distinctions primarily among four kinds.

Fingerprint classification may take a variety of forms, and many draw a general line between Exclusive Classification and Continuous Classification. Exclusive Classification entails several approaches that include, without limit, fingerprint classification (a) by means of inexact graph matching; (b) using dynamic masks to partition the directional image, or (c) based on MKL by relying on subspaces well suited for representing fingerprints belonging to the class under Henry's scheme, above. Continuous Classification, typically seeks to surmount the constraints of low number of classes and skewed distributions hampering these other approaches, by associating each fingerprint in a multidimensional space through a similarity-preserving transformation, such that similar fingerprints correspond to close points, using radius measurements.

The BSL website also explains: that "[t]here has been a substantial amount of work done on the multimodal fusion approaches: the key is the combination of the various biometric characteristics at the feature extraction, match score, or decision level. Feature level fusion (also known as pre-classification fusion) combines feature vectors at the representation level to provide higher dimensional data points; match score level fusion and decision level fusion (post-classification fusion) combine the individual scores from multiple classifiers and the accept or reject decisions of each biometric system, respectively." See also, M. A. Ferrer, A. Morales, et al., "Low Cost Multimodal Biometric Identification System Based on Hand Geometry, Palm and Finger Texture 2007 41st Annual IEEE Intl Carnahan Conf. on Security Tech. Another approach takes the multimodal approach in another direction to combine biometrics with a secret sequence code. "See, e.g., Pu, et al., U.S. Pat. No. 6,229,906, "Biometric sequence codes." (May 8, 2001). Rather than combine fingerprints, vascular, or iris data with other one another or other biometric modalities, the '906 patent offers an identification system using biometric information of human body parts and a secret sequence code. In particular, biometric information of human body parts is used to form the secret sequence code. Specifically, a combination entry device recognizes user's fingerprints which are entered as a sequence. The fingerprints must be entered in the proper sequence in order to be recognized by the system.

As was true with multimodal biometric techniques, some have used combined methods of classification, or beneficially deployed other alternative approaches. See, e.g., R. Cappelli, D. Maio and D. Maltoni, and L. Nanni, "A two-stage fingerprint classification system", in proceedings ACM SIGMM Multimedia Biometrics Methods and Applications Workshop (WBMA03), Berkeley, pp. 95-99, November 2003. In this paper they "describe a fingerprint classification system based on a two-stage sequential architecture: an MKL-based classifier is first used to select the two-most-likely classes and then a second classifier (specifically trained to discriminate between the two classes) is then adopted for the final decision. The experimentation performed on NIST Special Database 4, which is one of the most important benchmark in this area, shows that the new approach yields an error rate lower than previously published in the literature. In particular, the error rate is 4.8% and 3.7% for the five-class problem and four-class problem, respectively." Some studies show that classification systems using a combination of minutia, orientation image, and finder code, may often enhance performance by reducing error rates, especially at lower penetration levels. See, e.g., slide 20, R. Germain et al, IEEE, Fingerprint matching using transformation parameter clustering; G. Bebis et al, IEEE Fingerprint Identification Using Delaunay Triangulation, *IEEE International Conference on Intelligence, Information, and Systems* (ICIIS 1999).

Further advances have been achieved in biometric identification by using techniques that combine approaches, or use indexing to exclude the vast majority of records in the universe of potential matches, to establish a narrowed candidate list. See, e.g., Fengling Han, Jiankun Hu, and Xinghuo Yu, A Biometric Encryption Approach Incorporating Fingerprint Indexing in Key Generation, Lecture Notes in Computer Science (Springer 2006). In turn, the process may then apply a 1:1 verification test or set of examinations, using one or more algorithms, to rank candidates or isolate a match, if any exists. See, e.g., Lo, U.S. Pat. No. 7,313,256, entitled "Progressive fingerprint matching system and method", Dec. 25, 2007; see also, Reisman, James G.; et al., United States Patent Application No. 20030169910, Fingerprint matching using ridge feature maps Sep. 11, 2003. As to combined approaches, Reisman asserted "[w]hile a ridge flow pattern is generally used for classifying fingerprints, it is seldom used for matching. The [inventors] provide[ ] a fingerprint matching method that uses ridge flow information to represent and match fingerprints."

While accuracy and performance will continue to be the subject of many unforeseeable improvements in biometrics and image analysis, the art is already at a state that offers promise in certain adjacent art that concerns mediation that uses biometrics or image analysis, or both, as one building block. For example, the techniques that offer a combination of biometrics with identification, verification, authentication, cryptography, classification, or indexing, etc, will continue to bourgeon. See, e.g., Setlak, U.S. Pat. No. 6,795,569, "Fingerprint image compositing method and associated apparatus" Sep. 21, 2004; Ziesig, U.S. Pat. No. 6,941,003, "Method of fast fingerprint search space partitioning and prescreening" Sep. 6, 2005; Thomas, et al. U.S. Pat. No. 7,237,115, "Authenticating concealed private data while maintaining concealment" Jun. 26, 2007. For each of these techniques the field of know-how is already crowded, and in most cases the maturity suggests that newer innovations present a third or latter generation. As such, they now offer configuration choices to those creating methods or application in reliance upon various permutations of their principle features, functionalities, or capabilities.

Accuracy and performance reside in the sphere of quality of service parameters, that are often relevant to the value of an operable system using the invented method, but not essential to the architecture or functionality of the far more fundamental method of mediation. Accordingly, given the wide choices available to mediator operators, we take them as a variable array of interchangeable alternatives, whether for fingerprints, irises, or other biometric sources, which appear to be sufficient and improving. Numerous biometric techniques are surveyed, for instance, in a number of books, texts, and other resources, like one by John R. Vacca, Biometric Technologies and Verification Systems, Butterworth Heinemann (Mar. 16, 2007). The mediation methods, described below, do not purport to disclose the means of optimizing all biometric or image analysis techniques, but instead mate the steps of using a wider class of either biometric or image techniques with steps of novel mediation methods that are transformative for rapid health-care support methods. The present invention may rely upon or encapsulate even novel biometric or image analyses techniques or biometric abstraction models that are trade secrets, without disclosing any new biometric identification methods of general applicability (i.e. outside rapid EMR class-accessible remote health-support, etc.).

Because conventional health support services that rely upon tangible devices or cards, may now be superseded by solutions that utilize biometrics, there is a growing appreciation of the need to protect both the personal health information and the raw biometric data, which individuals can little afford to lose or relinquish control over. To ensure that raw biometrics may not be diverted to unauthorized uses, certain biometric approaches offer the promise to safeguard the privacy of the raw biometric data by decoupling the raw data from their associative properties by utilizing abstraction. These approaches increasingly use one or more biometric abstraction models that leverage the power of raw biometric data, without exposing raw biometric data to risk of misuse or loss. The integrating approaches taught below therefore do not transmit via network, or store in non-volatile storage, the person's biometric data in any form, unless it has been transformed to prevent against reconstruction of raw biometric data by eavesdropping persons or imposters. These offer query resolution virtually "risk-free of reconstruction."

10. A Health-Support Method Using Software May Employ Query Processing, but May Differ from Conventional Security Applications in Other Sectors of Commerce or Governance Unlike many security scenarios, we are usually dealing with friends, not enemies. For rapid health care support, we should usually provide relevant information expeditiously under the principle of least privilege, especially since one of the following assumptions is applicable: a) it may be possible to rigorously classify the data, a priori, by potential recipient for privacy; b) the collected information may be organized according to the needs of a privacy protocol; or c) it may be fully determined from the queries submitted by potential recipients whether the results might improperly risk including information that should be withheld. RFC 4949 notes in a tutorial under the definition of "authentication information", how conventional services often use two-stage authentication. Already a number of services will not process a request unless a party seeking data can qualify using two of the three requirements below to authenticate identity: (i) something he possesses; (ii) something he knows, and (iii) something he is. See, RFC 4949 at p. 5. Another form of two-stage authentication could require a smart card and a PIN derived from a biometric encryption template.

In all events, the best current practices of AAA for interoperability of distinctly owned or controlled domains, servers or applications, along with key management improvement, may at least in some cases be used to obviate the convention of classifying between domains or systems that are trusted, benign, or untrusted. See, e.g., RFC 4962, Internet Security Glossary Version, 2. R. Shirey (August 2007)(under the definition of "trust"(1)). After RFCs 4949 and 4962 were issued, new proposed standards were published under RFCs 5191 and 5193 that concerned the "Protocol for Carrying Authentication for Network Access (PANA) Framework", dated May 2008. Notably, the term "authorization" in certain RFC contexts denote "network authorizations" parameters (i.e. limited number of entries, bandwidth constraints, etc.), in contrast to network-agnostic "authorization" to gain application access, or data with content (i.e. profile payloads, PHR envelopes, advanced directive cryptolope, etc.), or other use privileges, as used elsewhere herein.

11. Server Platforms May Use Request-Response Messaging Over Wireless Networks

Current conventional methods do not adequately integrate or loosely couple software that can control a process to galvanize conduit (i.e. communication networks, wireless access protocols, request/response messaging, etc.), computer processing (i.e. server systems, CPU, processing units, etc.), base resources (i.e. content, updates, databases, etc), and layers of applications (i.e. programs to handle or manage connectivity, authentication, unscrambling registrant-specific identifiers using biometrics, registration, authorization, security, policy, auditing, etc.) Accordingly, EMRs, and particularly ones seeking profiles of persons not readily identifiable, will need "something more" to improve upon conventional methods that are designed mainly to serve hospital networks or health care providers, rather than enable protecting patients rapidly.

In other contexts, computer scientists call that "something more" a mediator. Usually, a "mediator consists of general hardware and specialized software to implement a high-level concept in providing added-value services. . . ." A mediator, however, also may be a software module that exploits encoded knowledge about some set or subsets of data (i.e., by value-added processing, etc.) to create information for a higher layer of application. A software architect or systems integrator may specify a mediator. Separately, the mediator may be implemented or used by an entity called a mediator server operator to attain query resolution at runtime. In some open mediation methods that rely upon request-response messaging, a server system provides trade-support by enabling messaging so that unaffiliated "service providers" may enter service listings and unaffiliated "service consumers" may query databases, communicably connectable to the mediator server system ("mediator server"), to match or retrieve selected data. Compare, Hoffer, U.S. Pat. No. 5,799,151, An Interactive Electronic Trade Network and User Interface (August 1998)

Using other techniques common for providing pervasive or wireless system security to digital assets (i.e., public or symmetric key management, etc.), a server may be configured to provide access control management whenever queried by a client program that requests access to private or secured data. Since request-response messaging may describe message flow patterns between client programs and server programs simply to acknowledge or handle message exchanges to transmit data of query, any reliance on this kind of message pattern does not imply that every result set produced by a server need be transmitted as response message to anyone. Any discretionary enablement of a response coupled with a result set is to be comprehended in a distinct context of what ordinarily occurs above the Application Layer of a data network.

Some earlier mediation methods that ensure security consist of steps or modules that perform the following tasks: processing of query (pre-processing); communication with databases (submission of query and retrieval of results); processing of results (post-processing); and writing into a log file. See, G. Wiederhold, U.S. Pat. No. 6,226,745, Information sharing system and method with requester dependent sharing and security rules (May 1, 2001). See also, G. Wiederhold, Interoperation, Mediation, and Ontologies, (Nov. 9, 1994), (Nov. 9, 1994), also on file with the InfoLab, Stanford University.

Such security methods may employ a rules system, view-based access controls, a combination of pre- and post-processing constraints, or one or more queries. As with many conventional methods using software to enable message exchange, a successful query of verification to retrieve personal data or of identification, may only fruitfully follow a compatible enrollment or registration. To process such a query, beyond the adjacent art of security mediators, certain modern mediators may usually initiate a message flow to invite a peer, like an EMR using a mobile client application, to authenticate credentials and preprocesses a request of resolution. A mediator's server system and software use data of request as data of a query. The mediator processes a query, in view of an authentication assertion, and once the subject identification or verification is to be accomplished, if at all, the mediator typically looks up a mediated object, file, or pointer in accessible storage, where the mediator expects to get the stored data of the registrant, and applies privacy rules to retrieve the result set. The mediator may or may not be configured to package the result set into a response to send it encrypted over some network.

If the enrollment module is native to such a modernized mediator, and external storage services are extraneous, then the mediator can substantially govern any compatible inter-operations between the requester's service model and the provider's service model, since the mediator alone controls the latter model at both enrollment and query time. Other possible solutions, where external provider service models can play a role in query resolution, often rely more upon process mediation than data mediation. A mediator may enable execution of a query as if it were operating under at least one provider's service model to access data stored during enrollment. Often that model may encapsulate a biometric abstraction model. See generally, R. Vaculin, K Sycara, Towards automatic mediation of OWL-S process models, (Robotic Institute, Carnegie Mellon University), also on file with the Robotics Institute, Carnegie Mellon University. These provider's service models commonly control message flow patterns.

A mediator, such as one without a native enrollment module, may be tasked with discovering a provider service model externally, which may be compatibly invoked by the requester's service model. To this end, the mediator may need to use certain process mediation techniques, to reconcile different message flow patterns of either one or more non-native models or to reconcile other distinctions. See, e.g., Web Services Execution Environment (WSMX) (WC3 Jun. 3, 2005) also on file with the W3 organizations, a technical standards setting body. Sometimes, the mediator may adapt request-response messaging patterns to reconcile the different service models of requesters and providers. Some process mediation anticipate reworking the message flow toward a harmonized pattern by either splitting messages, unifying messages, inverting messages, omitting messages, or creating acknowledgements, etc. Some approaches to support process mediation include, without limitation, combining or compositing processes by using control constructs such as: sequences, any-order choice, if-then-else, split, split join, repeat-until, or repeat-while, etc. Process mediation also may, as a preliminary measure, require using as an input for results certain output of data mediation. Data mediation, as explained herein, could reconcile two related biometric abstraction models, utilized in separate service models of a requester and a mediator. In turn, a translation could be used in certain instances to permit adaptation of the query, data, or message flows, as needed, to iterate through a database of either the local mediator or an autonomous external service.

Among health care systems, which are aided by biometric technologies today, there has been inadequate attention paid to satisfying the urgent needs of EMRs seeking data from remote facilities or locations, often when time is routinely a true matter of life or death. The adjacent art does not appear to suggest or teach how a mediator may be composed or run to enable a requester to rapidly attain a registrant's profile or health records privately and securely over networks, including one that is at least partly wireless, by using biometrics, but without either persistently storing or transmitting the raw biometric data. Nor do conventional methods approach how to compose a mediator for health care support to enable resolving how a requester may do so promptly, when the identity of the registrant remains unknown to the EMR. Most biometric systems for sharing private health data remotely entail verification or a predetermined identification, by using centrally stored raw biometric data. Yet, progress is developing in highly lucrative financial and transport applications relying upon transformation biometrics (i.e. cancelable biometrics, biometric encryption, biometric indexing, or other biometric methods, etc.), and key management techniques. Even if a registrant is unidentifiable prior to query time, better techniques using biometric abstraction models can help empower the registrant to control the anticipated access, use, privacy, and secure remote transmission of his profile or associated data, under a new set of secure health-support mediation methods using software, with zero-storage and zero-transmission of raw biometric sample data.

When a person is in need of health support services, and especially when in urgent need, either (a) he or she is readily identifiable without biometric techniques, or 7 (b) he or she is not so readily identifiable. In the latter event, it is commonly desirable for qualified EMRs to be able to identify the person or to use an individual-specific identifier to request that person's data or profile. To this end, a method using software may be enabled to process remote requests to ascertain identification or other personal data, such as profiles, securely and privately, by harnessing the associative, disambiguating, or distinguishing capabilities of biometric data techniques. The methods may rely on conventional access or wireless networks to transmit a request over data networks and via server facilities to convert a request into a query. Ordinarily mediation is invoked when an EMR presupposes that a person is a likely registrant, and seeks to substantiate this assumption. Conversely, the participation by a registrant in any of these mediation methods indicates the registrant's consent, express or implied, to permit limited disclosure or transfer of personal data like profile content to some remote EMRs under applicable rules.

One of the goals of the invention is to enable mediation of such a request, and processing thereof, entirely free of material risks of any compromise of an actual or potential registrant's raw biometric sample data. The set of methods described below are designed using acts without any sharing of data that may be traced back to, or may be reversible into, raw biometric data. Reliance by a server system upon data that is reversible, directly or indirectly, into any registrant-specific part of a raw biometric data would raise untenable or avoidable risk that privacy-sensitive biometric data may be detected, deciphered, misused, or reconstructed by others, who are without registrant-granted privileges to do so.

SUMMARY OF THE INVENTION

The deficiencies of the conventional approaches are surmounted by making or using one or more mediation methods that use specialized software, with generalized hardware such as a server system, to produce a result set by using a registrant's transformed biometric data to securely advance query resolution, risk-free of reconstruction, upon receiving a remote request from one other than the registrant, which request seeks the registrant's personal health or identification data, under all of rules of the mediator that apply.

A mediator is designed to run specialized software that powerfully automates or formalizes the role of a privacy officer, who has the responsibility and the authority to resolve a query seeking a result set. As such, the methods use mediation software that enables query resolution. According to one general aspect, the specialized software supports receiving a request with biometric-derived data sent via at least one mobile network, enabling execution of a query using a stored set of rules, executing the query to process results using a biometric abstraction model, and extracting data of an associated registrant from a database. The extraction processes may facilitate either producing or using a result set, as permitted by the rules. This biometric query-resolution mediator ("BQR Mediator") controls the processing of a request, for certain personal data or identification of a possible registrant, even if sent by some person or application other than the registrant, by resolving one or more queries, as to verification or identification, or both. The BQR Mediator can process a remote data request by an EMR, whether it is sent via a network that is wireless in any part, or not. No registrant's private health information leaves a mediation domain, unless the data of the result set has been so resolved without constraint under any applicable rule or policy.

The methods use software that will block or constrain a request if the corresponding query cannot be fully processed, particularly in view of any applicable rules that protect private data or metadata. The BQR Mediator is queried at runtime by directly or indirectly, explicitly or implicitly, internally or externally, using one or more sources of biometric data, without requiring transmission to the server system of raw biometric data itself or any data reversible thereto. Usually, but not always, a query is formed, recognized, or distilled from the data of an EMR's request, for processing or some other means of interrogating a database. The method primarily mediates requests made remotely for data of a registrant, without any common identity of registrant and requester, and even without any prior relation, agreement, or privity between a requester and a registrant. Requester may be affiliated with one or more different organizations, which may include or exclude the mediator operator. One mediator operator may support one or more requester service models with various parameters dealing with some combination of data request format, biometric abstraction model, transport protocol, security, and/or data capture mode.

Mediation recognizes the autonomy and diversity of the data systems and information services that support the computing hubs for selective transformation, processing, and sharing processes, and of the requesting applications that utilize them. The principal tasks in mediation are the identification of relevant resources for the requester model to advance the processing, retrieval, or reduction of the relevant data for the requester inquiry. To match the requester needs to the resources of the BQR Mediator, we begin by recognizing that the request is transmitted to the server system. Notably, neither the data representation transmitted by a request nor the data representation stored at enrollment can disclose, consistently with mediator rules, either replications of sensitive aggregates of a person's raw biometric source or even data directly representing it if susceptible to reconstruction. Instead, both rely upon some form of abstraction of some representation of raw biometric data. It then becomes incumbent upon the designer of the mediator to enable a matching process that is based on mapping the requester's biometric abstraction model onto the biometric abstraction model of the server system using accessibly stored data or resources. Since the mapping is part of the design process, the database may be configured to perform services that either pertain to mapping methods of abstraction that bring materials to matching levels of granulation or to resolving domain terminology and ontology differences.

Matching the query data of a request under one model with data of a server system under a resident model at a server system requires that the terminology used to describe objects and their attributes match. Here, both models, which may be the same (in a simple case) or different (in a more complex case), are intended to correspond with one another to support mediation. The nexus may either be direct or by adaptation. The BQR Mediator's operations may rely upon one or more abstraction technique that can transform or process the data used to extract output from a database, either by automating processes to summarize the data being mapped or by establishing procedures for reporting exceptions, or both. Both functions typically depend on having a reusable hierarchical model of the requester's needs. In all events, the resolution of queries transmitted over a secure wireless exchange infrastructure may be automated to generate results either by using metadata about information resources, logical statements relating to disparate concepts, or format descriptions for data being accessed.

The correspondence between the models should be conducive to permitting the mediator to provide integrated information, without linking base data resources, particularly in complex cases. This may be achieved by integrating the homogenized data, using the same semantics and representation, for example, according to matching keys. As a design choice, the BQR Mediator may support one or more compatible biometric abstraction models that enable the mediation of request resolution. The range of objectives of the BQR Mediator may concern not only the ones stated above, but also other objectives that ensure consistency with principles of least privilege, AAA best practices, wireless security, analytical optimization, or algorithm independence. Due to remote access, compatibility with rapid or emergency care, and third-party entrustments running in favor of limited disclosure to an EMR, these mediation methods will have versatility that goes beyond certain hospital network scenarios, for instance, to remote locations wirelessly or nodes of one or more mobility networks. Again, in this context, it typically may be determined from the queries submitted whether the result might improperly risk including information that might be held.

We characterize the conditions that mediator software needs to perform query resolution, while controlling privacy of each registrant's personal information and raw biometric sample data. In one configuration of the BQR Mediator, for example, the specialized software is composed to implement mediator procedures that facilitate the registrant's self-administered privacy rules. These conditions help to convey how a method using software with a server system may be developed or deployed to operate a BQR Mediator. The BQR Mediator's software automates query resolution by using registrant-specific identifiers (RSIs), which are processed without transmitting one or more registrants' raw biometric data through networks or storing raw biometric data on the mediator's server system. These identifiers are either: (a) metadata of a registrant's raw biometric data, or a portion thereof, (b) some representation of a registrant's transformed biometric data, or a portion thereof, or (c) one or more data sets, identifiers, or constructs, that are at least partly biometrically-generated, and are otherwise interchangeable with (a) or (b) above, within the know-how of an artisan of ordinary skill. The alternative approaches are aided by biometrics, but similarly deployed by the BQR Mediator risk-free of reconstruction.

Some of the methods are extensible to utilize one or more autonomous external processes or backend storage services, as well as handle diverse requesters. If the BQR Mediator supports interoperability with one or more external enrollment or personal information storage services, the BQR Mediator's specialized software that enables execution may mediate by employing one or more external provider's service models. These external models may entail different message patterns, or variances in preconditions, events, biometric abstraction models, inputs, outputs, sequences, or formats. Interoperability may be conditioned upon complying with privacy, security, AAA best practices, or other rules of the external domain. As such, some of the invented methods may deploy the specialized software that enables mediation between two non-native processes that can be loosely coupled, such as: (i) one using a requester's service model (RSM), that may be one of several (i.e. $RSM_{1...n}$, n≥1), and (ii) one using an external provider's service model (PSM), that may be one of several, (i.e. $PSM_{1...n}$, n≥1).

By loosely coupling an autonomous external service (i.e., that enrolls personal content, can share a PSM, or provide value-added services, etc.), the BQR Mediator may interoperate so as to enable a requester to invoke either external processes or resources. In the latter event, the BQR Mediator may support "process mediation" to reconcile, reduce, or resolve mismatches between the service models of the requester and an autonomous external operator. By utilizing translation/mapping between the two process models, or using knowledge of their other detectible differences, such process mediation may advance resolution of an otherwise irresolvable query. When a BQR Mediator operates unattended such mismatches are reconciled by mediation using programmatic resources. For example, if an autonomous external database requires a participant's digital signature or robust PIN for onward transfers of personal information of an identifiable registrant, the BQR Mediator may facilitate an EMR's retrieval of that signature or PIN for that participant by locally deploying, with the help of data of the request sent over a wireless network, a biometric encryption technique to ascertain the signature or PIN, in one embodiment.

The invented methods described for illustration below notably do not specify any exclusive approaches to enrolling, extracting, matching, encrypting, decrypting, processing, classifying, analyzing, composing, indexing, or measuring a single kind of biometric data or any potential combinations of approaches, which are continuously being improved. The alternative embodiments of the methods typically share certain operational specifications in common with biometric abstraction models preventing reconstruction, that include biometric constraints of zero-storage and zero-transmission, as described. Some mediator operators may support combinations of some configurations of the methods with more common systems or techniques that primarily satisfy either a registrant's request for her own personal information or her enrollment needs, since they may integrate or loosely-couple the latter as a complementary add-on service. Some configurations may include at least one rule that categorizes one or more certain kinds of content, protocol, or process mediation as ones of a premium service, and of a basic service. Most, as well, may be designed with adherence to principles of wireless security, accountability, safe programming, algorithm independence, and least privilege.

BRIEF DESCRIPTION OF THE DRAWINGS

The present invention is illustrated by way of example, and not by way of limitation, in the figures of the accompanying drawings in which like reference numerals refer to similar elements and in which:

FIG. 1B shows a partial view of FIG. 1A to exemplify a set of communicably connectable hardware devices to store or forward data communication for such processing, which set comprises: (a) a mediation system that can run on a server, (b) a registrant communication device, as needed, that typically couple certain functions of a biometric information input unit (BIIU) with a compatible computer, and (c) another communication device of a mediated party, or wireless telephone, that can at least transmit data.

FIGS. 3 A and B are a generalized and a more detailed flow diagram, respectively, depicting a certain set of operational acts controlled by the mediation software of a BQR Mediator, in accordance with one set of embodiments of the invention.

FIG. 4 is a block diagram of some of the computing tiers of a mediator that may be used to implement an alternative embodiment of the invention.

FIGS. 6A, 6B, and 6C are block diagrams, in which FIG. 6A depicts a set of data structures, FIG. 6B depicts the set of procedures to control privacy, FIG. 6C depicts the set of procedures to control security over one or more wireless networks, used by the mediator server system, in accordance with an alternative embodiment of the invention.

FIG. 11A is a diagram depicting a wireless communication device capable of transmitting requests with BCD content, or performing services of a web server to transport BCD-oriented requests or input, over mobile services transport in connection with wireless networks, or wireless networks augmented by landline networks, in accordance with another embodiment of the invention.

DETAILED DESCRIPTION OF THE PREFERRED EMBODIMENTS

A method is described that uses software to resolve a query upon remote request over wireless facilities from one other than the registrant, which rapidly seeks the registrant's personal health or identification data, by using a registrant's transformed biometric data, risk free of raw biometric data reconstruction. In the following description, for the purposes of explanation, numerous specific details are set forth in order to provide a thorough understanding of the present invention. It will be apparent, however, to one skilled in the art that the present invention may be practiced without these specific details. In other instances, certain well-known structures, application modules, systems, and devices are shown in block diagram form in order to avoid unnecessarily obscuring the present invention. It should be understood that the described processes are not intended to be limiting of the ways in which the health care support methods of mediation may be performed in a different order, and some of the processes, acts, or components may be omitted if not required.

Embodiments are described herein according to the following outline: 1.0 General Overview; 2.0 Structural and Functional Overview; 3.0; Specialized Software Overview—Some Implementation Approaches; 4.0 Method of Mediation for Rapid Health-Care Support Information Via A Secure Wireless Network; 5.0 Extensions; and 6.0 Alternatives.

1.0 General Overview

Figure 1A:
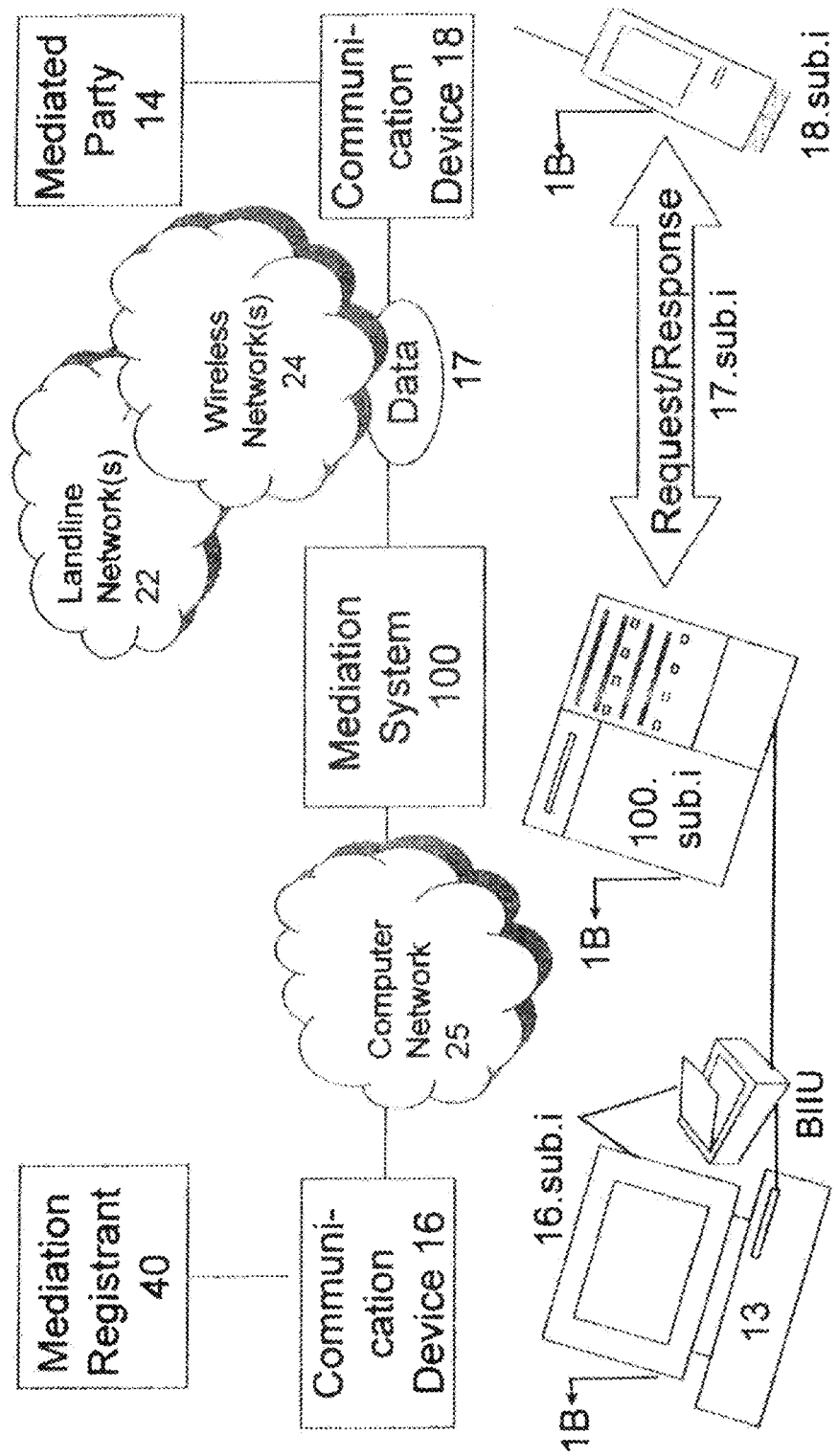
FIG. 1A is a block diagram depicting an embodiment of a communication system including a mediator capable of processing data in an environment including TCP/IP, landline data, and wireless data communications, in accordance with an embodiment of the invention.

FIG. 1 is a block diagram showing a structure of a BQR Mediator that may resolve biometric queries, according to an embodiment of this invention. As shown in FIG. 1, the method to make or use a mediator server system 100, according to one of the embodiments, comprises the steps of using a mediation system 100 (referring to FIGS. 1 and 2) to enable or control mediation of information between a registrant 40 of some health-support service and a mediated party or EMR 14, with access to the BQR mediator. At runtime, the mediated EMR 14 communicates with the mediation system 100 via one or more data networks, such as a wireless network 24, with or without a landline network 22, or through a mediated EMR's communication device 18, which is typically but not always a wireless communication device (WCD) that operates compatibly with a BIIU device 19.

One preferred set of embodiments includes enrollment applications for a native health-support service in the specialized software, while another set is provisioned to interoperate with one or more distinct external enrollment services that are autonomous, but compatible. When both sources and destinations of information wish to protect their data, they may each choose to rely upon one or more mediators, and the rules that implement their specific policies.

For illumination we describe first the former set with an integrated enrollment module accessible by local method calls and describe the other kind of set of configurations later. The registrant 40 may communicate with the mediation system 100 via computer network 25 to enroll, register, or enable information sharing through a registrant communication terminal or device 16, or to transfer of representations of transformed biometric data or metadata, based upon sample data, captured using a biometric sensor or BIIU 19. The mediator software and hardware is of modest size and comprises data structures and processes, so that it can be easily adjusted to support the procedures, policies, or rules. These resources are interposed to control the mediated information flow between a registrant and an EMR. Rules in the software of a BQR Mediator may define the continuum of registrant-selected content release policies for sensitive personal information, at various privacy levels of granularity.

The operator of the mediator server controls certain policies on privacy and security. These policies may be implemented by rules and procedures, through interaction with, the BQR Mediator serving as a digital privacy officer. When the composition includes a native enrollment module, this privacy officer preferably delegates certain authority to registrants, to carefully calibrate the levels of privacy of different kinds of content for registering their own records, data, edits, or updates with one or more privacy constraints, and guides them apply privacy metadata depending on the confidentiality and granularity of their personal information. Databases and files within the domain can provide services and metadata to help manage the activities of the BQR Mediator, but otherwise cannot always be fully trusted.

As depicted in FIG. 1, communication associated with the registrant communication device 16 may be transmitted in a digital manner and communication associated with the mediated EMR communication device 18 may be transmitted also over a data communication system that is at least partially comprised of a wireless network. Accordingly, the registrant communication device 16 and the mediated EMR communication device 18 are ordinarily devices capable of receiving or sending (collectively "transmitting") information, data, or metadata in a data packet format, a standardized format, or another digital or mediator-compatible form. Mediated communications obviate any need for direct data communications between an EMR and a registrant by using specialized software, as described below.

Another optional aspect is that, to reinforce privacy or security, the BQR Mediator may use a separately or distinctly secured information storage unit for either each registrant or set of registrants (i.e., in a designated class, city, or participation level, etc.) Such units or databases should store metadata or data persistently, with the metadata or data also remaining network accessible by the BQR Mediator on a 24/7 basis.

The source of the biometric sample that is transformed at enrollment is also used to capture a biometric sample, for associated transformation, at query time. Generally, the same transformation process used for raw biometric data secured at or after a registrant's enrollment will be available for use at query time to replicate the metadata therefor, so as to more easily advance the analysis of at least two transformed versions of the biometric data. Using distributed computing techniques, such analysis may be performed at the server system or securely distributed for performance by using client programs, or other communicably connectable applications or components.

2.0 Structural and Functional Overview

A BQR Mediator comprises at least one processing unit, 26a at FIG. 2, or computer server system (hereinafter "mediator server") FIG. 1, at 10, to support specialized software, typically executed to resolve queries by linking data resources and application programs. By using problem-solving knowledge while normally operating unattended, the mediator 100 orchestrates processing across applications, base resources, or facilitators, as needed, to process any of a set of standardized requests or request forms. One of the BQR Mediator's functions is to provide integrated information, without the need to integrate the base data resources (i.e. files, metadata, transformed BCD, registrant specific identifiers (RSIs), rules, procedures, profiles, name, images, text, photographs, or other data, etc).

The processing unit 26a is typically a unit among a plurality of processing units that form a distributed system, comprising: information storage means for storing data, including without limit, storage allocable to transformed BCD matching templates, metadata, or other identifiers (e.g. vectors, strings, RSIs, UPIs, etc.) or files of registrants, or pointers thereto. The BQR Mediator usually processes each query to produce a result set. The result set may or may not be used to generate a biometric resolution response to the requester.

The specialized software of the BQR Mediator contains problem-solving knowledge that represents how a request from an EMR, which concerns a patient, may be processed as a query or resolved. Viewing the functions supported by the BQR Mediator, an EMR may use a WCD communicably connectable to a biometric sensor or biometric inputting information unit (BIIU 19), to either extract patient BCD, or transform BCD into a representation or metadata, and enable transmittal of the latter. The EMR's request may be transmitted on any conventional or proprietary access network, including without limit either a Wide Area Network 16 or a network partly comprised of a Wireless network 24, using the WAP protocol stack 15 and WML. The EMR may then rely upon using a secure channel of a network to communicate data with a BQR Mediator. The method contemplates that the BQR Mediator will, if not blocked by a rule, policy, or in some configurations human intervention, specify or retrieve one or more fields or files of information that may be private or confidential to the registrant. This means that the packaged private content should nearly always be accessible in some form, via a computer network communicably connectable to the BQR Mediator, to ensure that query processing is supportable on demand.

Figure 2:
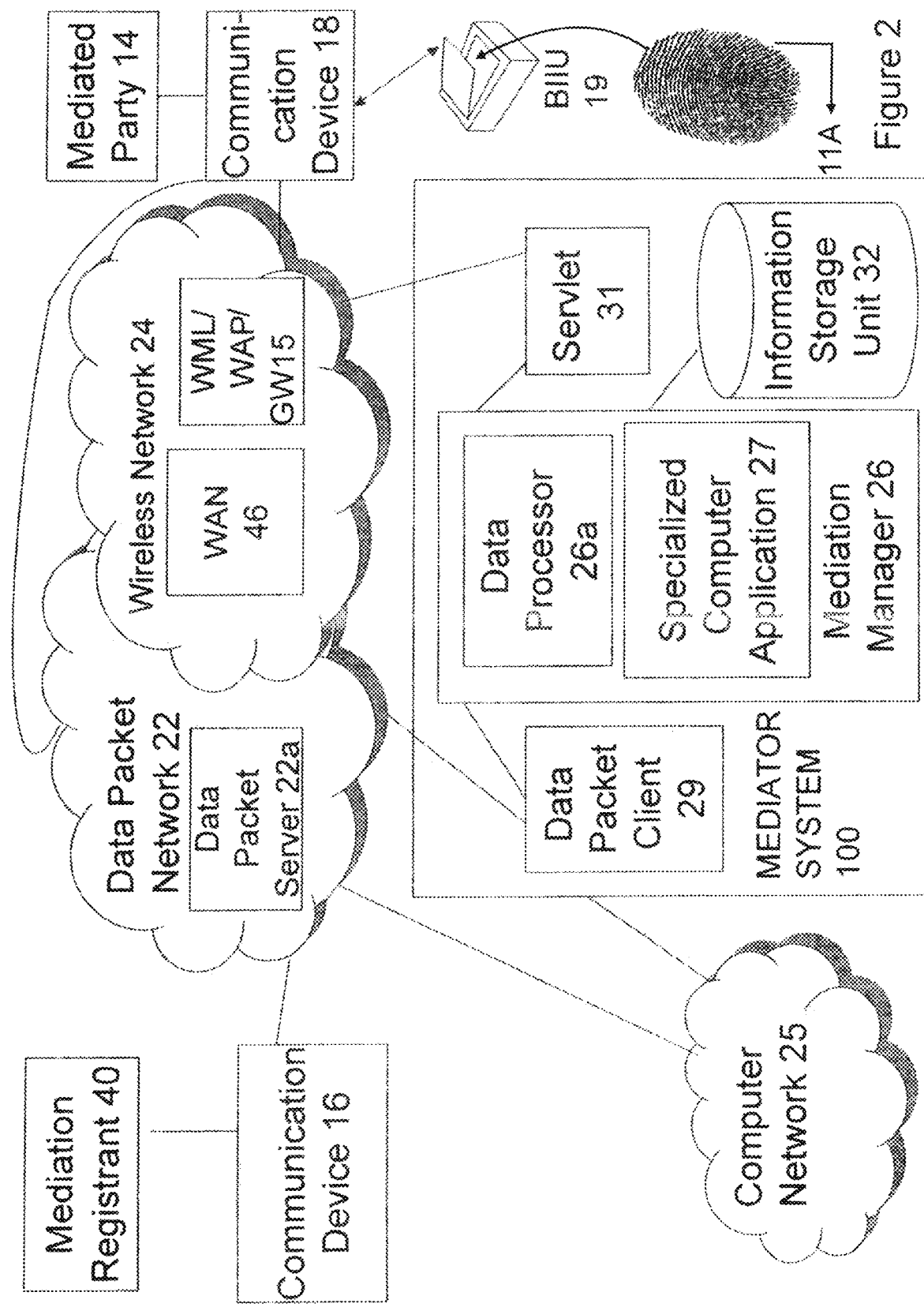
FIG. 2 is a block diagram depicting an embodiment of a mediator server system capable of facilitating mediated request-response messaging, or signal processing, via a data communication system, in accordance with an embodiment of the invention. It also refers to FIG. 11, below, that shows another example of how BCD-oriented input could be processed using a BIIU for biometric recognition and, like FIG. 2, transmitted through a gateway (GW) as needed.

As shown in FIGS. 1 and 2, to enable transmission, communication is established between the WCD used to initiate a request, and said BQR Mediator over a communications system or network, comprised, at least in part, of a wireless communication network. The mediation server is preferably configured with one or more processor, and with multilevel security, using a platform conducive to backup server capacity and other components to ensure network redundancy, including, without limit, an independent power supply.

Returning to FIG. 2, we introduced an embodiment of a mediation server system 100 for enabling mediation activities to be facilitated by the registrant communication device 16, and the mediated EMR communication device 18. As illustrated, a registrant communication device 16, mediated EMR communication device 18, registrant communication system 16, and service management system 23 are depicted as asynchronously communicating via a server system 100.

The mediation server system 100 includes a processing unit 26a, a data packet network 22, a wireless network 24, and a computer data network 25. The processing unit 26a is connected to the data packet network 22, to the wireless network 24 and to the computer data network 25, thus enabling communication therebetween. To enable enrollment, as may be required by a BQR Mediator operator, the computer network 25 is connected to a registrant computer system 16, to the mediation manager 26 and to a service management system 23 thus enabling communication therebetween, preferably with failure mode recovery capacity.

The processing unit 100 includes a mediation manager 26 with a data packet client 29, a wireless network protocol executable program or servlet 31, typically executed on an access server, discussed below, and an information storage device 32 connected thereto. The data packet network 22 includes a data packet server 22a that enables communication between the data packet network 22 and the data manager 26 via the data packet client 29.

The mediation manager 26 includes a data processor 26a, such as a computer server, processor-based system, network server, Unix server system, a workstation or other suitable type of data processing device. The computer interface (not shown) is connected between the data processor 26a and the computer network 25 for enabling communication therebetween. The information storage device 32 is connected to the data processor 26a for storing information in non-volatile memory and retrieving information therefrom. The mediation manager 26a may use the processing unit 100, or some CPU capacity of the processing unit 100, in place of any physically or logically separate data processor 26a. A specialized computer program 27 includes a computer program that is executable by the data processor 26a of the mediation manager 26. The computer program enables execution of at least a portion of the operations, including query mediation, performed by the processing unit 100 for accomplishing the methods disclosed herein. The computer program is accessible by the data processor 26a of the mediation manager 26 from an apparatus such as a non-volatile memory, diskette, a compact disk, a network storage device or other suitable apparatus. The specialized computer program 27 is a programmable application compatibly supported by an operating system of the data processor 26a that may be optimized, as needed. It may, for example, use a service bus in a distributed computing topography with one or more local method calls or interapplication processes to enable extracting data from a database or information storage unit 32.

Figure 3C:
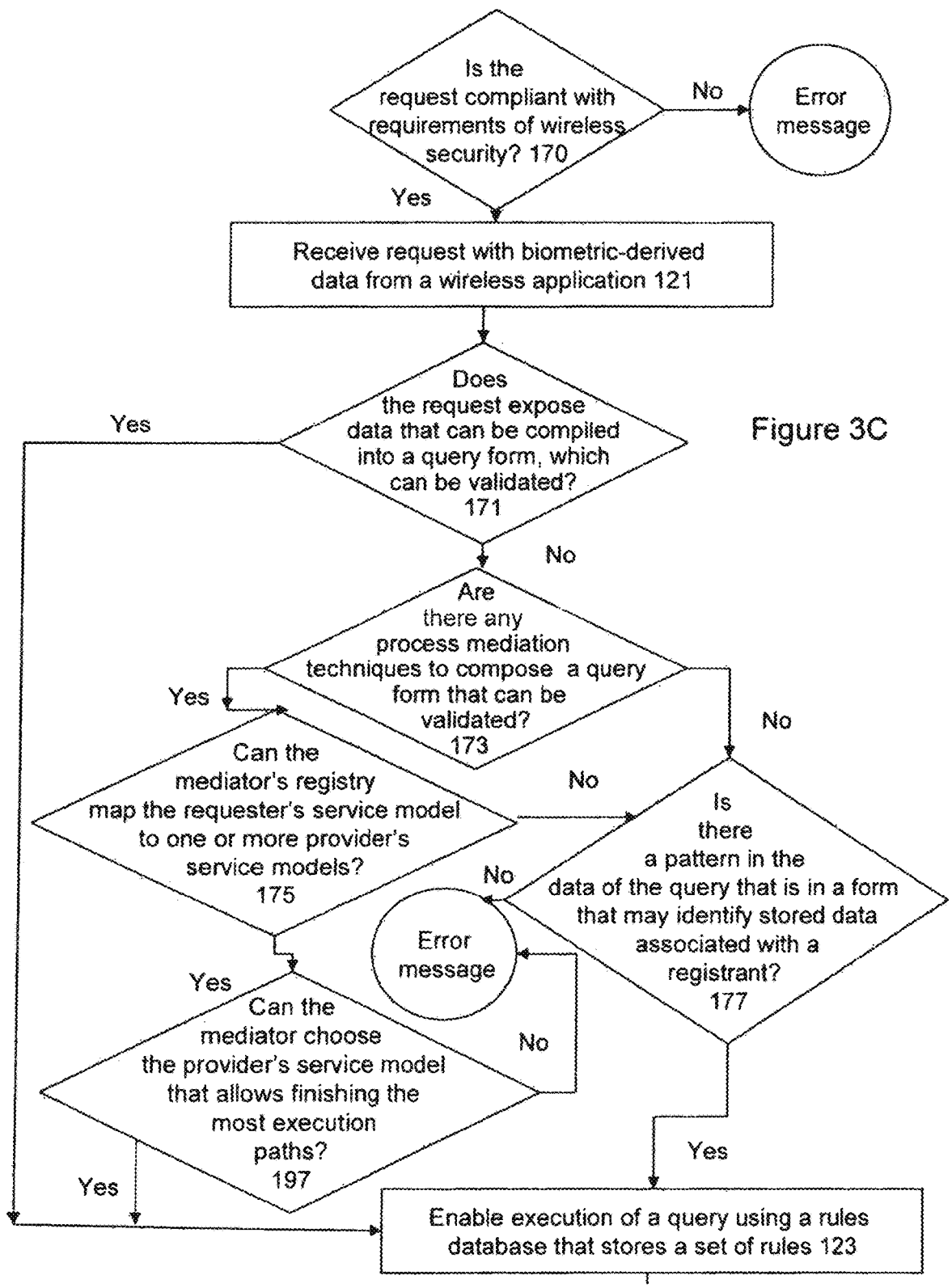
FIG. 3C is also a detailed flow diagram depicting a set of operational acts controlled by mediation software to permit cross-system retrieval of patient-specific data for identification or healthcare, or both, by process mediation across external resources based on any requestor's service model that may interoperate automatically with at least one external provider's service model, which is accessible to execute a query compatibly, unless it is inconsistent with any applicable interoperability rule, in accordance with a set of embodiments of the invention.

FIGS. 3A, 3B, and 3C depict a few of several alternative embodiments that may differ from one another. The artisan will appreciate that the order of the steps prior to enabling query for execution may be rearranged as needed into one or more other orders or combinations. Referring to FIG. 3A, a flow diagram depicts a certain set of operations or acts controlled by the mediation software or specialized computer program 27 of a BQR Mediator, in accordance with another alternative embodiment of the methods. In FIG. 3A, the specialized computer program of the BQR Mediator comprises instruction to perform the steps of: receiving a request 121 with biometric-derived data from an application of a mobile device, enabling execution of a query 123 using a rules database that stores a set of rules, executing the query 125 to process results by analyzing the occurrences of patterns using a biometric abstraction model compatible with the data of the query, and extracting data of an associated registrant from the information storage unit or database 127, as permitted by the rules. A BQR Mediator operator may provision one or more applications to at least support basic common operational specifications of a BQR Mediator, so as to enable generating a result set from the data conveyed by the request. The result set, albeit encrypted, is usually shared locally 129 with the server system. The result set may be comprised of either an encrypted file with a registrant's profile, an RSI, other identifying data, personal information, a biometric encryption template, ICE content, or other data. Some result sharing configurations may be provisioned configured to include biometric performance or network grade of service specifications as well.

Referring to FIG. 3B, a flow diagram depicts a certain set of operations or acts controlled by the mediation software or specialized computer program 27 of a BQR Mediator, in accordance with one embodiment of the methods. In FIG. 3B, the specialized computer program of the BQR Mediator comprises instructions to perform the steps of: determining 115 if the request was sent via a data network that was wireless in any part; determining 117 if the request was sent from an application, other than one invoked by the person who is the subject of the request; when at least one of the first two determinations are affirmative, receiving a request 121 with biometric-derived data from a wireless application; determining 119 if there a pattern in the data of the request that is in a form that may identify stored data associated with a registrant; and enabling execution of a query 123 using a rules database. Notably, here, the data may also be considered as sufficiently in a form that may identify stored data also, if it can be translated by the BQR Mediator into such a form automatically, without the attendance or assistance of a human at runtime.

The mediation software operates compatibly to process or analyze data gathered or secured using one or more biometric approaches, while controlling the server system's connectivity. A mediator operator may extend the BQR Mediator's network, realm, domain, or WLAN securely by integrating certain applications to harness a stack of conventional data communications protocols, with interrogation technologies or data extraction mechanisms that are suited to the form of the stored data or information that was registered. That stack that supports network applications or web services generally, also can support the biometric-related functions of the specialized software to transmit data over even a secure wireless network.

Query mediation may be advanced by equating, translating, approximating, harmonizing, as needed, the biometric abstraction models employed by the requesting application and the mediation server system. The "information hiding" property that typically emerges by coupling an identifier, like transformed biometrics, with mediation software and secure wireless messaging capabilities is notable whether an identifier is used to invoke a biometric encryption template from the server system to permit a client application to descramble a PIN, or whether the transformed biometric data is transmitted to the server system 100 for resolution. It distinctively enables a registrant to extend a limited level of consent for certain mobile EMRs to access or transfer personal content, so that the content may virtually or effectively follow or lead the registrant's person or body wirelessly across remote or local locations, as needed. The composition of the mediation method is made, conducive to use, or used in the context of resolution, via request-response messaging over data networks to mediate data, processes, or protocols as needed, to provide a result set.

The metadata is also entirely independent of the raw biometric sample, in the sense that metadata may never be used by an insider or outsider to derive the raw biometric sample or reconstruct any part of it. If the metadata were intercepted it would be irreversible. Even the mediator need not be granted access to the personal content other than as encrypted or in an oblique packaging, and encryption helps ensure consistency with the principle of least privilege to ensure privacy. Biometric encryption often may be preferred to permit recovery of a robust PIN remotely or "on the fly", particularly rapidly once the possible registrant has been identified. A mediator may be programmed to leverage the metadata that identifies the registrant's raw biometric data to descramble a registrant-specific identifier, secret code, or robust PIN, to attain a registrant's private key, and thereafter permit further processing of that registrant's private key to resolve the query.

A mediator may enable a qualified requester to leverage, associate, link, or match the transformation of the registrant's biometric samples, or sample sets (i.e. discretely scored, averaged, combined, or composited, etc.), from both of the request and enrollment timeframes. If enrollment program and interface instructions are integrated within a configuration of a BQR Mediator, the mediator operator also typically secures the registrant's consent to data collection, either expressly or impliedly. When the BQR Mediator has an enrollment module, it may distinguish between native biometric abstraction models and other compatible biometric abstraction models. Yet, in the context of a query for identification of someone who is not readily identifiable otherwise, for example, a deployment may perform better in many instances, if it processes a query by using one or more other operations that may narrow the field of potentially matching registrants first.

Some reductive programs or disambiguating operations permit the BQR Mediator to limit a candidate list. These logic layer programs initially may be invoked to associate, match, sort, classify, index, segment, or filter data or to execute one or more other operations or programs (i.e. either separately, sequentially, concurrently, or iteratively, etc.). By orchestrating one or more of these reductive applications at the BQR Mediator, the mediation process may be designed to generate a result set (i.e., by using an Identification to PHR instruction set with analytic programming, etc.) within an acceptable confidence level or grade of service, risk free of reconstruction. Some configurations can optionally rank candidates, compile other comparisons, conduct multivariate analyses, or reveal statistics or use probabilities at query resolution time.

Some configurations may deploy conventional databases, registries, or directories as components to manage storage, while others may use different information storage units 32 or customized data management systems. Preferably, the BQR Mediator communicates with a database and processes toward resolution or authorization, in view of privacy rules, after preprocessing of one or more sub-routines. In some configurations, before or during query runtime, the BQR Mediator processes an authentication assertion reflective of its scrutiny on the qualifications of the originator of a request. This authentication process, if during pre-processing, for example, may pivot upon an affirming of privilege level by using one or more key infrastructure processes (i.e. public key encryption, public key infrastructure, techniques using base pairs, etc.), or other cryptographic routines that grant access or clearance to an EMR, an eligible wireless device, or both. It may (i) yield a privacy token to calibrate the EMR's privilege to accessible data or (ii) enable the processors to detect, format, parse, convert, or process data of a request as a well-formed query, or (iii) both.

During either pre-processing or processing, the BQR Mediator typically uses an access server system running a servlet to handle the query and control resolution of data of a query, so as to indicate the putative registrant's participation by associating or matching a person's biometric metadata, or, by verifying, if available, the person's name or other registrant-specific identifier. If the person is registered and there is no false rejection, an affirmative result set can reflect an associated or matching profile, if any exists, compliant with the registrant's self-designated privacy constraints.

The query resolution operation alternatively may be designed to execute at query runtime by processing an express or implicit registrant identifier that is secure, like a private key, derived with or without biometric oriented input. A BQR Mediator may consolidate the private key of the registrant together with an EMR's privacy token, to produce an authorized result set. It may include, for instance, a pointer to a privacy-delimited profile in encrypted format. Notably, other deployments of the methods may obviate enabling any authentication process when verification or associated profile data is merely sought on a registrant, who declined to impose or utilize rules that raise any privacy constraints. Upon processing to produce such a result set, any further or additional post-processing (i.e. to enable processing results further, response packaging, transmitting, sending, or sharing, etc.) is optional.

In contrast to the examples above, a configuration could instead more closely follow one of the leading security paradigms that routinely defer clearance of privacy rules (authorization) to a post-processing phase. This sequence usually, but not necessarily, begins by preprocessing to authenticate the request. An authentication module may, for instance, simply extract that relevant data from message header sequences to issue or log an authentication certificate. If the EMR's request is authenticated, the BQR Mediator's processing may proceed to resolve a query to find a registrant's profile. By communicating with the database, the mediator server can run one or more operations, for example, to look up a name, associate a registrant-specific identifier, match transformed biometric data, process a private key, or match metadata from both timeframes. Some configurations may find a registrant's biometric encryption template, using one of several biometric encryption approaches. Upon processing that uses one or more of these approaches, an EMR, by unscrambling a code or robust PIN from a registrant's biometric encryption template that the BQR Mediator has sent him, may attain the registrant's private key. To ensure against over-inclusive disclosure of personal information of a result coupled in a response to the requesting application, however, further post-processing for authorization may proceed to exclude, omit, excise, or redact any sensitive private data therein. The scope of the content in the result set may be restricted by any privacy restraints such as ones calibrated to the EMR's authentication token or privilege level, to compile the properly authorized result set with variable granularity (i.e. document, field, data element, photograph, etc.).

Alternatively, various implementations may deploy "best of breed" identification or verification techniques that galvanize biometrics and computation, at least in part, such as ones relying upon any of several biometric modalities, one or more analytic techniques suitable for a single biometric source, some combination of biometric sources, cancelable biometrics, biometric encryption, combinations of biometric and non-biometric modalities, or other methods either known or suggested to the artisan of ordinary skill. The methods also concern how to develop or use an application that advances the query resolution using biometrics in this context, whether or not that application also natively supports a phase of enrollment.

Some embodiments may be provisioned to advance process mediation that maps or translates the challenge of handling a remote request to utilize one or more external provider's service models, if the query cannot be resolved by the local provider's service model. To that end, there is often a process invoked to cross-verify compliance with security and privacy policies between correspondent server domains, as well as to align message flow patterns and terminologies for process mediation. Another alternative embodiment, as depicted in the flow chart at FIG. 3C, elaborates upon one of several possible variations of the protocol in FIG. 3A above, with process mediation across external resources. If the request is compliant with requirements of wireless security 170, the BQR Mediator receives the request 121 with biometric-derived data from a wireless application. Thereafter, the BQR Mediator's servlet examines if the request exposes data that can be compiled into a query form, which can be validated 171. If so, the specialized software can enable execution of a query using a rules database that stores a set of rules 123. If not, however, some configurations of the BQR Mediator may be provisioned to seek assistance from external services or correspondent databases to get to the stage of enabling query execution by further preprocessing.

The specialized software can inquire if there are any process mediation techniques 173 to compose a query form that can be validated, If so, the specialized software determines if the mediator's registry can map 175 the requester's service model to at least one provider's service models. If so, the software is designed to choose the one that allows finishing 197 the most execution paths, if possible. If there are not one or more provider's service models, however, the specialized software may examine the query at the data level to analyze if there is a pattern in the data of the query that is in a form that may identify stored data associated with a registrant 177. If either of the last two questions at 197 or 177 above is answered yes, then the BQR Mediator may enable the execution of a query, using a rules database that stores a set of rules 123. If, instead, there were no ability to choose the provider's service model that allows finishing the most paths, and no adequate pattern discerned in the data of the query, then the preprocessing phase could end (i.e., by error message, or notice, etc.). These configurations can interoperate to reduce serious or deadly risks of health care errors or misidentifications, which may otherwise result from mismatches on a conceptual or semantic level.

The methods may, in all events, enable mediator operators to improve privacy, consensual disclosures and uses, diagnosis, treatment, routing, or notification, irrespective of the chosen biometric technique or service model deployed by the mediator operator alone. As to a wide of an array of distinct configurations, many of these functionalities are also compatible with the possibly combined use with either smart cards, other conventional ICE methods, or health record consolidation services, or some combination thereof. Indeed, usually, an EMR may more rapidly verify an identifiable person who bears a smart card or device, for example, since a card or device may indicate participation immediately and render a bearer's robust PIN directly accessible. Other conventional non-biometric or biometric methods also may be complemented rewardingly with one or more of the present biometric mediation methods, especially as a safety net. This kind of integration, backward compatibility, polymorphic adaptability, or extensibility, can be beneficial, even to registrants who ordinarily maintain their wallets, identity cards, smart cards, or mobile phones accessibly in tact, to provide an extra level of insurance that their data is nearly always accessible with redundancy, even when conventional identification cards or devices unexpectedly become inaccessible.

Typically, there can be translation or mappings between the mediator handling the query and the external service providing access to enrolled data. These mappings typically will need to extend beyond the external service's recognition that the BQR Mediator may serve as a proxy for the registrant of the external service, to access personal information, through some indicia of consent (i.e. transfer of metadata of biometric sample, etc.). Further measures orchestrated through process mediation may need to resolve or avert potential mismatches in requester service models, provider. service models, biometric abstraction models, privacy rules, security safeguards, and other possible disparities. Most commonly processes are specified by means of their inputs, outputs, preconditions, and effects (IOPE). The inputs and outputs are usually defined in concepts in some ontology. Process mediation may require translations or mappings to reconcile mismatches between the requester model and the server provider's model. It may entail coupling two distinct expectations of message flow patterns under two models or entail a harmonization of ontologies or model semantics. Beside control-flow, the process model also specifies a data flow between processes. As the artisan will appreciate there are numerous variants of other techniques of process mediation that range from adaptations to syntax, to message flow, or to protocols, or some combination.

The BQR Mediator's service bus may be designed to employ a connectivity layer to ensure compatibility with the selected Mobility Network platform that is commercially available, provided it adheres to security specifications at least as strong as WPA-2/802.11i standards. Notably, Cisco's Mobile Service Management Engine (i.e. 3300) may transform a Wireless LAN into one example of several Mobility Network solutions, while supporting an Open API based on XML, REST (Representational state transfer), or SOAP (Simple Object Access Protocol) for third party application development. Like Cisco's platforms, other vendors' platforms also provide solutions to provision hardware with software to support RF Monitoring and Spectrum Intelligence, that permits a Security Officer to remotely supervise interworking across locations or nodes of the network or apply software or spectrum intelligence infrastructure. The latter may be used to automatically mitigate channel interference, assist in least-impaired channel selection, utilize white space, or apply dynamic frequency selection, including forming new channels known as Software Defined Radio. The BQR Mediator may deploy customized software, either using Cisco's platform or a conventional or customized substitute therefor, that is also compatible with WPA-2/802.11i. The BQR Mediator's control over request-response messaging may be customized using proprietary techniques or based on standards such as messaging conventions commonly used with XML, WML, or SOAP, and Query Application Programming Interfaces (Query APIs).

3.0 Specialized Software Overview—Some Implementation Approaches

Different Specialized Software Applications for Different Kinds of Query Resolution The methods of mediation to enable remote health care support have the versatility to optimize query resolution securely, even if the network is partly wireless, using identification or verification techniques, or both. Different conventional software applications, distributed computing configurations, biometric abstraction models, and sets of ancillary resources may be composed to limit functionality, in some cases but not others, often depending upon how they are provisioned to advance different purposes or goals for each BQR Mediator operator. By combining mediation software, biometric abstraction processes, and wireless communications for either query, source, biometric, process, or connectivity mediation, the BQR Mediator is enabled to resolve a query into a unified result set. At a basic level, three of the main kinds of methods using BQR Mediators may be described as follows:

(1) a method using BQR Mediator that may be dedicated to enable resolution, at a verification phase, of only queries for registrant-specific content, like profiles;
(2) a method using a BQR Mediator that may be dedicated to enable resolution of only identification queries; or
(3) a method using a BQR Mediator, alternatively, that may be provisioned to enable resolution of either identification queries or verification queries, or both, as needed.

Each kind may be provisioned using specialized software customized to fit its purpose. There is, for instance, usually a greater impetus for mediator operators to configure a BQR Mediator with ancillary configurations that comprise a native or integrated biometric enrollment module under the second case than in the first case. The pure verification mediator, described first above, is a relatively straightforward software-aided operation, as it may readily leverage other enrollment services by using well-tested 1:1 techniques. Commonly, the query is accompanied either with BCD metadata or another compliant identifier to retrieve a biometric encryption template. This subset of configurations, when aimed toward improving ease of use, often utilizes a database to process or match the input with the data stored for the already tentatively identified or known registrant being verified, so as to generate an unified result set. When such specialized software uses the database to yield an output or result comprised of a biometric encryption template, which template is information that is specific to a registrant, who is also the individual to whom the abstracted biometric data of the query pertains, the specialized software may do so by utilizing a computer program mechanism that also comprises instruction to enable securely transmitting a response to the request. The response simply conveys the said result with the template, back to the source of said request under the mediation procedures.

Under pure verification operations, some configurations may perform verification based upon a registrant's key, irreversibly derived from a registrant's biometric sample. These may or may not support a method of privately and securely mediating an automated response coupled with a result from a BQR Mediator to an EMR's request. Ones provisioned to automate such a response, without reliance upon a Certificate Authority, for example, commonly employ steps, comprising: i) validating the EMR's request once the request indicates that the EMR has used a biometric sensor to generate a key for the registrant, and has securely sent said registrant's key within the request to the BQR Mediator under the BQR Mediator's public key; ii) applying the BQR Mediator's private key to utilize said registrant's key to verify the registrant's identity and to encrypt the personal content of the BQR Mediator's response; iii) transmitting to the EMR under the EMR's public key the encrypted content of said response, and iv) enabling the EMR to apply the EMR's private key to access the message containing the encrypted content and to utilize said biometric sensor on the registrant to decrypt said encrypted content of the response. Under another approach the BQR Mediator uses Biometric Encryption by sending the EMR a biometric encryption template for the registrant being verified, and permits the EMR to generate the Registrant's PIN. A decryption procedure may be based either on an extension of two-party key encryption conventions or trusted third-part ones, as in an extended PKI manner, for EMRs, akin to Alice's reliance upon Trent in the Biometric Encryption scenario cited in the Background.

Under the second category of pure identification, the data of the request may be used as a query that a BQR Mediator recognizes as likely to require one or more applications that perform identifying processing or classifications. The query can be normalized for navigation or serialized to discern its identifying requirements in the logic layer of the BQR Mediator, which marshals instructions that enable the requisite analysis or classification to be conducted. Many have learned that the multiple applications may be used to divide and conquer the task expediently, with reduced risk of errors. For example, the specialized software could use minutia of a right thumbprint for identification to produce a shortened list of possible registrants, and a secondary set of one or more applications that may process the right thumbprint of each registrant against another distinct set of indexed characteristics of the thumbprint (i.e. using control points, gray scale data, etc.). A BQR Mediator may often advance segmentation to perform identification by using certain disambiguating instruction code of one or more approaches. In turn, when the transformed data on such minutia is associated with a stored record for a registrant, the BQR Mediator that generated the unified result set, may be provisioned to send to the EMR the biometric encryption template that corresponds to the best matching registrant's data, so as to enable the EMR to further confirm of identity. See also, infra, at ¶¶66-67.

To anticipate a class of queries or events where the request indicates that a registrant is not identifiable but needs to be identified, many deployments (FIGS. 2, 3A/B, and 4) can invoke a workflow controller 83 via a mediator services manager 26 to instantiate logic layer programs 132, which may use classification, indexing, segmentation, filtering, sorting, or other modules or applications that permit a constant narrowing to the most likely candidate. ("reductive applications"). These reductive approaches may include multimodal biometric ones also if the latter are in complicity with enrollment data. These techniques are especially effective to improve scalability of many, but not all, configurations to reduce the universe of registrants to a more limited candidate list. They may also reduce the rejection rate, especially when an application or filter executes identification in a single operation, but otherwise only yields a sufficiently high level of accuracy in matching with an undesirably high rejection rate.

Computation may be designated as primary, secondary, or tertiary applications of the logic layer of the mediation domain, in accordance with different embodiments. When a logic layer is invoked it may use one or more applications, for instance, in resolving a request for a profile of an unidentifiable person who may be a registrant. At a lower level, though, the logic layer may be implicit or explicit, depending upon whether there is any need to process or parse EMR requests for identification differently from requests for profiles via verification.

Thus, for such post-enrollment registrant identification, the BQR Mediator within this subset of configurations, will operate to reduce the universe of candidate registrants using reductive applications, as needed, preferably by beginning with the most effective classification, indexing, segmentation or other reductive applications provisioned thereon, which correspond to the one or more biometric sources being scrutinized, and more subtly, will continue to do so, either iteratively, sequentially, or concurrently by applying distinct applications (i.e. secondary, tertiary modules, etc.) timely. By compounding distinct indexing techniques, for instance, with low correlations in error, inter se, certain higher confidence levels may be achieved due to improved accuracy rates. Many fingerprint indexing techniques, for example, rely upon minutia (i.e. configurations, measurements, three point sets, etc.), since linear transformations between scans can require surmounting hurdles of rotation, translation, scaling, shear or other noise (i.e. due to elasticity of the skin, variances in pressure, finger dryness, and sensor capacity.) Some reductive applications can surmount the common hurdles of image comparisons using continuous classifications, fixed radius techniques, compositing, parameterization, or reference models. To adhere to the principle for risk free of reconstruction, the BQR Mediator's server system deploys reductive applications that process transformed biometric data or representations, which are irreversible.

To resolve queries arising from EMR requests for identification while reducing rejection rates, one subset of configurations may use registrant volume and other parameters, for instance, to set the minimum number of reductive applications needed to optimize the likelihood of successful processing of a result set. They may be made to automatically deploy one or more of these reductive applications separately, serially, sequentially, iteratively, recursively, or via parallel computing, as needed. To this end, such a query resolution will typically use no greater number of reductive applications, or instances thereof, than are necessary to optimize BQR Mediator performance, in view of predictive statistics of each reductive application, which are used. In contrast to identification requests, when stand-alone verification requests are processed using these configurations with blocking methods, such ancillary reductive applications or modules are often extraneous. Accordingly, neither any classification nor any indexing techniques are usually used to support query resolution that arises from a pure verification request, which merely seek to link a registrant's known identity with his or her profile by using transformed BCD or metadata, when more streamlined instructions can do so in a timely manner without them.

Some mediator operators, however, may meet a broader set of goals by configuring a method using a BQR Mediator, with specialized software, which, alternatively, may be provisioned, to enable resolution of either identification queries or verification queries, or both, as needed. The BQR Mediator preferably is organized in tiers that permit safe programming principles and offer conceptual clarity of the functions of each tier and the interactions therebetween. Referring to FIG. 4, the specialized software running on one or more processing units enables data transfers, local method calls, or messaging of the mediation domain, through the stack of layers, comprising: (1) a Presentation and Composite Application Layer 130; (2) a Logic Layer Applications Layer 132; and (3) a Connectivity Layer 134. Under this framework, the specialized software supports query resolution by using a Service Bus 41 to process and transport data, control web services, or constrain information sharing, as needed. The framework permits data flows between any layers to advance source mediation, query mediation, process mediation, or secure network connectivity mediation, as needed.

The BQR Mediator's software may encompass one or more logic layer applications 132 that use instructions, processes, or procedures to assist in navigating the resources of the mediation domain most effectively via the Service Bus for each kind of request, whether it is for identification, verification, or both. For instance, some BQR Mediators may be configured using a logic layer to effectuate 1:N processing, until the discovery process has advanced so that 1:1 processing is no longer likely to remain suboptimal, impractical, or premature. The composition of the BQR Mediator may be agnostic to storage techniques for persistence of data. The resolution server 87 can thereby retrieve responsive data from each of the appropriate databases 32 and return such associated data to a servlet 31 as an output or result set. As with conventional databases, association of certain data may be accomplished through any data association technique known and practiced in the art. For example, the association may be accomplished automatically. In one embodiment, the servlet 31 may invoke a resolution module to run a resolution application, which receives a remote request, marshals abstracted biometric data of an individual indicative of said request to pose a biometric resolution query to a database module capable of dynamically invoking a biometric data abstraction service module to process certain data indicative of the resolution request, and produce a result set to said query. A resolution module of a BQR Mediator may be provisioned to perform abstraction to bring materials to matching levels, integrate material from diverse source domains, assess the quality of materials from diverse sources, rank in terms of quality or relevance materials from diverse sources, or adapt to the bandwidth or session management requirements of requesting applications.

The artisan in the field appreciates that there are many applications that involve numerous, though perhaps not infinite, techniques to classify, index, segment, or compare either salient characteristics, distinctive qualities, quantized parameters, or observable variations, measurements, or transformations. Some deploy image analytic approaches, while for certain biometric techniques the approaches are not dependent upon image analyses. These applications may rely upon different processes or mechanisms of database extraction as well, since those with dependencies on image analytics may not be suitable, much less ideal, for those that neither use image analytics nor transform image data, for example, into vectors, source code, strings, or numerical data. The logic layer, and certain adjacent layers thereto, which extensibly support such applications or modules, are highly adaptive at design time or runtime, and the logic layer may encapsulate different classes of applications with polymorphism.

Such biometric query resolution techniques may be driven by biometric data with or without other data. Some of these techniques using other data, for instance, may rely upon one or more other physical, but non-biometric variables, class identifiers, or filters (i.e., gender, race, eye-color, other discernable genetic sites of common variation of the human genome, or traits, etc.). Some of the configurations that rely upon biometric capture, processing, and association may be provisioned so that a result set includes a response containing not only a registrant's profile, but also a response that makes conspicuously available any advanced directive as part of a result set, which is further coupled and packaged in a response, to convey verified personal health information with the registrant's personalized directives as well. Once a complete result set is received, the mediator 100, in one embodiment, will package the result set as an encrypted response and transmit it as a message to the requesting client. Thus, in some embodiments not only may the mediator 100 act as a conduit between two systems when one is no longer operating at mediation runtime, it may also facilitate response messaging with the one running, for responsive completion of remote requests.

Together with tiered facilities for a workflow controller, described below, and service composing, the logic layer can marshal the instructions, operations, and resources that correspond to the task posed by the query. Referring to FIG. 4, the logic layer, for example, may run a query from a request through a virtual processing turnstile for a query-specific result set. The virtual processing turnstile, that controls the progression of preprocessing to any post processing, depends on another basic choice in the composition of the mediator. Some may be designed to dynamically discover an open number of provider service models, or an open number of requester service models. In contrast, they may be delimited to a closed number of compatible models. Thus, the chosen composition may be designed to handle requester's service models in an open or closed manner, and to handle the provider's service models in an open or closed manner. The combinations are open-open, open-closed, closed-open, and closed-closed.

One embodiment deploys the Service Bus, depicted in FIG. 4, and may use a multi-layered framework to operate the mediation processes and govern the data flow patterns that render internal and external services. The schema-driven user interface, which comprises part of the BQR Mediator's composite application layer, for instance, typically can be harnessed by the access server, described below, because it helps to validate, reformulate, or redirect queries, or to identify a request as a high risk channel flow request or a low risk channel flow request based on the nature of the remote wireless request. It may also help detect if the origination of request is over a WLAN circuit, VPN channel, an OpenVPN facility, or IP network with IPsec or UMLsec, a UDP layer with RADIUS and WPA-2/802.11i, or a TCP layer with DIAMETER, etc.. In the present example, the request is assigned to a high risk channel that is monitored for security and failover mode recovery to enable a resumption of the session, or a swap to another network channel, as needed.

Figure 5:
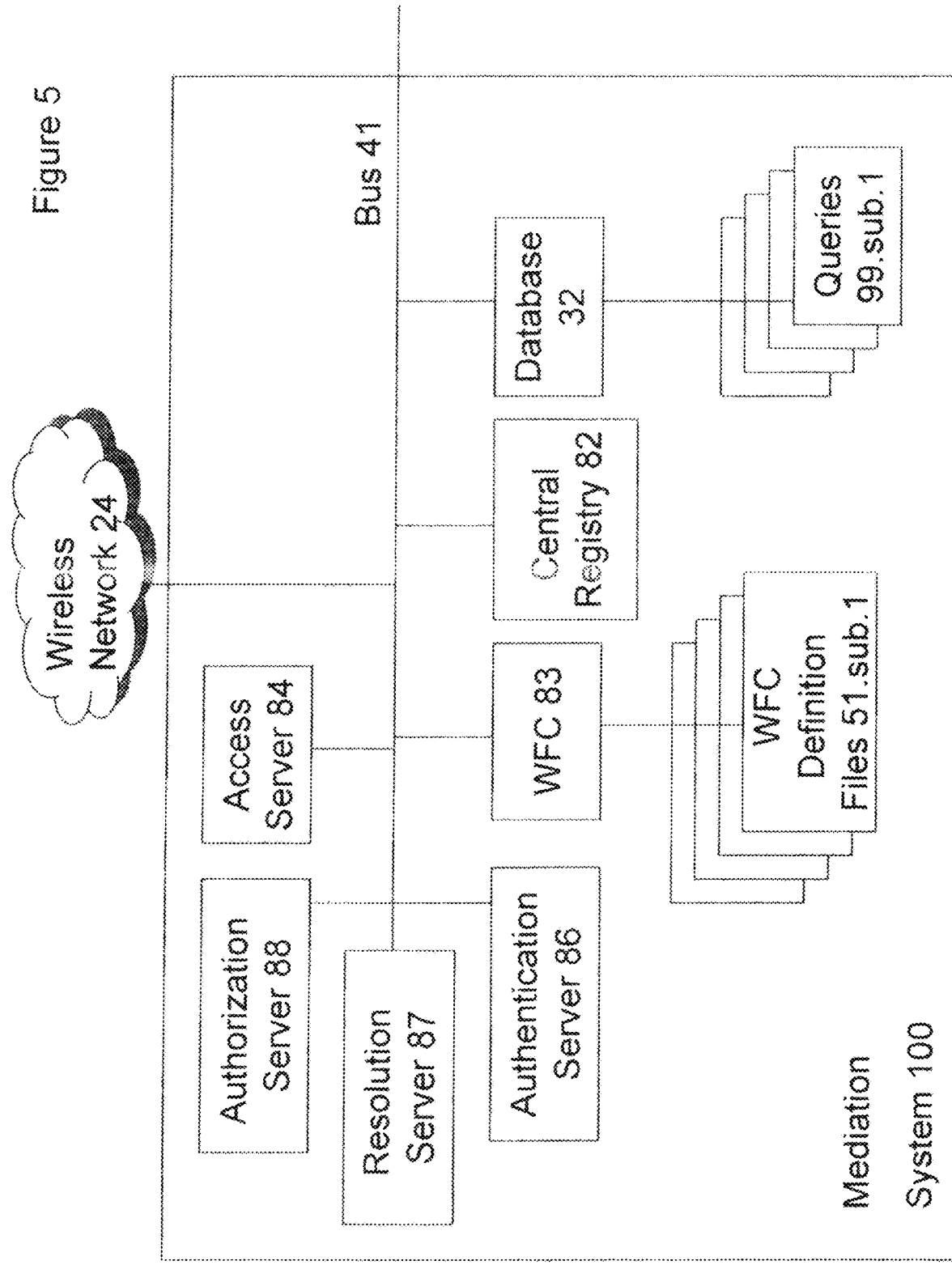
FIG. 5 is block diagram of a mediating server system with a service bus, which may be secured by a firewall but communicably connected to a network, in accordance with an alternative embodiment of the invention.

An Alternative Embodiment that Extends Query Resolution with Optional Dependencies of Authentication and Authorization Referring to FIG. 5, the processing unit 26a, is depicted instead within one embodiment as a mediating server system communicably connected with a service bus. The mediator server 100 at FIG. 1 may rely upon a service bus 41 in communication with the wireless data communications network 24 or data packet network 22 (see FIG. 2) and the services 40.sub.1. The services 40.sub.1 may advance, for instance, without limit, either request-response messaging, remote procedural calls (RPCs), WML-RPC exchanges, other data flows, local method calls, messaging patterns, or signaling, or even internal simulations of request-response messages services for testing. While all servers and databases could be consolidated in the mediation server, the service bus 41 is conducive to deploying the mediation method with components handling a division of labor. Coupled to the service bus 41 are a central registry 82, workflow controller 83, an access server 84, registration server 85 (not shown, since collocated with database), authentication server 86, resolution server 87, authorization server 88, and database 32. In this configuration, the database 32 may store one or more specific workflow definition files 51.sub.1. The mediator server 100 may control one or more of the workflow definition files 51.sub.1. The workflow definition files 51.sub.1 may specify the various tasks and sub-tasks needed to implement a workflow, such as by executing operations or deploying graph theory, node trees, or acyclic directed graphs, as needed, in order to rapidly complete the query. The workflow controller 83 may use one or more facilitators or agents 62.sub.i to control processes on the service bus 41.

Referring to FIG. 4, the BQR Mediator's service bus may process instructions, rules, or policies, using mediator data structures 101, a library of mediator procedures of privacy 102A, or a library of mediator procedures of wireless security 102B (FIGS. 6A, 6B, and 6C). In an alternative embodiment, as the request is received by the BQR Mediator 100 the servlet 31, enables processing of the data of the message body with attachments of the request, if any, as a query that is validated by the mediation manager 26, by using a service bus 41 to transport local method calls, under appropriate query processing rules and BCD matching rules that comprise a set of mediation data structures 101. The transformed biometric data used in the query is recognized if it is in a form compatible with the BQR Mediator's accessible registered conventions of biometric abstracted models, deployed by the subject implementation. Upon searching the central registry 82 to find the precise biometric abstraction model from an ontology, which registry catalogues the compliant biometric abstraction models, the BQR Mediator may perform a phase of operations to conduct query execution. If the ontology includes an entry that corresponds to the form of the transformed biometric data in the query, the mediation manager 26, central registry 82, and workflow controller 83 may enable query execution and invoke database access for extraction of data associated with the registrant-specific data in the query.

By enabling access to the proper databases using the right biometric abstraction model, related terms, and database tables, the desired data extraction by a query may be performed without searching extraneous files or database resources. The query may be executed as the workflow controller 83 prompts resolution server 87 using interapplication communications to advance extracting associated data, using a database extraction mechanism. That resolution server typically uses conventional techniques or an intangible instruction set as a database extraction mechanism, which is anticipatorily suited to, or corresponds with, the compatible model of abstracted biometric data. Under the biometric matching rules for that proper model, such as abstractions using a specific form of metadata or algorithm of transformed biometrics, the database is searched for entries to extract registrant-specific data from the database that is associated with the query data. It reliably directs the extraction operation or challenge task through one or more targeted databases 32, and in the case of metadata in certain forms, for instance, may do so using an SQL query or another common automatic association technique. Referring to FIGS. 2 and 4, the mediation manager 26, WFC 83, and workflow files 51.sub.1 may aid in the search by resolution server 87. The resolution server may rely upon the use of database tables or lookup tables stored in database 32, which corresponds to the abstracted biometric data of the query, to control the databases extraction process, and use mediation data structures 101, as needed. Automatic association techniques, which may be compatible with a BQR Mediator, include, for example, a database search, a database merge, GREP, AGREP, SQL, and/or the like.

In one embodiment, the WFC 83 may use a node tree, to ensure that many output resources of the individual nodes serve as input resources for other nodes. These other nodes may not be able to begin executing until some or all input resources are complete and available, which means that the nodes may need to execute according to a set of rules such that some tasks and sub-tasks in the query processing pipeline (i.e. preprocessing to processing, etc.) are preferably executed in a well-defined sequence or phases under logic layer 132 instructions, but not necessarily a uniform pre-defined sequence rigidly applied in every implementation. Many systems employ separate processing stages. See, e.g., Stubler, U.S. Pat. No. 7,228,006, Method and system for detecting a geometrically transformed copy of an image (Jun. 5, 2007). In the hierarchical organization of the node tree, nodes that occur higher in the node tree represent higher-level, more abstract operations, while lower order nodes represent more detailed, specific processes.

In determining which of the services 40.sub.i to assign to complete a particular query, the workflow controller 83 may poll services 40.sub.i that are coupled to the mediator server 100. As noted above, the services 40.sub.i may be coupled directly to the service bus 41, or may be coupled indirectly through another communications bus, such as a VPN, WLAN, or the Internet, for example. The polling may occur whenever a workflow definition files 51.sub.i is created at the mediator server 100. Alternatively, the polling and corresponding database extraction for information collection may occur on a periodic basis, and the workflow controller 83 may store information related to the services 40.sub.i.

Referring to FIG. 5, the workflow controller 83 (WFC 83), may operate in tandem with a resolution server and a service bus generally, to enable leveraging the biometric data as a link to a registrant's personal information by using any number of processes or techniques. Usually these processes or techniques will be selected for their functions, but the design choices of the mediator operator will routinely take into account how an anticipated sequence of request-response messages will help guide the choice of data structures that need to be implemented to support the functions, and thus, may influence the selection of processes or techniques provisioned as a foundation for mediation. Some of the processes and techniques deployed rely at runtime upon workflow definition files 51.sub.i and services 40.sub.i. Several variations may be deployed as well to resolve a query for verification or to process an identification query.

At runtime, the services 40.sub.i advance certain objects of mediation as to some embodiments that support the remote portability of personal data in result sets by enabling the BQR Mediator to orchestrate services, consistent with the WFC 83, and the software comprising the service bus. The services may include ones to advance identification or verification by using web services, by permitting processing on the side of the network with the server system or by sending client programs to a WCD, to facilitate transformation, classification, segmentation, indexing, or verification. These services may further select among applications or functionalities that use base resources and programs, including reductive applications that may zero-in on a registrant, as needed. Sometimes those processes that are to be run, or operations that are to be performed, may expedite analyses, prioritize acts, or optimize resolution of a query. Compounded reductive applications can be especially powerful to attain a result set within a configuration's performance specifications, time constraints, or other grade of service parameters or thresholds.

In determining which of the services 40.sub.i to assign to a specific task or sub-task, the workflow controller 83 may consult the central registry 82. Referring to FIG. 5, the diagram shows an embodiment of the registry 82. The registry 82 may be a data storage device or medium accessible by the services 40.sub.i. The services 40.sub.i may register service information with the registry 82 according to a pre-defined format. The workflow controller 83 may then access the service information to assign services to the tasks and sub-tasks that define a particular workflow. When assigning a service 40.sub.i to a task or sub-task, the workflow controller 83 may take into account conditions existing at the completion of a prior task or sub-task. In one embodiment, for instance, the workflow controller 83 and the registry 82, will streamline the resolution of requests directed to find a registrant's profile, when the registrant's identification is known, and may be verified using a biometric encryption template, as a condition to resolving an associated query into a result set that specifies the registrant's profile.

Using one alternative, biometric metadata may be matched by combining the use of (i) metadata based upon the transformation of a live sample of biometric data at query time with (ii) indexing or classification techniques. Some of these known processes or techniques, include ones such as relying upon: any of several biometric modalities; one or more analytic techniques suitable for a single biometric source; a compound segmentation process using some number of algorithms based upon serial or parallel processing using different biometric patterns or minutia; some combination of biometric sources (i.e. which may include, without limit either fingerprints, iris data, hand configurations, etc.); cancelable biometrics; biometric encryption; combinations of biometric and non-biometric modalities; a welter of cryptographic or network standards; spectrum management policies or regulations, or other combinations thereof or methods either known or suggested by their class, function, or purpose to the artisan of ordinary skill.

In another alternative to that optional provider workflow sequence, for instance, the resolution server may conduct a provisional assessment of likely matches using other classification, indexing, or disambiguating methods to cull a candidate list of registrants for further 1:1 verification processing, whenever more than one possible registrant is preliminarily indicated as within a subset as a possible match. It may resolve to output a registrant identifier on the hypotheses that verification of one of the registrants will be attained if appropriate upon testing of a narrowed list of registrants. Classification, indexing, or disambiguation techniques may rapidly advance processing toward a result set that isolates a registrant-specific identifier associated with a transformation of a "live" biometric sample.

The mediator operator may exercise several deployment choices that include, for instance, which biometric modality and technology to select or deploy, which image analysis or other quantitative analytic technique(s) to apply or translate into machine-readable instructions, and which network security configuration to implement. As indicated, some deployments use metadata of a registrant's raw biometric data, but without transmitting the raw biometric data through networks or storing it on the server system. Some configurations may use metadata that represents the transformed biometric sample to compare instances of such metadata to any of the transformed sample data generated at enrollment of the registrant, or that metadata used to descramble a registrant-specific identifiers from one or more biometric encryption templates.

The metadata or representation associated with a registrant may be in digitized form, text, binary, source code, bitmap, image, sound, video, or any other form that is suitably translatable into machine-readable code, native formats, semi-structured data, or object code, etc. These choices that reside with the operator also constitute a wide range of combinations. Several of the alternative embodiments suggest some variance may arise within classes of configurations to serve specialized acts, goals, or purposes of the mediator operator at either the logic layer, which is protean, or elsewhere with flexibility. Several unspecified alternative implementations also permit query resolution via the BQR Mediator using a secure wireless network by deploying "best of breed" identification or verification techniques that galvanize biometrics and query resolution computation, at least in part.

The computerized privacy officer enables operations, without storing or transmitting files of raw biometric data, to resolve one or more queries into results. A firewall protects the domain from invaders. The concept of having a BQR Mediator does not replace existing privacy or security technologies. Some extant cryptographic techniques that are available and may be compatible include, without limit, public key encryption for authentication, public key infrastructure, biometric encryption, and other approaches for encryption and decryption. Some network security approaches include several evolving standards for wireless network security, roaming and hand-off processes, secure transmission over communication facilities, facility redundancy or session resumption standards, failover safeguards, gateways, or firewalls to protect information within a domain, as well as other messaging techniques or network topologies, especially useful for secure process mediation with external services.

Still other safeguards protect against attack at the hardware, software, operating systems, or application levels, which may include, again without limit, physical security (i.e. of servers, databases, power sources, etc.), failure mode recovery conventions, scalability mechanisms, or node federation conventions. Accordingly, the present suite of mediation methods advance the deployment of a reliable domain which can use, apply, complement, combine, or overlay these or other technologies to enable prompt, urgent, of emergency health-support services, as enhanced by a registrant's self-authored content or advanced intelligence. They can improve or further optimize the privacy or security of timely personalized or customized medical or health related responses, including ones tailored from personal information. Distinct gateways, each managed and controlled at least by such an automated privacy officer, provide the only legitimate pathways out of, and into, the domain.

To address the special security needs of a Wireless Mobility Network, the domain that serves as these distinct gateways may apply the full range of security policies to protect the registrant's data or information from risk. These efforts, like conventional ones for physical security, encryption, and authentication, are usually reinforced by using certain prevention capabilities, such as one like RF Monitoring and Intrusion Protection Systems (IPS), like those on modern commercial Mobility Networks. The authentication processes may optionally include parameters employed in RF management data, as needed. Notably, the BQR Mediator may use database 32 to support the organization of RF management data, as well as to also store either (i) log-in routines to allow registrants to access their accounts, (ii) registrant-authored data and other edited, uploaded, hyperlinked, or otherwise accessible registration content or text, (iii) registrant transformed BCD, metadata from raw biometric samples, or associated data (i.e. image, bitmap, raster, pixmap, XML, privacy metadata, etc.) used for resolution or authorization, (iv) semi-structured or structured data, (v) biometric abstraction models, (vi) EMR authentication data or metadata, and (vii) other files, as needed.

4.0 Method of Mediation for Rapid Health-Care Support Information Via a Secure Wireless Network The Use of Data Structures 101 and Procedures 102A, 102B to Support the BQR Mediator's Internal Message Flow or Inter-Application Processes In many embodiments, the BQR Mediator is designed to safeguard the privacy of the data. There is a two-way "filter" inside the BQR Mediator that intercepts requests coming in and, likewise, results going out. Corresponding to each side of the filter is a set of rules that assesses the legitimacy of requests and results respectively. When a request is sent by an EMR from the outside world, the BQR Mediator applies a set of rules to ensure the request's validity. The rule system permits fully validated requests that may be processed as, or converted into, qualified queries. The mediation rules and procedures permit validated result sets to pass without direct interaction by the BQR Mediator's intercepting applications or filtering programs. Any other request or result set will be subject to reformulation, or if reformulation is not viable, blocking with an appropriate error message.

Referring to FIGS. 6A, 6B, and 6C, one of the streamlining approaches to composing a BQR Mediator entails using as a platform for developing specialized software that is provisioned with mediation procedure 102A and B and mediation data structures 101. Some operators deploy software with procedures 102A and B or data structures 101 for mediation that resides primarily at a layer, which largely resides above a conventional stack of technologies and communication protocols for mobile networks. The rules, procedures 102A and B, and data structures 101, may coordinate or orchestrate interapplication processes that may facilitate resolution, or other acts for privacy or security, performed during preprocessing, processing, or post-processing. These acts may include, without limitation, analyses, comparisons, associations, filtering, database extraction (i.e. using SQL databases, invoking LDAP, utilizing RADIUS Server as an Authentication Server, etc.), process mediation, and blocking.

The use of rules and procedures that are extended in the case of a Mobile Network creates a certain set of special challenges. These are often distinct from those of business LANs or hospital networks for multilevel security concerns. For the BQR Mediator, such specialized software may be provisioned to enable the mediator server system to interwork or mate with one of several vendor-specific integrated platforms for Mobile Networks, which has already surmounted the testing hurdles of high security commercial applicability, as in the sectors like ones that safeguard military secrets. One approach for supporting the BQR Mediator, using wireless security procedures 102B, that resides on a Mobility Network platform, deploys a platform comprised of Cisco's Unified Wireless Network with Unified Communications.

Such a Mobility Network platform may be advanced by provisioning a Cisco Secure Access Control Server (ACS, also compatible with certain Window Servers, etc.), Adaptive Wireless IPS (Intrusion Protection), Mobile Roaming, and Secure Client Management. Cisco's Mobile Service Management Engine (i.e. 3300), may transform a Wireless LAN communicably connectable to a BQR Mediator, with wireless security procedures 102B, into a Mobility Network solution for mediation. Because a number of vendors like Cisco, have established secure platforms for Mobility Networks, which are extensible to software development, the BQR Mediator software may use many of the APIs, protocols and security features of these kinds of Mobility Network platforms. The mediator operator may select a platform for secure wireless networking, from a range of vendors, which best corresponds to the functions and constraints of the BQR Mediator implementation, and any AAA compatibility issues that are priorities Such a Mobility Network platform may be advanced by provisioning a Cisco Secure Access Control Server (ACS, also compatible with certain Window Servers, etc.), Adaptive Wireless IPS (Intrusion Protection), Mobile Roaming, and Secure Client Management. Cisco's Mobile Service Management Engine (i.e. 3300), which may transform a Wireless LAN communicably connectable to a BQR Mediator, with wireless security procedures 102B, into a Mobility Network solution for mediation. Because a number of vendors like Cisco, have established secure platforms for Mobility Networks, which are extensible to software development, the BQR Mediator software may use many of the APIs, protocols and security features of these kinds of Mobility Network platforms. The mediator operator may select a platform for secure wireless networking, from a range of vendors, which best corresponds to the functions and constraints of the BQR Mediator implementation, and any AAA compatibility issues that are priorities.

5.0 Extensions

Typically, the WFC 83 help coordinate interrogation of base resources at preprocessing or processing, as needed by parsing or performing computational operations on the input of the query. For implementations that deploy code to perform query authentication or privacy authorization, beyond plain query resolution that associates personal information, the output data (i.e., text, an encrypted file, template, document, field, link pointer, etc.) only becomes eligible for entry into a result set (S) if certain conditions (A) through (C), below, are true. The conditions, described as (A) through (C) below, hold true, as follows, if and only if:

(A) the request merits an authentication certificate or assertion;

(B) the query may be resolved either by (i) processing a private key or RSI, (ii) analyzing one or more representations of a registrant's transformed biometric sample, or (iii) by matching BCD metadata of a registrant's raw biometric sample; and (C) authorization is unrestricted at a requisite privilege level under the registrant's privacy rules, such that:

$$A \cap B \cap C \rightarrow S \quad (1)$$

or $$\sim A \cup \sim B \cup C \rightarrow S \quad (2)$$

Under lines (1) or (2) above, it stands to reason that this subset of configurations may also be designed or implemented to optionally perform one or more of the other tasks related to authentication, resolution, or authorization at any of the various phases of pre-processing, processing, or post-processing.

Of course, not every part of the A, B, and C formulations in lines (1) and (2) are equally central to the goals of these configurations, generally speaking, nor are they each optional in their entirety. Simplifying (1) or (2) above, though more subtle, one of these configurations that use methods of mediation is sufficiently distinctive over related art in the rapid mediation of medical or health-support data, if a BQR Mediator simply, uses, without prior privity, one or more raw biometric samples to resolve the query under (B), risk-free of reconstruction. That is but for these extended goals, a query resolution process, B (or –B), that produces a result set, S (or none, –S), may suffice as one in a set of the methods.

The various configurations deploying methods in the inventive set of methods may, but need not, have an invariant Quality of Service level or bounded confidence intervals (i.e. minimum accuracy, maximum error rates, etc.). An enhanced resolution process is taught by one or more examples, in more detail further below, including some that operate by harnessing a remotely mediated approach to deploy biometric encryption templates, which may tend to surpass conventional key management approaches that have been common without biometric aspects.

Since there need not be any prior relations between the EMR and a registrant to pose a request to a BQR Mediator to resolve a query, the EMR must be eligible to access the BQR Mediator under the subject deployment's authentication criteria, if any. Under the formulations at lines (1) and (2) above, EMRs may only be qualified upon authentication, which validates some prior, current, or continuing association of the requester to a trusted class (i.e. paramedics, doctors, etc.). An exception often arises for open configurations. Although in some deployments like wholly public ones, that usually can only reveal information already publicly available or otherwise lacking in truly private content. The need for requester authentication may be obviated entirely, except where applicable law dictates otherwise. It is more often, but not always, preferable in contexts of medical or health data, however, to similarly constrain access solely to requesters who are authenticated. This may be especially desired when secure interoperability tends to be supported very selectively, or solely, for instance, with other networks or services operating at least with the demonstrable integrity consistent with prevailing best current practices of authentication and auditing.

Notably, also, a BQR Mediator, using AAA provisioning, enables a registrant to transparently review each actual access to his or her registrant files or data by any third party (i.e. requester, EMR, authenticating peer, etc.). This is often highly desirable when a health-support network is designed using a topology that includes a network of federated servers. Preferably each of such AAA-compliant implementations of a BQR Mediator would be configured, but not necessarily run, to enable the mediator operator to allow registrants to self-audit. The chosen form of biometric analysis used by different implementations of the method may include a growing range of biometric sources that are viable as substitutes, such that the eligible sources of the biometric sample data need not be harmonized by all implementations. It may often be more consistent in a mediation method context to rely upon one or more harmonized sources, however, among federated ones. The mediation method may utilize one or more servers, just as it may be distributed across components or resources of one or more networks. Similarly, it is preferable for operators of a BQR Mediator using one or more servers to use safe programming (i.e. consistent naming conventions, information hiding, and ease of use, etc.) and to disclose publicly the salient Quality of Service parameters of its performance modules.

A. Mediation with Requester Authentication, Query Resolution, and Privacy Authorization Constraints To accomplish any of these objectives at design time, an operator of a BQR Mediator may invert this mode from validating processes to blocking processes. For instance, it may instead block any result set with sensitive personal data unless a resolution query is validated, or, as under (3) below, unless conditions of an authentication assertion, a resolution, and an authorization are each true. All applicable rules will be enforced for every request and the query will be advanced only if it passes all required tests. Blocked results or responses are preferably logged along with other results that are not blocked, either in separate or consolidated formats. Unless an applicable rule permits some explicit pass-through (i.e., messaging or data transfer beyond the mediation domain, etc.), a query preferably goes only to the mediator server, operating as if it were a privacy officer, to generate a default error message when blocked. In symbols:

$$\sim(A \cup B \cup C) \rightarrow \sim S \qquad (3) \text{ De Morgan's Law}$$

For years, many databases have offered ways to retrieve private data via wireless networks. Yet, until now, the related know-how has not suggested or taught how to process a resolution request into a result set (i.e., of identity, profile, or other data, etc.) securely using a BCD metadata file, even wirelessly when needed, to permit customized medical support on-demand or from remote locations risk-free of reconstruction, by using mediation with privacy rules. Some systems or deployments of these new methods may use BCD querying logic, or operate without a separate logic layer, depending upon the sequence, structure, or function of the configuration.

A BQR Mediator may be provisioned to advance or apply one or more transformation processes to raw biometric samples, to create a registrant-specific identifier, biometric representation, metadata, or a biometric encryption template, etc. The transformation usually encodes or transcodes the raw biometric information into some cancelable form, an alphanumeric string, or machine-readable data, or such other similarly irreversible metadata or data. This may be commonly done to abstract the raw data by including or invoking one or more of a very broad range of algorithms that yield a representation or metadata in some form that, of necessity, is not pragmatically susceptible to reconstruction, reverse compilation or reverse engineering by impersonators, hacking programs, or unauthorized external systems. Alternatively, a certain number of transformations may be interposed as one or more intermediate analytical acts, according to procedure or processing instructions, especially to advance classification, indexing, filtering, sorting, or disaggregation of identifiers into subset, or sub-subsets, etc. A programmatic selection of applications in correspondence to certain operator chosen time limits, may invoked so as to satisfy a selected configuration-specific time constraint for cumulative processing of a query, as in the query resolution process above that yields either B or –B. This may improve performance, increase speed, or ensure ease of use, by enhancing efficiency.

In some configurations, the BQR Mediator supports the recognition of certain matching metadata that is stored to represent the raw biometric sample, which was transformed at enrollment. This may be achieved more indirectly sometimes, such as by loosely coupling the mediation and enrollment procedures through some common range of operation and performance specifications, so long as the confidentiality of such specifications is also protected consistently with certain security and privacy safeguards of the controlling mediation process generally. When allied with an independent enrollment service, the mediation that is enabled arises between the EMR and that service, in lieu of the registrant. Compare, FIG. 1. The invented set of methods may satisfy these goals, including the dual privacy of the registrant's raw biometrics and personal health data, with or without adhering across compatible configurations to any single composition that is invariant. Enrollment of personal information could use a service distinct from enrollment of data derived from a raw biometric sample. Some configurations may assign an algorithm drawn, perhaps at random, from a specified class of reliable algorithms used that are for a transformative purpose, under the principles of algorithm independence. The mediation application, for these configurations, is given access to any cryptographic algorithm supported by the underlying cryptomodule compatible with the configuration's composition, where the application may use one cryptomodule as easily as any other. This independence may ensure that an algorithm ascribed to transform the data of one registrant cannot predictably decode the data of any other registrant.

In one embodiment, a BQR Mediator's authentication server receives a request by using a programmable application, detects authenticating data from the message header, normalizes some data of the request into a machine-readable query, and may output a privacy token to calibrate the EMR's access privilege level to registrant data. If no authentication is possible, the BQR Mediator returns an error message.

With the transmitted data derived from a pattern of biometric data of an authenticated query, the BQR Mediator processes data to associate or match the transformed BCD captured from the request with prestored transformed BCD, to resolve whether or not a person was registered. The BQR Mediator may use one or more servers, operating systems, programmable applications, or database extraction mechanisms to process or retrieve data in storage. It may also or apply other resolution utilities for resolving the transformed, cancelable, combined, complex or composite modalities of BCD, BCD-derived data, or one or more measurements thereof Reflecting registrant-specific consent for access, use, collection, or onward transfer of personal information, the mediation software may control such information under privacy rules to constrain access to certain PHRs or health profiles, and a hierarchy of privacy privileges may be calibrated by the registrant to apply to one or more subclasses of EMRs, such as doctors, paramedics, urgent care workers, first-responders, nurses, clinicians, firemen, police, or other EMRs. In another embodiment the mediator server applies a privacy token reflecting a requester's role to form a query to sort items with reference to a registrant's data object, which were earmarked by metadata of privacy levels. That privacy metadata or designation, was used by a registrant to disambiguate between the access permission of classes of personal data to kinds of EMRs or other parties or requesters by roles. One access level, for example, could be for doctors only, and another for some other EMTs and paramedics only, as opposed to excluded nurses, physician's assistants, and clinicians, etc.

Figure 7:
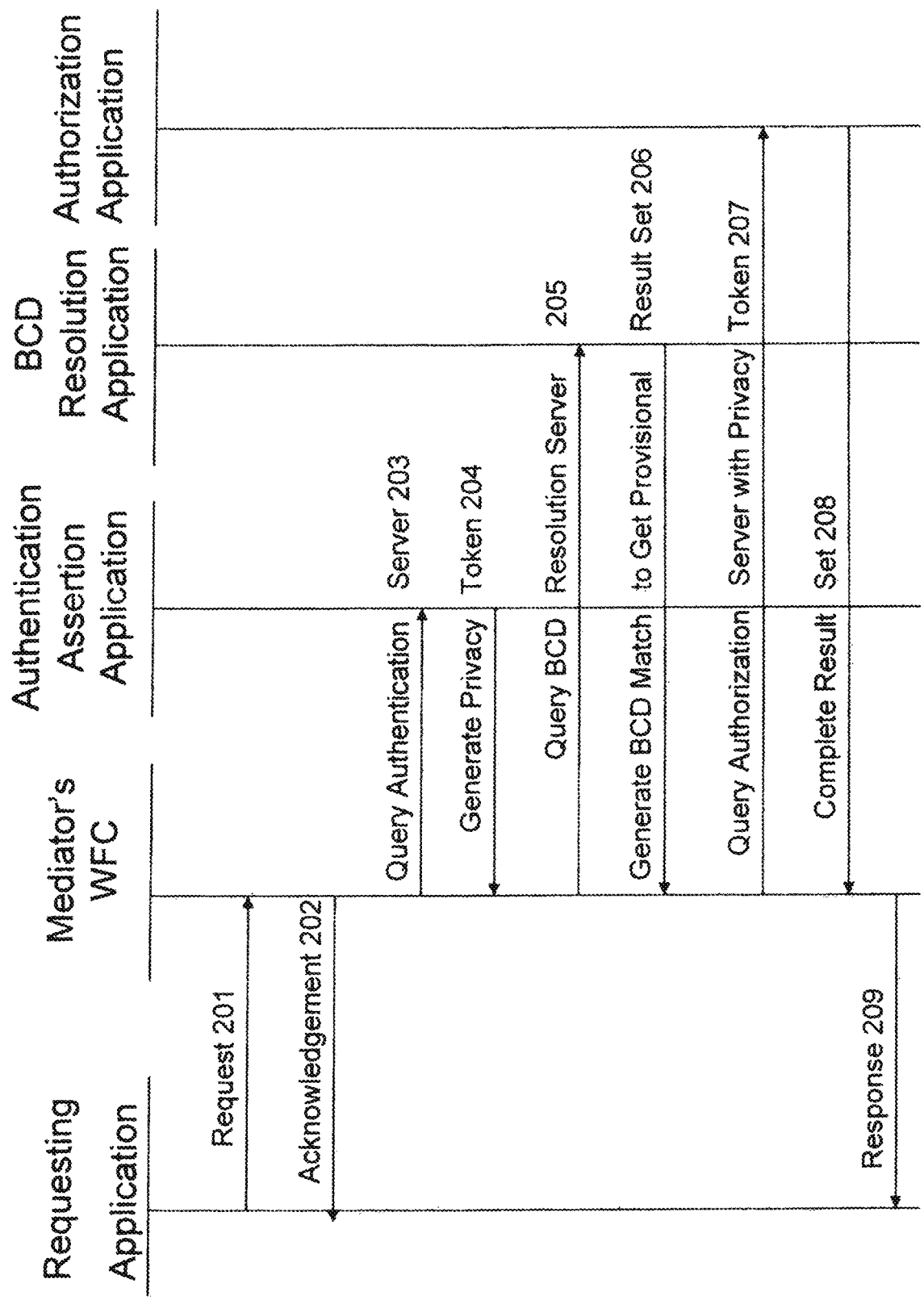
FIG. 7 is a message flow diagram illustrating one implementation of the workflow controller, according to one embodiment of the invention.

B. Preprocessing to Attain a Privacy Token and Resolution Prior to Authorization Process The mediator server 100 (see FIG. 4) may include several features to provide privacy, security, and to control access to the workflow definition files 51.sub.1. As discussed above, the mediator server 100 may include a provision for branch locking, flagging, or sequential processing, as needed. These operations may be used in preprocessing, for instance, to surmount all potential blocking events of preprocessing (i.e. query validation, lack of privacy token, authentication assertion, resolution, etc.) in advance of processing of authorization. In addition, servers may be used to maintain a wider range of query-sensitive sequences during completion of a resolution request 201 (FIG. 7). Referring to FIG. 5, in one embodiment, the authentication server 86 receives authentication information from a service 80 (not shown) and the resolution server 87 uses the information to match metadata or check transformed BCD. Resolution of the service 80 may be carried as a part of the workflow definition files 51.sub.i.

The servers 86 and 87 may be hardware devices, but need not exist in the same hardware platform, and the servers 86 and 87 need not be tightly coupled. Alternatively, the functions of the servers 86 and 87 may be executable by server 100 or performed in programming stored for preprocessing in one of the components of the mediator server 100, such as the workflow controller 83, for example. Using the above-described features, the mediator server 100 may provide reliable authentication information, like a privacy token to calibrate the EMR's privilege to access data, about the service 80 to the resolution server 87, and the resolution server 87 then performs its transformed BCD resolution function. In one embodiment, discussed below, if the server resolves the identifier of the putative registrant, the server 87 may yield an RSI, such as metadata, name with a UPI, or other identifier.

The workflow definition files 51.sub.i generated by the workflow controller 83 may include specific tasks or subtasks (branches) that must be completed to preprocess the resolution request 201 (see FIG. 7). A simple resolution request may have only one branch. More complex queries 201, such as the resolution request illustrated in FIG. 7—(i.e., to use mediation with AAA to generate an identity, RSI, photo, and profile, etc., from transformed BCD or metadata, etc.) may have many branches. Furthermore, some branches may be so interrelated that they can only be completed in a specific sequence, while other branches can be completed in a parallel, concurrent, or a non-sequential fashion. These interrelationships may often be the result of one branch producing an output resource that is an input resource for one or more other branches. Furthermore, as new services 40.sub.1 register with the registry 82, the interrelationships between branches may change.

C. An Illustration of Logic Flow of a Configuration for Processing Authorization Service Queries Using Inputs Comprised of Preprocessing Outputs Either the preprocessing of authentication to attain a privacy token, or of resolution to produce an identifier, may terminate the query, without going beyond such preprocessing by server 87, or servers 87 and 88. If no block arises, however, these servers instead may generate query messages or inputs to permit processing through the authorization server 88. During processing of the authorization program, the authorization server 88, may sort, collect, or generate a provisional set of files or data associated with a registrant by using an RSI as an input, which RSI was an output of the resolution server 87. The authorization server 88 may use a privacy token, from the authentication server's 86 output, to then filter out, distill away, from the provisional set, such data (if any) of the provisional set that may either not be included in the result set or excluded from any transmission of a response coupled with a result set. In no event, will filtered out data, not included in the result set, be releasable to that specific requester via a transmittable response.

If service 80 yields a blocking event at either of these preprocessing attempts that concern servers 86 and 87, however, the result set is empty. No authorization query need be instantiated. A response, signifying the lack of adequate authentication or resolution, may be directed back to the requester via the communication network. Conversely, if no block occurs, but the transformed BCD can be associated with a registrant whose privacy is unconstrained, the authorization query also may be obviated entirely.

The enabling communication networks that support mediation comprise a wide array of conventional public and private networks, and particularly data and mobile networks. Most of these networks are agnostic to the role of the wireless communication device, whether activated to operate in a client application role or, more unusually, to operate as a peer in a server mode using a server application on a mobile operating system. There are numerous examples of mobile telephones or other WCDs that may run transformation algorithms on programs and that operate communicably with embedded, collocated, linked, or ancillary BMA. Such communication devices serve extracted data outbound to other nodes on a network, including server nodes or BQR Mediator nodes.

Figure 8:
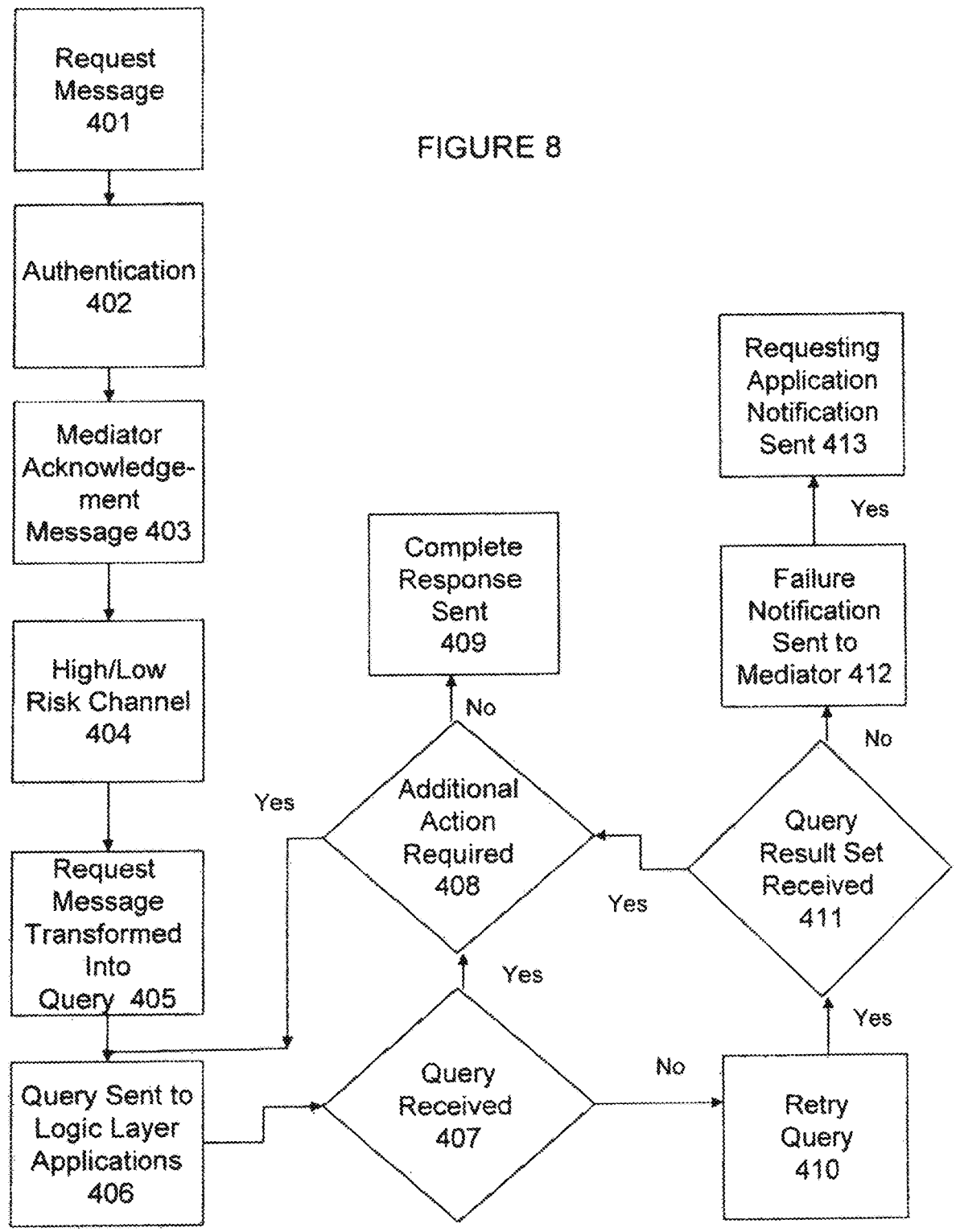
FIG. 8 is a flowchart illustrating the operation of the mediator server system with a set of logic layer applications, conducive to iterative query execution operations using loop arrangements, according to one embodiment of the invention.

Referring to FIG. 7, the message flow diagram depicts the typical flow of messages in one embodiment between optional components or processing modules of the BQR Mediator to handle a request from an EMR or external client, via a Mobility Network platform, that can culminate in packaging response coupled with a result set. The suite of logic layer applications 132 to which a request message is directed will respond to the message from the mediator 100, as if it received the message directly from the WFC 83 on behalf of the requesting application 18, provided the request may be converted directly into a qualified query, in accordance with data structures 101 like query processing rules. See FIGS. 5, 6, and 8. Referring to FIG. 8, the diagram shows an example of a mediator server system that can deploy a set of logic layer applications 132 in a sequence, conducive to iterative query execution operations using one or more formatted loops. See, e.g., RANSAC techniques using iterative processes and the elimination of outliers. The BQR Mediator tries to reformulate the request into queries, in view of a privacy token derived by authentication, to extract the data or contents that the EMR at least has the privilege and authorization to use, under the principle of least privilege. If a reformulation is possible, then the reformulated query will be evaluated in place of the original request or a query derived directly from the request. Otherwise the original request is rejected. This approach also facilitates the evolution of the privacy policy enforced by the BQR Mediator.

In this manner the mediator 100 may qualifiedly extract data from the information storage accessible by logic layer applications 132, if the query from the EMR or client programs 18 satisfies the set up rules, query processing rules and the result processing rules 101. The result set from a logic layer application is called or sent to the mediator 100 and is processed by the appropriate processing logic module and mediator procedures 102A as designated by the workflow controller 83. If the received result set is a rule-compliant result set that is responsive to the client request, the workflow controller 83 can be provisioned to form a message to conform to the format used by the EMR's requesting application and to transmit a response message via a Mobility Network to that requesting application, indicating that the request has been completed.

If the result set received from a logic layer application is not a rule-compliant result set, the mediator 100 will act as a privacy officer and message broker to obtain a rule-compliant result set, rather than a provisional, incomplete, or overly inclusive result set. For example, if, in order to complete the request, further information from or action by a logic layer application is needed, referring to FIG. 5, the flow logic in the relevant workflow controller 83 will receive the method call or message from the logic layer application and will recognize it as an incomplete, non-compliant, or provisional result set.

The flow logic of the processing logic module will identify the further information or activity required based on the received message, and other data from the domain or network, and will automatically format the next call or message and transmit it to the appropriate secondary logic layer application. Upon receiving a result set from the secondary logic layer application it will repeat the process until a rule-compliant result set is completed and received.

As used herein the "secondary" logic layer application could be the original logic layer application or a different logic layer application. The term "secondary" is used to identify the logic layer application that receives a second query message from the processing logic module, which pertains to the original client request.

The workflow controllers 83 can send additional messages to tertiary or higher order logic layer applications as needed to complete the result set. Request-response messaging may take several forms (i.e., SOAP Request/SOAP Response, WML Request/WML Response, or HTTP Request/HTTP Response, etc.) In another embodiment, the higher order logic layer applications may be used, particularly in certain highly scalable identification operations to filter registrants down to a candidate list of registrant conducive to applying verification operations. Sometimes these may be reduced to certain combinations of indexing or classification approaches.

D. A BQR Mediator May Control Flow of Messages to Block Transmission of Results

In one embodiment, described in FIGS. 5 through 8, the BQR Mediator controls the workflow and uses internal messages to certain logic layer applications and databases to govern whether the database query results should reject the input (and block an affirmative result set) or not. Operation of this embodiment will be described using a specific wireless EMR request example of a request by a client program for a resolution. Reference is made to the message diagram of FIG. 7 and the flow chart of FIG. 8, in view of FIG. 5. The resolution request is initiated by an EMR terminal or WCD with a client program from, for example, a mobile terminal 18, where said terminal 18 could be activated at the outdoor premises of a stroke injury of an unidentifiable victim, and such request is received at mediator 100 (block 401).

Referring to FIGS. 7 and 8, to follow message flow, and logic patterns, together in one embodiment, a resolution request message 201 is sent from the client to the mediator 100. That message includes data to attain an authentication assertion of the EMR and the EMR's terminal. It also contains the pre-qualified form request to be submitted as a query, an attached file of transformed BCD extracted from a BIIU, as well as the other optional parameters of a form to ensure that a timely transformed BCD file, authorization key, or RSI is sent over a secure wireless network. The request for a resolution is authenticated as to source, terminal, and request form (block 402). An acknowledgement message 202 is sent from the BQR Mediator to the EMR's requesting application (block 403). The request message is preprocessed by an application or servlet of the access server 85 (FIG. 5), which substantiates the authentication certificate from the message header, and validates the form of the request with WFC 83.

Message 201 is then transformed and the message body decoded by program instructions of the access server 85 based on its internal logic to a query format and structured definition language (SDL), compatible with or native to the relevant access protocol and logic layer application (block 405). A message 203 is sent from the BQR Mediator for preprocessing to another logic layer application at the authentication server 86 that handles authentication assertions to issue a privacy token (block 406). The use of the terms messages, queries, or responses, as used in the rest of this example denote local method calls or data flows that are solely internal to the mediation server system or domain, except where otherwise expressly indicated.

The logic layer's authentication assertion application sends an internal response message 204 to the mediator's WFC 83 substantiating that it has completed authentication querying, generated an authentication assertion, and issued a privacy token, or issued an error message. If no error message issued, the mediator's WFC 83 continues the preprocessing, by sending a message to the resolution application of the logic layer 132 at the resolution server 87, with the privacy token and a transformed BCD resolution query, via message 204 (block 407). The resolution application, in response to the privacy token, determines, from its internal flow logic and data structures 101 with rules or models dedicated to query or result processing 101 using privacy metadata and calibrations, what additional action or internal messaging is required to build a result set (block 408).

E. Message Flows Terminate with Error Messages if Blocked to Preclude Execution that Produces a Result Set In the present example, referring to FIGS. 7 and 8, the internal flow logic of the resolution application would indicate that the requested result set is not completed or rule-compliant and that further action is required. In turn, the WFC 83 sends message 205 to the secondary preprocessing application for transformed BCD matching, so the resolution application of the logic layer 132 may process transformed data of the newly captured transformed BCD input or metadata of the request attachment, which was translated or parsed from client request 201, and, if possible, match or associate that transformed BCD with any pre-stored transformed BCD template (block 408). The secondary application sends a message 206 to the mediator WFC to substantiate that the appropriate transformed BCD match was made and that a registrant has been identified by RSI, UPI and name, and a database-generated provisional result set, from the RSI, UPI and name, metadata, or transformed BCD match. That resolution (block 406) may refer to data that typically includes a profile, composed of one or more data fields. The output may include a facial photograph mapped to an RSI. Upon resolution, this earlier preprocessing permits entry into a processing phase, but if no resolution were available, the resolution application could send a message back to the WFC to indicate the transformed BCD was not matched or associated with a registrant.

Referring to FIGS. 7 and 8, the WFC 83, based on its internal flow logic using a privacy token with either the RSI or the UPI and name, sends a query message 207 requesting a processing of authorization to a tertiary logic layer application, or via an authorization application (block 408), running on the authorization server 88. The authorization application processes the query to sort or retrieve the data of the provisional result set that did not need to be filtered out as private. The authorization server responds with a message 208 to the WFC 83 substantiating that the result set as authorized is rule-compliant and completed (block 407). This message by the authorization application substantiates that the request for resolution has been completed is the final process in the internal flow logic of authorization processing. The result set may be a null set or contain or reference data or content for identification.

The workflow controller 83 indicates that the desired resolution has been authorized and completed. In turn, the mediator 100 may be configured to substantiate that the result set is rule-compliant for coupling it into a response that is sent as an external message to the requester. Again, because this mediator operator has configured this embodiment with the optional post-processing module to package the result set into a response message back to the requester, the mediator's WFC 83, access server 85, service composition modules, and channel or connectivity layer send a message 209 to the external requesting application substantiating that the resolution has been successful (block 409). The response contains the name, RSI, UPI, profile, and facial photograph of the registrant whose transformed BCD was matched.

It will be appreciated that the requesting program, or EMR's client application, in this example, is preferably not involved in the intermediate messaging because responsibility for all intermediate steps was taken over by the BQR Mediator. The client simply made the original request and was not involved in the process until it received a notice that the resolution was complete. Another embodiment of the mediation method is complete upon culminating with an internal result set, and without the generation of a response coupled with a result to the requesting application.

Figure 9:
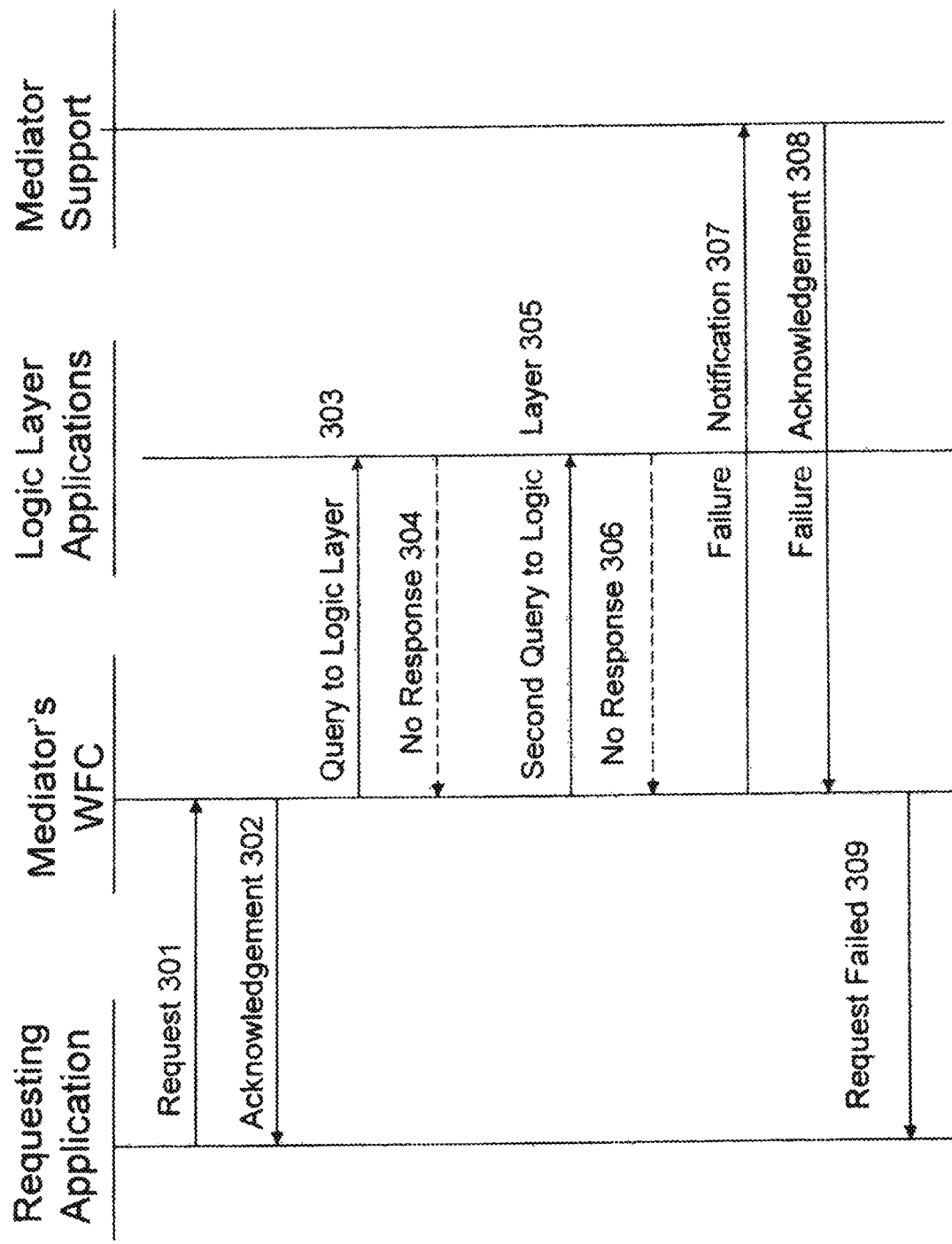
FIG. 9 is a message flow diagram illustrating another implementation or instance of the workflow controller, according to one embodiment of the invention.

Whenever the BRQ Mediator is configured to assume responsibility for completion of client requests by generating a result set, whether it is affirmative or negative, it is necessary that the processing logic be monitored by software or facilitator to ensure that the request is handled without disruption to a proper disposition, even in the event of a failure to complete or blocking event. Initial responsibility for completion lies with the processing logic module that handles the request. Referring to FIG. 9, messages 301, 302 and 303 correspond to messages 201, 202 and 203 as previously described with respect to FIG. 7. The processing logic module tracks each request and includes logic for determining if a request has been affirmatively completed in a timely manner (block 407). The time for completing a request will vary with the type of request but the processing logic sets an expected time for receipt of a result set. If no responsive data message 304 is received during the expected response time, the processing logic module can reinitiate the request by reseeding a copy of the original request message 305 (block 410).

If no responsive data message 306 is received in reaction to this second request (block 411), a message 307 is sent from the processing logic application to mediator's WFC 83 indicating that a request has failed or been blocked (block 412). That authorization server responds with message 308 to the compose services module of the BQR Mediator acknowledging the failed request. In turn, the BQR Mediator composes a service of failure notification by sending message 309 to the requesting application with a request failed message (block 413). Optionally, but preferably using best practices, the mediator's operator or policy supervisory personnel can then investigate the failure and take appropriate remedial action, including any revision of the processing or rule application logic or the like.

Notably, a mediator's service composition module optionally may be responsible for fulfilling the original request through post-processing activity, whether to produce an automatic external response or otherwise.

Some configurations of the method use software to mediate data using gateways. This set of gateways governed by the mediator system is preferably envisaged as a distinct computer server system; we refer to such a system as a BQR Mediator. In the BQR Mediator, a result set of a query is processed using the mediator server. The mediator server submits queries, using data from a request, to a database system, to which it is communicably connected. Any of the components of the BQR Mediator either may be part of the mediator server or physically. distributed. The information storage unit optionally may be organized as one or more databases, distributed over a network, or collocated at the server system. Each BQR Mediator operator may be providing remote health care support services subject to different or similar performance constraints. A server-supported analytical module for biometric transformations or abstractions, if any, may be logically or physically separated from the mediation software, for instance, as when accessible applications, data structures, interfaces, or logic layer programs are communicably connectable, rather than integrated with, or tightly coupled to, the domain of the BQR Mediator. Deployment choices may vary by relying on a wide range of distinct distributed computing techniques, as needed.

The mediator server may operate either unattended or attended, depending upon the different objectives, resources, configurations, platforms, or environments, but the BQR Mediator may perform the role of a default privacy officer automatically in either case, at least in the first instance. If the BQR Mediator cannot preprocess a request into a query with an authentication assertion or privacy token, it preferably generates a result set that reflects that the request was not authenticated, or an error message reflecting the same. If this digital privacy officer ("privacy officer") is unable to reconcile, process, or match data of an authenticated request with that of any prestored files of transformed BCD information when queried to do so, it preferably generates a result set that reflects the request for resolution was either declined or not authorized, or a message reflecting the same.

The message flow patterns depicted may be modified to satisfy the selected biometric resolution approach utilized, and are merely exemplary and not limiting. Some embodiments that deploy biometric encryption techniques to process remote request using BCD metadata, and do so in an effective way of enabling performance as an automated privacy operator, that is risk free of reconstruction. For example, using one of many biometric encryption (BE) services for verification of a profile query, a BQR Mediator may invite a query, the query may be confirmed as one for verification with prior identification, and the identification may be matched with a biometric encryption template of the registrant. That template may be sent to the EMR so that the EMR may capture a live biometric sample, and submit the sample into the template to generate, if verified, a registrant's robust PIN. The EMR may convert the robust PIN into the corresponding registrant's private key, pointer to an encrypted profile, and a crypto-key, by sending the PIN to a trusted Certificate Authority (CA), provided that the CA has been trusted by the registrant to do so. Then the EMR may successfully advance the request for a profile to a BQR Mediator. Some configurations will perform acts beyond resolution to send an encrypted profile conducive to sharing with the EMR certain content data like a profile, or directives, composed of data at least partially submitted by, or on behalf of, the registrant. Only the content's metadata or opaque packaging due to encryption is typically used or disclosed directly to the operator of the BQR Mediator, so that the delivered content may remain confidential through any optional transmission thereof, from its source to its sink (i.e. destination, EMR, etc.), as needed. With the registrant's encrypto-key, the EMR may decrypt the rule-compliant response with content to help personalize or customize the remote medical support.

F. Mediating Biometric Data into Results Using Biometric Encryption with an EMR

An alternative embodiment of the BQR Mediator runs software to process a request, partially emulating certain underlying processes already discussed under Biometric Encryption above. While these embodiments distinctively rely upon a BQR Mediator to securely control the sequence of message flow, in view of special allowances for the EMR's lack of earlier privity to a putative registrant, much of the message flow may resemble the flow from servers described in the Case Study number 2, of the Cavoukian Paper cited above, which includes a trusted Certificate Authority. Here the BQR Mediator restricts access via authentication, but also typically relies upon certain implied rights of the EMR acting as if he were the registrant's hospital, which of course he is not, and applies configuration-specific distinctions, including ones for public key management along with wireless compatibility, to advance prompt, private, and secure rapid remote health care support. See, also, infra at note 1.

This configuration is another example that enables request-response messaging from remote mobile devices, as in FIGS. 2 and 6, using a data network that partly comprises one or more secure wireless networks. It may be designed for verification queries, for example, using software to enable the illustrative set of exchanges at runtime, as described below:

1. If Alice does not have her smart card with her (e.g. in the case of an emergency, urgent health diagnosis, etc.), an EMR, who is providing Alice with medical care services, uses a client application to ask the BQR Mediator to send Alice's BE template back to him, at least partly over a wireless network;

2. The EMR complies with any server protocols of the BQR Mediator to authenticate him or wireless device, or both, as needed for an authentication assertion;

3. The EMR captures Alice's new biometric sample by applying it to the BE template and recovers on-the-fly Alice's PIN, and then wirelessly sends Alice's PIN to a Certificate Authority (CA) to regenerate Alice's full legal name and UPI (or RSI), her private key, the pointer to her encoded medical record or profile, and the crypto-key thereto, and the CA securely transmits the data back to the EMR (i.e. using public key encryption, shared secret, etc.);

4. The BQR Mediator sends the EMR, acting on Alice's behalf, a fresh random challenge;

5. The EMR, as Alice's proxy, identifies Alice (i.e. by her RSI, metadata, or UPI, etc.) and signs the challenge for her with her private key and transmits to the BQR Mediator data that substantiate Alice's signature, on her behalf;

6. The BQR Mediator authenticates Alice's signature by programmatically confirming the validity of the signature under her public key;
7. The EMR, again as Alice's proxy, securely sends the BQR Mediator the pointer to her medical record;
8. The BQR Mediator runs operations that recover Alice's self-registered profile, or a part of it, in encrypted form, as may be redacted to the EMR's privilege level that corresponds to his authentication assertion, and securely sends it still encrypted to the EMR, acting on Alice's behalf;
9. Using Alice's crypto-key, which was regenerated from her PIN, the EMR, as Alice's proxy, decrypts the content of her profile sent, for prompt remote or location-agnostic use;
10. Alice's biometric, the PIN, the private key, the pointer, and the crypto-key, are discarded.
11. The BQR Mediator preferably revokes and replaces the used PIN, and the CA revokes and revises Alice's private key, the pointer to her profile or medical records, and the crypto-key.

In this alternative configuration, the BQR Mediator (roughly in the role of the BE template database administrator) has an assurance that Alice's biometric sample is, in fact, hers and that she is the registrant that her proxy, the requester or EMR ("requester"), claims her to be (since the requester was able to unlock her data by capturing her biometric sample to descramble or unlock Alice's BE template at the wirelessly connectable remote location). The BQR Mediator is also assured that her profile or health record was sent to the right person, a requester who presented Alice's metadata that was obtained when data was captured live from her raw biometric sample. On the other hand, Alice (subject to her requester's use, as limited by her stored privacy rules) retains full control over her medical record and/or profile, so that even the BQR Mediator (the database administrator) has no access to it, since the operator of the BQR Mediator does not have the crypto-key to decrypt it.

Because the public key management in this alternative embodiment is compliant with the best current practices of AAA, the BQR Mediator may be queried at any time by Alice to audit when her content or profile was requested, when her private key and signature were validated, and to whom the encrypted profile or data was delivered or disclosed. The requester or his wireless device, or both, may be subject to the rigorous safeguards of the best current customary practices of AAA, their equivalent, comparably robust, or successor techniques as updated from time to time. When the operator of the BQR Mediator is also trusted, the roles of the Mediator may be consolidated.[3]

[3] It follows that enhanced security for an untrusted intermediary is not a necessary part of the invention, but is supportable by various embodiments thereof.

To compose a method using software to mediate profiles, the selected criteria for requester's authentication may pivot on one or more safeguards or policies variably, provided that the safeguards or policies are not unlawfully concealed from registrants. Preferably, mediator operators would embrace the level of safeguards most likely to efficiently eliminate unreasonably high levels of risk for each targeted classes of registrants. These configurations may vary based upon different degrees of risk tolerance or applicable legal requirements, as may be modified from time to time. Under one option, for instance, requester-level authentication may be performed also using BE techniques with data corresponding to the requester's biometric sample, in lieu of conventional approaches like two-stage authentication. Many of the functions in the example on a BE configuration may be consolidated in some deployments, including without limitation, for example, the requester's sending of Alice's signature and pointer to the BQR Mediator.

More subtly, one embodiment permits the BQR Mediator to control EMR access to legacy archives or databases of health data of one or more autonomous and externally operated services (hereafter "external database"), whether or not the later use biometrics. As another natural extension of biometric encryption techniques, a BQR Mediator as in FIG. 2, may also reconcile a requester service model used by an EMR and the provider service model of an external service (not shown), which may use a database to archive the personal health records, ICE, or profiles of individuals. We assume that the external service is not closed, but requires the individuals or their health care professionals to authenticate themselves to access or use stored data. The BQR Mediator may also seek access thereto for an EMR, however, when the EMR serves as an individual's authorized proxy for rapid care support. Where the external database employs conventional two-stage authentication, for example, for the individual's physician's assistance, the BQR Mediator may enable an EMR to secure the retrieval of personal information from a discoverable external database. Upon receiving the EMR's query, the BQR Mediator may serve as a hub to enable the EMR to translate data of the query by returning a biometric encryption template to the EMR, so that the EMR may generate the individual's PIN, and secure data that can substantiate to an external database her private digital signature or password as well.

By decoupling the provider service model of the external database from the BQR Mediator's domain, while facilitating the EMR's redirection to the external database and supporting the EMR's external authentication, some configurations enable the EMR to qualify to retrieve the individual's data from such an external database. In this context, the BQR Mediator usually will ordinarily rely upon a table of name-value pairs to advance discovery of an external database used by an individual. This presupposes that the individual has previously locally stored her transformed biometric data, and the name or description of her accessible external database operator also, for BQR Mediator use. The BQR Mediator deploys the individual's biometrics, as stored using a biometric abstraction model, to enable the EMR to become eligible to attain such data and provide rapid remote health care support via wireless network. Another optional extension could extend the local rules to the external database too, for instance, where said individual-specific identifier has been derived locally using said transformed biometric data transmitted by the remote request, and that identifier has been designed to encapsulate at least one query result post-processing rule, such that the redirection may also facilitate a secure transmission of a response message, coupled with said external database output, to said requesting application, subject to said rule. The artisan will understand that the external database may correspond or use other external databases similarly, invoke a compatible biometric abstraction model, or may use another different authentication technique, etc. The later may allow one or more stages to be satisfied, for example, by either reliable EMRs or qualified correspondents who utilize smart-card, credentials, or robust PINS.

G. Mediation to Enable Personalized, Customized, or Varied Health-Care Support

For another embodiment, when a specific condition like a stroke or other specialized emergency cause is evident or cannot be excluded, EMRs may be guided by a mediated response that conspicuously couples the profile or identity with one or more advanced directives, in view of personalized risks that were self-managed by the registrant.

In one embodiment, the BQR Mediator is extensible to adaptations and can be designed to quickly convey directives, practices, or instructions to EMRs that pertain to each registrant's heath care support needs, for instance, based upon measures, that include, but are not limited to, opt-in or opt-out rules specified by each registrant, that may concern his or her rapid or urgent care which are either:

(a) personalized, in view of current or prior medical or health conditions;

(b) customized, in view of known or likely causes, external conditions, or risks; or (c) varied, in view other foreseeable or unforeseeable causes or circumstances The BQR Mediator may introduce specialized emergency medical response capabilities enhanced by mediator responses that simulate active patient participation, even when a registrant is not lucid (i.e., avoidance of conflicts with drugs routinely taken, treatment and routing for stroke to a stroke center, Alzheimer's, etc.). Some patients may direct highly customized responses affected by advance directives that depart from community procedures otherwise employed by EMRs by default, in part through virtual auto-pilot control conveyed asynchronously through the BQR Mediator.

As such, the BQR Mediator can enable service as even an unconscious patient's strategist by proxy, or as a timed-deferred avatar or advocate, particularly for reducing anticipated or foreseeable risks. For example, Mrs. Henderson may register with a known risk of a certain kind of stroke and use the mediation method as her surrogate to direct, absent her supervening instructions, that she be taken first to her desired stroke clinic or the closest similar facility in her emergency service zone that can administer an MRI and tPA.

A mediator operator could configure a database, archive, or other storage medium for authenticating EMR access to permit rapid identification or verification of customized record data of registrants, by prestoring in a storage medium, accessible by the authorization server, one or more data objects, securely sent, comprising at least a portion of the registrant's profile and a portion of the registrant's transformed BCD. The BQR Mediator processes requests that seek a resolution or match, but only for expressly or impliedly specified modes of transformed BCD, rather than other unspecified (i.e. incompatible or less reliable, etc.) modes of transformed BCD.

In some configurations, the BQR Mediator can be provisioned to initiate a sequence to gain intermediate feedback (i.e. once a candidate ranking list, short list, or subset of registrants, has been compiled, etc.), by the attending ERM. It may, for instance, prompt or ask the EMR, based on the provisional match or matches drawn from a combination of techniques, to confirm if a pre-stored facial photograph (i.e. from enrollment, registration, etc.) of one or more of the registrants' faces is or is not clearly the proper subject of the EMR's prior query. This incidentally may help surmounts another adverse trend, namely: that for most biometric approaches the false acceptance rate (FAR) tends to increase with the volume of database entries. A mixed approach using biometrics and photographs often will reduce critical risks of misidentification. It will be appreciated that the requesting program, or EMR's client application, in this example of one of many alternative embodiments, is involved in the intermediate messaging, because responsibility for one or more intermediate steps were taken over by the EMR's use of the client application on his WCD to reply interactively to the prompt of the BQR Mediator in facilitating feedback. Notably, the term "interactive" does not require any direct communications between an EMR and a registrant (or her client application), who may even be unconscious or incapacitated, but allows an EMR limited forms of communication back to the mediator server domain.

Since many biometric approaches also evince a trade-off between the FAR and the false rejection rate (FRR), some configurations use a photograph from enrollment of one or more registrants may enable an enhanced performance level, or optimization via fine tuning, by allowing EMRs to support improvements in filtering out incidents that otherwise contribute to a higher FAR. In other word, these techniques may reduce the FRR, even with a higher FAR, as the FAR error events will not likely pass scrutiny under with a photographic test.

As some embodiments of the methods are susceptible to use as a backwardly compatible complement to, or overlay to, existing or external information stores of health data, the full registration process of health data anew is not always a mandatory step of the method. Though in many contexts it may be highly preferred. The integrative techniques may rely upon the registrant's self-submission to some BQR Mediator-accessible repository of transformed BCD that may be used as a match template. However, that act too is not always required, since the method may be used where a registrant grants permission to the mediator operator to enable the use of a transformed BCD match template already in persistent storage. Many operators already use potentially complementary databases of electronic records, which may be queried using data gleaned from ID cards, scanned from bar codes on wristbands, or drawn from mobile phones. But rarely do patients have a legal right to control the privacy and accessibility of their self-edited medical data, by their transformed BCD or metadata.

Some of the content data is routinely comprised of registrant profile or health record data that was susceptible to being self-authored (or edited) and self-designated for confidentiality at one or more levels of privacy. Profile data is generally stored in encrypted files or fields and encoded with metadata to calibrate the privilege level or levels. As to personal information, even the mediator operator need not be permitted to decrypt it, especially within every kind of configuration. The privacy constraints and safeguards are rigorously enforced.

Some embodiments support the automated resolution of a remote biometric-driven query to either find, recognize, or share personalize information stored in a computer system, under one or more sets of mediation rules, information sharing policies, or procedures. If the method is configured to share the result set with the EMR, some implementations may rely upon secure wireless networks to support the portability of results with identifying information, health profiles, or medical data, subject to certain constraints or a registered individual's privacy rules. Mediation can permit either EMRs, or their downstream counterparts like medical specialists, to better tailor health care responses to comport with a registrant's personalize care criteria or advance directives, as reflected in a registrant's associated private data. Mediation also may enable similar remote access, by an EMR on behalf of a registrant, to PHRs or related data authored or entered by a registrant, whether locally or in a correspondent repository or archive, consistent with mediation security policies and the privacy principle of least privilege.

Among the subset of embodiments that are backwardly compatible or "overlay" external services that entail enrollment, the BQR may enable processing an EMR request that contains or transmits someone's transformed BCD, so as to enable comparing it to find a match against a one or more accessible or addressable transformed BCD match templates, which may reside on another secure computing domain. An eligible correspondent service, however, could not store or transmit raw biometric data, but could transmit programs to transform or represent raw biometric data. Yet, this overlay approach therefore entails a degree of interoperability that extends an elegant privacy protection policy. Use of the metadata of the BQR need not be mandatory in other corresponding services that instead use transformed BCD methods or nonbiometric authentication, for instance, whenever translations are conducive to interoperability and do not pose higher risks of reconstruction.

Figure 10A:
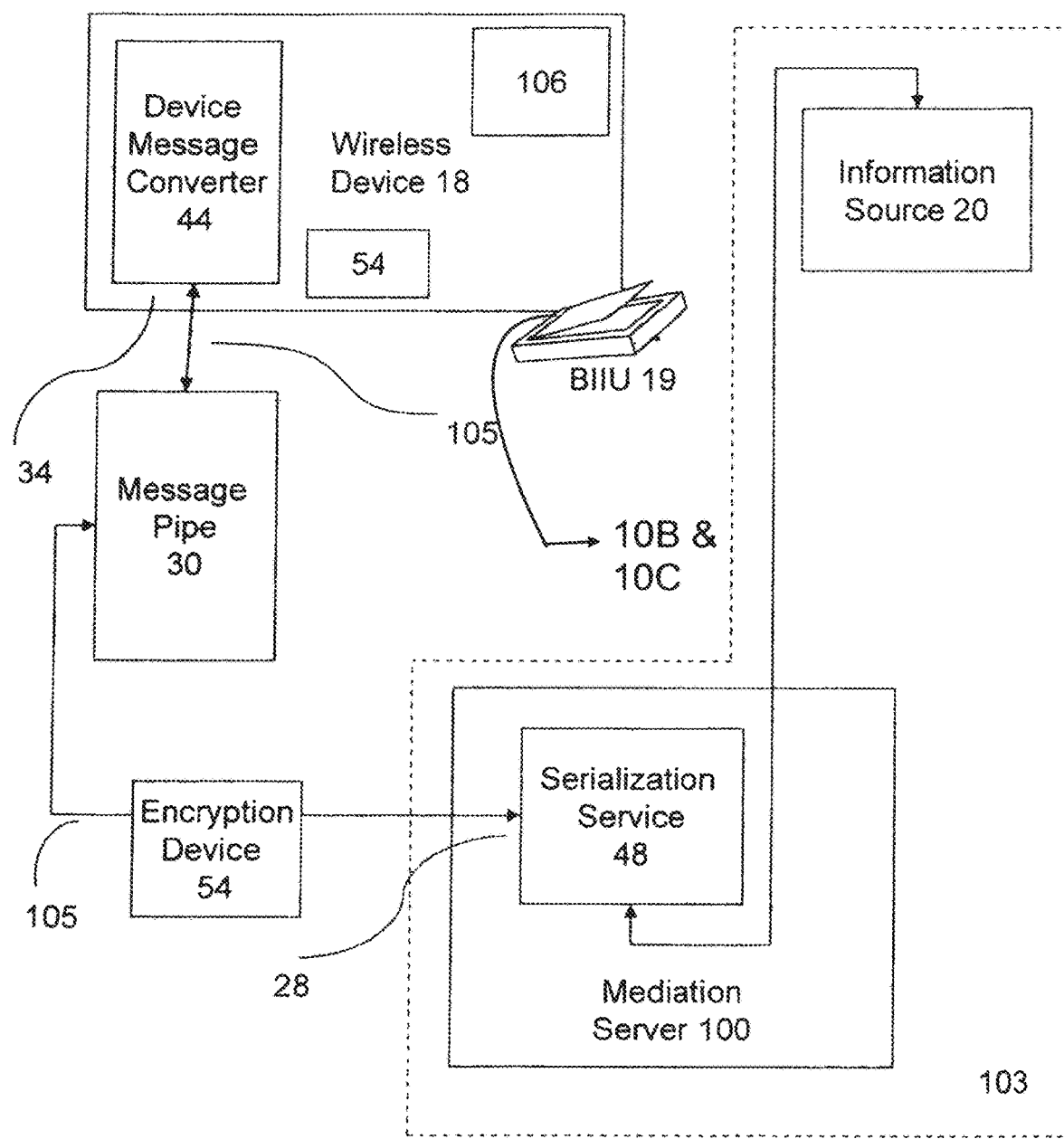
FIG. 10A is a block diagram depicting certain access alternatives to a mediation server from wireless communication devices via a wireless network gateway, and from computers via a LAN and WAN, where a mediation service provider is comprised of a data server, serialization service, and information source, connected by a message circuit or pipe, provisioned with endpoints and with encryption, in accordance with another embodiment of the invention.
Figure 10B:
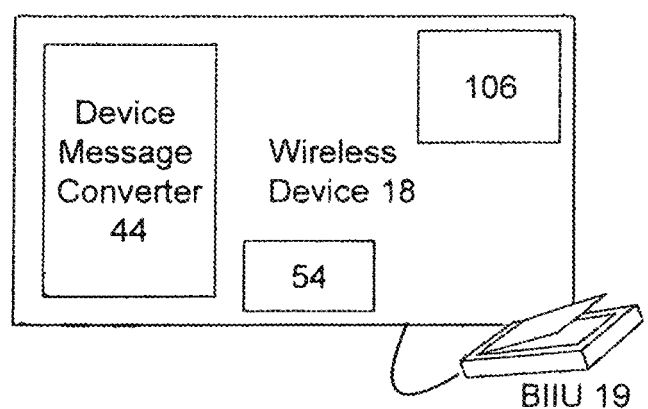
FIG. 10B shows one alternative of a partial view of FIG. 10A of a BIIU that may be configured as an external component of the wireless device, which interfaces compatibly with said wireless device.
Figure 10C:
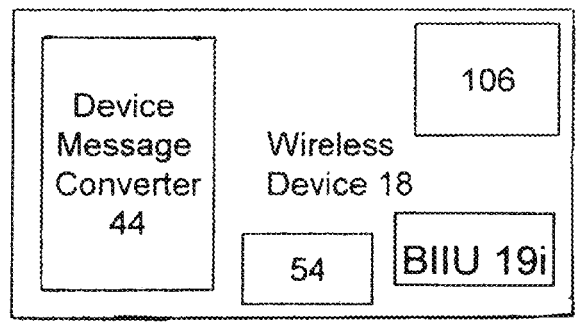
FIG. 10C shows another alternative of a partial view of FIG. 10A of a BIIU that may be configured as an internal component of the wireless device.

H. Mediation as a Web Service Using a Server-Side Component Model with Wireless Transport Referring to FIG. 10, depicting one embodiment, a network topology comprises a plurality of BIIU-compatible terminal devices 18 for interacting with one or more mediated web services 103, provided by a mediator's data server 26a and associated information storage device 32, through request/response messages 105 via a coupled Wide Area Network (WAN) 46 such as but not limited to the Internet. The data server 26a effectively provides the devices 18 with limited access to the information storage device 32, supporting the information service 103. The BIIU-compatible terminal devices 18 may include, inter alia, one or more personal computers, wireless devices 18, laptops, PDAs, portable workstations and the like. The mediated information service 103 may be comprised of Web Services and/or other services such as but not limited to ones compatible with data processing via SQL Databases, Java (i.e. J2EE/Java Data Objects(JDO), JDBC, Enterprise JavaBeans (EJB), and/or JMS, etc.), IDL-based CORBA frameworks, RMI/IIOP systems, environments, or COM/DCOM components. Mediation platforms that are planned to be extensible or federated may use EJB or JDO in some cases as a conventional server-side component model. The java compiler (javac) is the component of the Java Developer's Kit used to transform Java source code files into bytecode executables that can be run in the Java runtime system. The EJB architecture is a component architecture that is suitable for computing platforms that have a traditional composition of a data storage, data processing, and data presentation layer. Also, EJB 2.1, or later versions, allows enterprise beans to be exposed as web services, so that their methods can be invoked by other J2EE applications, as well as applications written in other programming languages on a myriad of platforms. Further, the network topology can utilize a network gateway 15 for connecting the desktop computer terminals 16 via a Local Area Network (LAN) to the information services 103. Further, the network topology can also have a wireless network 24 (i.e. OpenVPN, WAP network, WLAN, etc.) for connecting the wireless devices 18 to the WAN 46.

The wireless devices 18 are wireless communication devices adapted to operate within the wireless communication network 24, such as a two-way communication device having at least data and possibly voice communication capabilities, for example. A wireless network gateway 15 provides an interface between the wireless network 24 and the WAN 46, and performs such functions as wireless device addressing, while supporting set-up, signaling, wireless data communication, and store-and-forward messaging of data to and from the wireless devices 18. Depending on the functionality provided by the wireless device 18, it may operate such as, but not limited to, a WCD, data messaging device, a two-way pager, a mobile telephone with data messaging capabilities, a wireless Internet or network appliance, a data communication device (with or without voice telephony capabilities), and/or a wireless modem configured to operate in conjunction with a computer system or other electronic device beyond BIIUs noted above.

The BQR Mediator may rely on related art that permits the EMR to use a WCD securely wherever the WCD is located. This is so, for instance, whether the EMR is at the office connected to a WLAN, or in a vehicle in route and connected to a TCP/IP network, or at an injury site using an OpenVPN or extended network to connect communicably and securely with the mediator system 100. It is recognized that other devices and computers (not shown) could be connected to the data server 26a via the WAN 46 and associated networks other than as shown in FIG. 10. The terminal devices 18, wireless devices 18 and personal computers, that may be BIIU-compatible, are hereafter referred to collectively as "the devices 18" for the sake of simplicity. Web services are selected by example to represent the secure handling of a resolution request message and any response message in the following description of the system 100, for the sake of simplicity. However, it is recognized that other mediated information services could be substituted for the web services supporting query resolution under query processing rules.

Referring again to FIG. 10, the devices 18 transmit (i.e. send or receive, download, upload, etc.) the request/response messages 105, respectively, when in communication with the data server 26a of the web services 103. The devices 18 can operate as web clients of the web services 103 by using the request/response messages 105 in the form of message header information and associated data content, for example, requesting and receiving inputs for authentication.

Figure 11B:
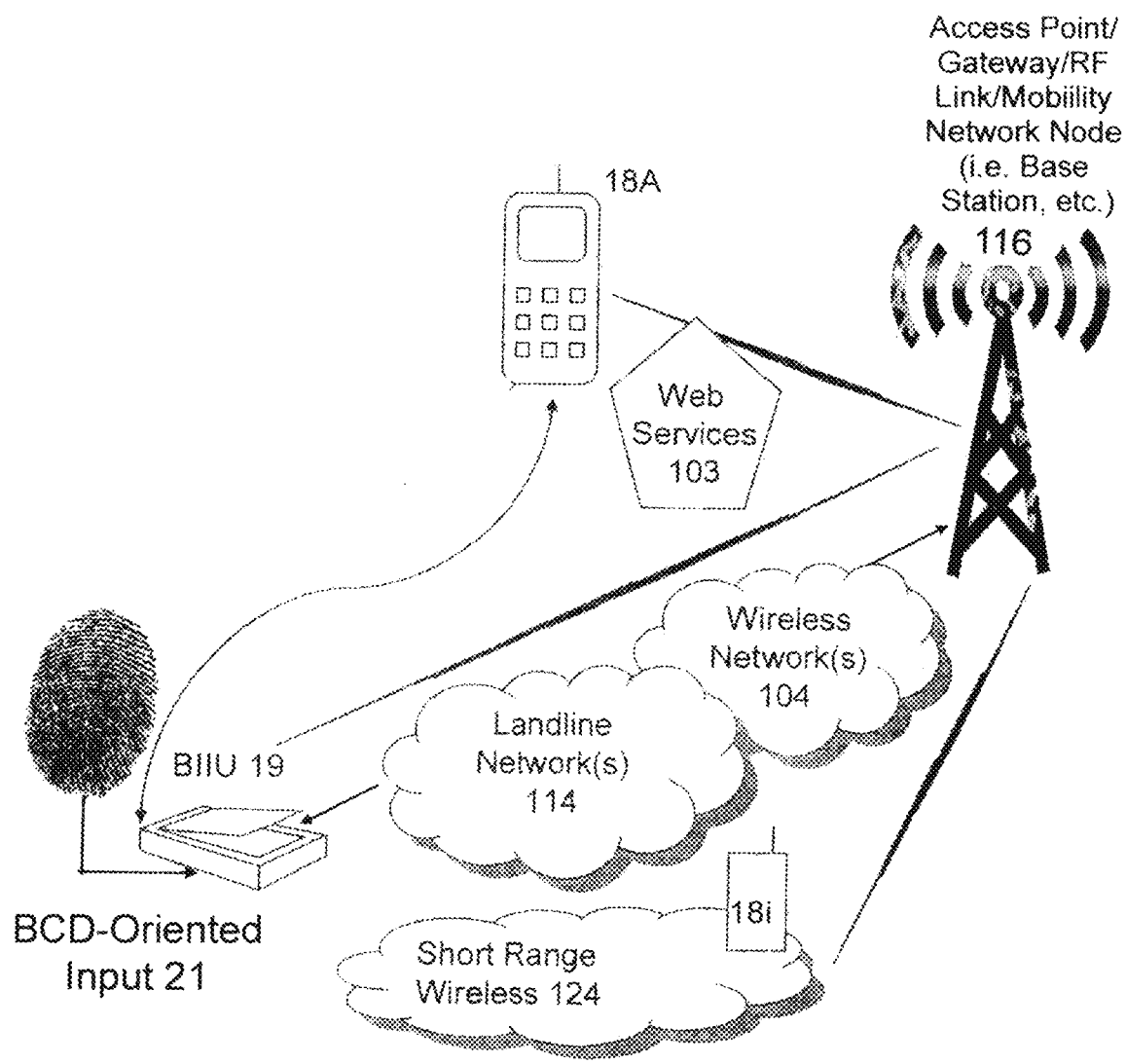
FIG. 11B shows a partial view of FIG. 11A to clarify that a communication device can connect with an Access Point, Gateway, RF Link, or Mobility Network Node (i.e., a Base Station., etc.).

In FIG. 11, the diagram depicts how an EMR may use a wireless communication device (WCD) 18 with an internal BIIU (not shown) to capture, transform, abstract, or transmit the transformed BCD or metadata of a patient, when the WCD supports mobile services transport 134, using a web service interface 136 on a platform of hardware and operating system 130, to connect to the BQR Mediator (not shown), for instance, through either a wireless network 104, or short range wireless communication system 124, or in some combination with a landline network 114. Further, the networks 24, 46, 124, 104, and 114, of the network topology will hereafter be referred to collectively as "the network 46" for the sake of simplicity.

The web service 103 is an example of a service with which client application programs 106 (see FIG. 12) on the devices 18 interact via the network 46 in order to provide utility to EMRs operating the devices 18. The devices 18 can also execute, add, or contain programmable applications, servlets, application specific integrated circuits (ASICs), or hardware to permit processing in a sequence, including without limitation, data encryption/decryption, formatting, serialization, BCD extraction, BCD transformation, or transformed BCD insertion into a message body or attachment, etc.

The EMR's request may be originated with common semantics to ensure that the WCD generally shares the same data representation native to the BQR Mediator. A data representation conducive to processing, for instance, may be based upon one or more prevailing standards, including, without limit, ones that concern either local method calls (i.e. RFC, etc.), interapplication processing, data representation (i.e. WML, HTML, HDML, etc.), messaging (i.e.

WAP, XML message, XML over HTTP, WML over WAP, request-response, or SOAP, etc.), or a structured definition language (i.e. SGML, XML, etc.). Similarly, the mediator operator may exercise choice over a wide range of data storage tier configurations since such data or information may be accessible from either relational database, object-oriented databases or other content management systems, and may be configured using SQL with RDBMs, OQL for object oriented databases, JDO for either, direct file I/O, or serialization, etc. Some storage architectures may rely upon SQL, OQL, DOM trees, or XML techniques such as)(Forms, XQuery, eXist,)(Path, XFormsDB, or other data access or database extraction techniques known to the artisan. In one embodiment, the capability of processing the query entails generating SQL code that corresponds to the query and utilizing a BQR Mediator to forward an SQL query to appropriate databases (i.e., relational, object oriented, directories, etc.). In the event certain metadata of BCD need to be preprocessed into an SQL query, such preprocessing may be performed, for example, by using a lightweight directory access protocol (LDAP) using database tables.

To satisfy the appropriate request/response messages 105 of the web service 103, the data server 26a can communicate with the information storage device 32 through various local method calls, interapplication processes, or distributed computing protocols (i.e., RPC, HTTP, WAP messaging, XML messaging, WSDL, SOAP, REST, and BPEL, etc.), or in a distributed computing environment through applications sealing (encrypting). In this embodiment, the protocols are extensible to permit secure or encrypted transmissions (i.e., WLM over WAP, WTLS, etc.) and to further employ secure MIME or other security techniques or protocols (i.e. IPsec, OpenVPN security, tunnels, etc.) for attachments to messages, even over mobility networks.

Further, the data server 26a and the information storage device 32 may comprise a distributed web service 103 and communicate through a network, including the Internet, rather than the direct connection as shown below in FIG. 10. The data server may be configured to interoperate with networks, platforms, or databases of a registrant's primary health care provider for PHR retrieval or other external service, particularly when the BQR Mediator is delegated certified access thereto by the registrant or may serve as her proxy. The information storage device 32 can be considered a source from which data is available to the device 18. It will be appreciated that the information storage device 32 could incorporate the data server 26a (or visa-versa) or some other means to facilitate data exchange for the web service 103, if desired. Some databases, for instance, instead may be physically distributed across a network in accessible storage, which may include a registrant's PC or proxy terminal, provided it is "always on" and secure.

I. A WCD Typically has a Client Application that Transmits Transformed BCD or Metadata to the BQR Mediator The application programs 106 (see FIG. 12) of the device 18 can use the processing logic of the information storage device 32, similarly to calling a method on an object (or a function). It is recognized that the client application program 106 can be downloaded/uploaded in relation to the information storage device 32, through the messages 105 via the network 46, directly to the devices 18. It is further recognized that the devices 18 can communicate with one or more web services 103 via the network 46. Also, the devices 18 could be directly coupled to the information storage device 32, thereby bypassing the data servers (i.e. 26a, 100), if desired, provided privacy and security are otherwise controlled. In alternative configurations, functions of the data server 26a can be incorporated into the gateways 15, 24 or the information storage device 32, as described below. In another embodiment, for instance, the WCD runs a servlet or a small server application to provide a BCD extraction service, marshals the BCD into a request-compatible format, and sends the request to the BQR Mediator to instantiate a mediator service to determine if the transformed BCD or metadata, once unmarshaled, may be matched with the template of a registrant, to generate a provisional result set. When identification processes precede the invocation of Biometric Encryption techniques for some embodiments, the identification and verification phases of computation may be harmonized by using the same base source of raw biometric data that is the subject of transformation or abstraction, whether or not the mediator operator chooses to employ common or variegated biometric abstraction processes throughout resolution processing.

6.0 Alternatives

A. Web Services Enabling Mobile Programs to Connect to a BQR Mediator

In general, web services 103, at FIG. 10, have come as a replacement for legacy Browser-based and Client-Server TCP/IP connected infrastructure and applications. Either model, as well as other network-centric models, etc., works fine for this embodiment. Even as a generic machine-to-machine (M2M) communication protocol, web services 103 are becoming a standard for any service-to-service (S2S) model. Based on a set of standard protocols (e.g. WDL, WSDL, SOAP, XML, etc.), web services 103 can provide a platform neutral communication pipe, for example, with messages that are WML- or XML-based, which can support synchronous and/or asynchronous communication messages 105. The network topology of FIG. 10 relates preferably to the M2M model and deals with the BQR Mediator and WCD advancing a web service 103, to enable processing a request with data from some BIIU-compatible terminal device 18.

Referring to FIG. 10, the web service 103 provides the information messages 105 which are used by the client application programs 106 (see FIG. 12) of the devices 18. Alternatively, or in addition, the web service 103 may receive and use the information messages 105 provided by the devices 18, or perform tasks on behalf of client application programs 106 executed on the devices 18. The web service 103 can be considered a software service of the data server 26a, which can implement an interface that in some implementations can be expressed using Wireless Description Language (WDL) or the WAP stack, using a registry for EMR application services, and can communicate through messages 105 with client devices 18 by being exposed, shared, transmitted, or sent over the network 104 through a suitable communication protocol such as the WML over WAP, XML-RPC, XML over HTTP, or ones compatible with data messaging standards such as XML, SMS, Simple Object Access Protocol (SOAP), etc.

B. Messaging Transformed Biometric Data or Metadata Via Conventional or Wireless Communication Device Referring to again to FIGS. 10 and 12, the devices 18 are devices such as, but not limited to, mobile telephones, portable terminals with BIIU compatibility, PDAs, laptops, two-way pagers, page readers (i.e. Kindle™, iPhone™, etc.), or dual- or multi-mode communication devices. The devices 18 include a network connection interface 519, such as a wireless transceiver or a wired network interface card or a modem, coupled via connection 518 to a device infrastructure 504. The connection interface 519 is connectable during operation of the devices 18 to the network 46, such as to the wireless network 24 by RF links or substitutes therefor, which enables the devices 18 to communicate with each other and with targeted services or systems (such as the web service 103) via the network 46 and to coordinate the request/response messages 105 between the client application programs 106 and the web service 103.

The network 46 supports the transmission of data in the request/response messages 105 between devices 18 and external systems, which are connected to the network 46. The network 46 may also support voice communication for telephone calls between the devices 18 and devices that are external to the network 46, such as hospital PBXs. The particular design of the network connection interface 519 within the wireless devices 18 will be dependent upon the wireless communication network 24 in which the wireless device 18 is intended to operate. Beyond ones for General Packet Radio Service (GPRS), the network connection interface 519, may be provisioned to operate with other types of wireless devices and data transmission protocols, such as but not limited to ones of or for CDMA, EDGE, OpenVPN, IP, WAP, wireless broadband, and other wireless networks that the artisan in the field may appreciate.

Referring again to FIG. 12, the devices 18 also have a mobile interface 502, coupled to the device infrastructure 504 by connection 162, to interact with a gateway server (not shown). The user interface 502 includes one or more user input devices such as, but which is not limited to, a communicably connected BIIU. If the screen is touch sensitive, then the display can also be used as the user input device as controlled by the device infrastructure 504. The mobile interface 502 is employed by the EMR using the device 18 to coordinate the requests/response messages 105 over the network topology (see FIG. 10) as employed by one or more client application programs 106 of a client runtime environment 506.

Referring again to FIG. 12, operation of the device 18 is enabled by the device infrastructure 504. The device infrastructure 504 includes a computer processor 508 and an associated memory module 510. The computer processor 508 manipulates the operation of the network interface 519, the user interface 502 and the client runtime environment 506 of the device 18 by executing related instructions, which are provided usually by an operating system and client application programs 106 located in the memory module 510. Further, it is recognized, however, that the device infrastructure 504 can include a computer readable storage medium 512 coupled to the processor 508 for providing instructions to the processor 508 and/or to load, upload, or update either data or client application programs 106 (e.g. sent from a BQR Mediator, peer, etc.) in the memory module 510.

Figure 12:
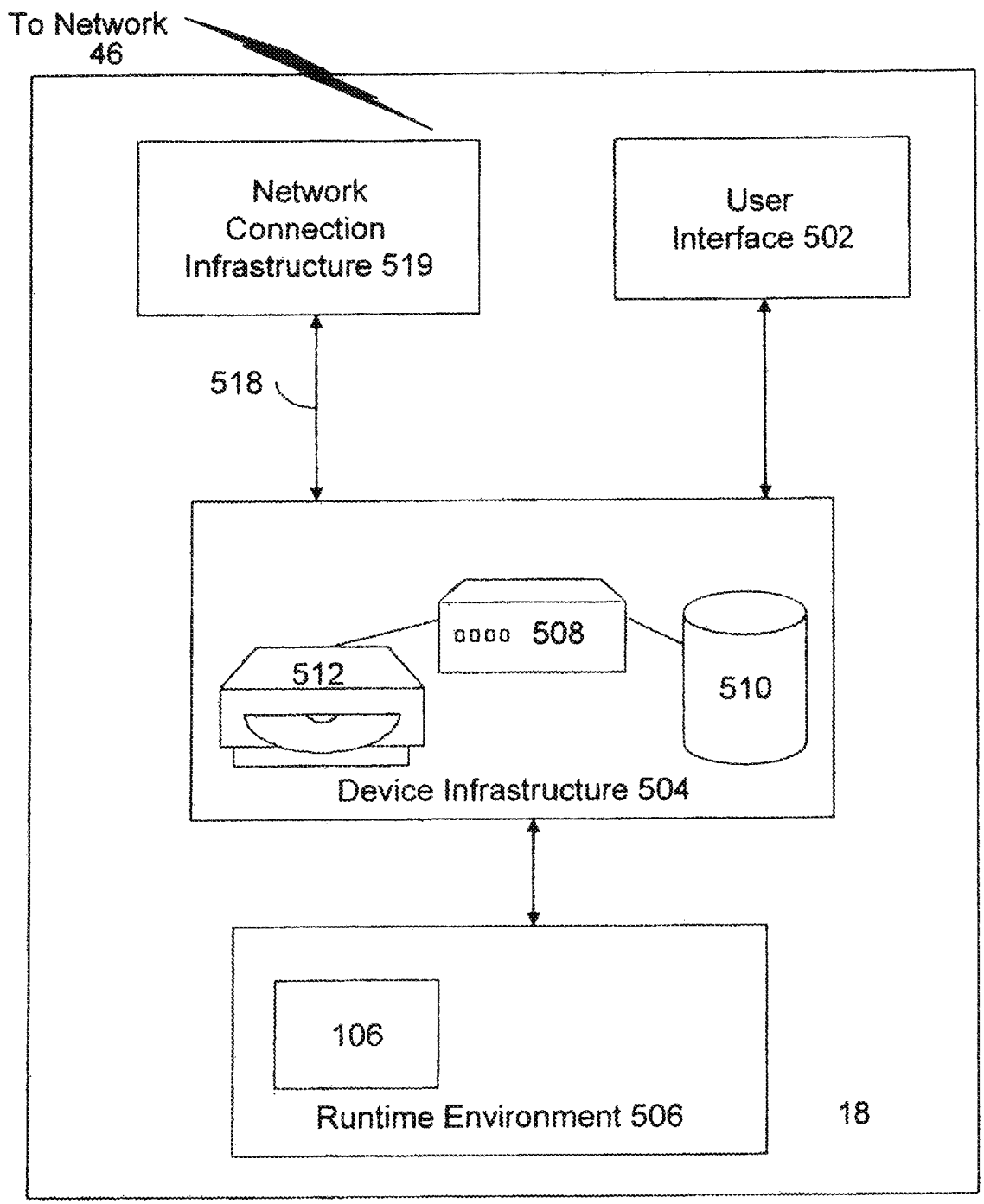
FIG. 12 is a block diagram depicting a mobile device comprised of device infrastructure, a user interface, a runtime environment, and a network connection interface, so that the device may use a client application program communicably connected to at least one network, in accordance with another embodiment of the invention.

Referring to FIG. 12, the device 18 executes the application programs 106 by the client runtime environment 506, which converts the applications 106 into native code, which is executed by a processor 508 in the device infrastructure 504. Alternatively, the applications 106 may be executed as native code or interpreted by another software module or operating system on the device 18. In any event, the component applications 106, including one or more programs to handle EMR tasks, without limitation, such as BCD transformation or metadata conversions, BCD extraction/cancellation, WML/XML serialization, or encryption/decryption programs. Programs are run as needed or directed in the terminal runtime environment provided by the device 18.

Referring again to FIG. 12, the client runtime environment provided by the devices 18 can be configured to make the devices 18 operate as web clients of the web services 103. The client runtime environment of the devices 18 is preferably capable of generating, hosting and executing the client application programs 106 on the device 18. Further, the client runtime environment may support functions that can include ones such as, but which are not limited to, providing access to core object oriented-classes or procedural files/dynamic linking libraries. Examples of the runtime environments implemented by the devices 18 can include such as but not limited to Common Language Runtime (CLR) by Microsoft and Java Runtime Environment (JRE) by Sun Microsystems. Java programs, like program source code written in other languages, that are specialized to perform mediation operations need to be compiled.

C. Deployment Using a Sealed Message Architecture as a Safeguard Against Leakage Referring to FIG. 10, one fundamental concept of sealed messaging is that documents, attachments, or the "messages" 105 are reduced to an encrypted (sealed) representation to alleviate risks of abusive interception in transmission. The figure depicts one of many possible sealed messaging systems. The original encoding syntax for these messages 105 prior to sealing can be entirely arbitrary, so long as the syntax accords to a structured definition language. As such, a sealed messaging system, like the one simply represented in FIG. 10, has far-reaching application, in that it provides a solution for securely adapting Web Services 103, or any other predefined protocol to wireless or other types of open communication links. Sealed messages 105 can be exchanged over any wireless or wired physical pathway with the introduction of a sealed message pipe 30 (implemented over the network 46—see FIG. 10). Messages are often comprised of metadata that is distinct of biometric metadata. Each endpoint 28, 34, data server 26a and device 18 respectively, of the pipe 30 define the boundaries of shared knowledge of message formats or network metadata definitions inherent in the structured definition language, upon which the messages 105 are based.

The structured definition language or SDL (i.e. such as WDL, SGML, XML, WSDL, XFML etc.) can be used to construct the messages 105 as a consecutive series of metadata records, which consist of a number of pre-defined elements representing specific attributes of a resource such that each element can have one or more values. Each metadata schema for web services typically has defined characteristics such as, but not limited to, a stabilized number of elements, a name of each element, and a meaning for each element. Methods using SDL offer a means to formalize document structures in SDL schemas and allows document markup to be validated, using an appropriate parser. Example metadata schemas include such as but not limited to Dublin Core (DC), Anglo-American Cataloging Rules (AACR2), and Government Information Locator Service (GILS). Encoding syntax allows the metadata of the messages 105 to be processed by a device message converter 44 compatible with a sealed serialization service 48, Some customary encoding schemes include such as but not limited to XML, WDL, HTML, XHTML, XSML, XFML, RDF, Machine Readable Cataloging (MARC), WSDL, IDL, SOAP, Multipurpose Internet Mail Extensions (MIME), and S/MIME.

Referring again to FIG. 10, the mediator service endpoint 28 terminates the sealed message pipe 30 facing the information storage device 32. This endpoint 28 distinguishes the boundary at which sealed messages 105 are transmitted to and received from the device 18. The sealed messaging pipe 30 is a bi-directional pathway through which sealed messages 105 flow. The sealed messaging pipe 30 exists between messaging endpoints 28, 34 terminating on the data server 26a (acting as a mediator server 100) and the device 18. The endpoints 28 and 34 are responsible for message 105 conversion and recovery, as described below. The sealed messaging pipe 30 is not necessarily tied to a particular physical or logical network topology, wireless or otherwise, although its benefits can be particularly pertinent to wireless and other mobile-compatible media. The device endpoint 34 terminates and originates sealed messages 105 used by the device 18, or more commonly software applications 106 (see FIG. 12) installed on the device 18. This endpoint 34 shares knowledge of the sealed message 105 format (based on the shared structured definition language) with the mediator service endpoint 28. Shared knowledge enables conversion or "marshalling" and "un-marshalling" of data of messages 105.

Referring again to FIG. 10, the device message converter 44 and the sealed serialization service 48 of the sealed messaging system operate at the opposing endpoints 34, 28 of the sealed message pipe 30. The device message converter 44 and the sealed serialization service 48 have predetermined knowledge of the order and syntax of the descriptors in the structured definition language shared between them. It is appreciated that this predetermined knowledge can be prior to initiation of message 105 transmission, and/or can be an initial component header of the message 105 once received, thereby alerting the receiving party of the expected content format of composition of the sealed message 105. As described above, the device message converter 44 and the sealed serialization service 48 have knowledge of the original message 105 format, and the converter 44 and the service 48 operate by removing or restoring overhead information. Therefore, endpoint 28, 34 mapping and unmapping operations are matched, and the original message format is predefined and predictable.

Referring to FIG. 10, the device message converter 44, exists on the device 18 to integrate sealed messages 105 with the device 18. The device converter 44 can be implemented as software in the runtime environment 506 (see FIG. 12) of the device 18 and/or can be part of the operating system of the device infrastructure 504. It is recognized that the device converter 44 could also be implemented as hardware, or as a combination of hardware and software. The device message converter 44 either passes sealed messages 105 to other systems or software applications 106 on the device 18 or first converts the sealed messages 105 back into the original message format associated with the information storage device 32 (see FIG. 10) messages and then passes the converted messages 105 to the other systems or applications 106.

Referring again to FIG. 10, the mediator server 100 is a component in the operation of sealed messaging system. FIG. 10. The mediator server 100 provides the pipe endpoint 28 that is exposed to the information storage device 32 for delivering sealed messages 105 to the device 18. The mediator server 100 has the sealed serialization service 48, which maintains a set of application maps that allow original message formats, preferably multiple message formats for a variety of structured definition languages, such as but not limited to WML, XML, SGL, (i.e. via XML-RPC or Simple Object Access Protocol (SOAP), etc.) to be sealed and transmitted to the device 18 as messages 105.

Referring to FIG. 10, the sealed serialization service module 48 of the mediator service 103 transforms messages 105 received from the information storage device 32, expressed in an information source format, into sealed messages, and vice-versa. An encryption/decryption module 54, which itself may be distributed, performs the seal/open translation of the messages 105, and the application maps hold mapping information for conversion of sealed messages 105 to and from defined message formats associated with one or more information sources 20 communicably connected to the mediator server or information storage device/database 32, which can include a number of different structured definition languages. The application maps provide a means to allow pluggable support for encoding/decoding of an arbitrary number of message formats, and this may include support of encryption and decryption of messages or attachments.

Referring to FIG. 10, one example of a sealed messaging system is depicted, which is compatible with certain embodiments, and said system enables transmission of WML or XML messages 105 between the information storage device 32 of the web service 103 and the wireless device 18. In this context, the mediator server 100 runs as an WML/XML server and the wireless device 18 operates as if running an WML/XML client, such that the message pipe 30 communicates a sealed message 105 based on shared knowledge of the WML/XML metadata descriptors (i.e. the shared structured definition language), both sequence and meaning, of the WML/XML syntax. In one embodiment, referring to FIGS. 10 and 11, the mediator server 100 invokes mediator data structures 101 and mediator procedures 102A and 102B, to control the web service 103, to produce a result from the query transmitted over a secure wireless network 104, and communicates via sealed message 105, with one or more client application programs 106 operated on a device by an EMR.

The mediation processing unit 100 plays a middle-man role, and here also may use native or non-native resources or files. It may use such resources, for example, to manage encryption and decryption keys, to control network access, to modify network architecture dynamically, to delegate tasks to facilitators or middleware, to add, join, or logically organize storage systems into databases or other base resources, etc., so as to optimize response quality or timing by enabling source mediation, query mediation, process mediation as well as secure network connectivity mediation. Referring to FIG. 5, the resolution server 87 may update the list of eligible BCD techniques as they improve, and the authentication server 86 may permit authentications for new WCDs or EMRs, etc. The registration server 85 may use an optional data entry interface to support authoring profiles or editing of personal health records by registrants, the mediation server 100 may secure data imports, or the work-flow controller 83 of a mediation service manager program 23 may invoke sequence instructions, handle BCD-oriented data, analyze, associate, sort, filter, match metadata, or resolve data from storage device 32 to generate policy- or rule-compliant results or package them into responses for export. Some registration servers 85 or other processing units may be provisioned by using Web Services, Service Oriented Architecture, Semantic Web techniques,) (Forms, XQuery, XPath, XPatterns, XFormsDB, or REST, as needed, if privacy is not compromised.

When the ownership and control of both a mediation server and database reside under the dominion of the registrant's primary health care provider (i.e. under a license, etc.), for instance, fewer provisions may be required to use one or more of the methods than when the BQR Mediator is not the administrator of the database. The method may be configured to enable the registrant to ask in advance for his or her primary health care provider, or a specified proxy therefor, to extend its privacy policy to certain classes of authenticated requesters automatically, if the latter are authorized. The mediating service provider and the content provider may consolidate, split, or share a variety of roles in an end-to-end service realm. Unlike when the content provider and the mediation service provider are the same entity, when they differ further safeguards may be appropriate to secure data or content, especially if an operator of a BQR Mediator is not sufficiently trustworthy to access the profile or PHRs from a registrant's viewpoint. In the latter context, the content accessible to the latter BQR Mediator may necessarily need to remain opaquely packaged, encrypted, or transcoded, until the response is decrypted by the requester.

In some embodiments, a query using a BCD-derived string may be initiated for identification or verification, or both; and these operations may be supported by the BQR Mediator separately or consolidated into one. These embodiments confirm that private profile retrievals via mediation may be associated with extremely high security. Some federated arrangements may entail process mediation, iterative instruction loops, or the composition of semi-autonomous intelligent self-organizing systems or networks. Some response-inclusive deployments may simply rely upon conventional enablers. The extension of networks to public monitors would usually be provisioned and deployed under mediator policies on privacy or anonymization, as well as security. Others may run similar applications or XML Data Management Servers (XDMS), either with or without using software or protocols with proprietary extensions. Different architectures of system components and ownership/control variations of resources and lines of demarcation may widely vary across implementations, and even do so dynamically, but the functional uses of the mediation framework to advance rapid health support services, described herein may remains in tact.

D. BQR Mediator may use distributed computing to harmonize internal or external provider service models, with registration services, request service models, security policies, or ontologies, as needed.

Registration is a subroutine, module, process, or service that is included in some embodiments but not others. More specifically, data communication permits the registrant 40 to use one of many ways to register data (i.e. directly, indirectly, by guardian, client program, via privacy-oriented third-parties, programmatically, etc.) in a prompt, time-sensitive, but asynchronous manner. Data communication and interaction permits the registrant 40 to engage in mediation activities in situations where voice-based communication alone would be impracticable, inappropriate, or both. Voice communications alone is ill-suited to self-submit or retrieve text, metadata, files, image data, links, or structured data or other machine-readable files, or pointers thereto. Through the use of data communication, the registrant 40 may engage in registration or BCD pre-testing phases in a non-disruptive, asynchronous, or interactive manner by responding in a digital format to prompts of the mediator server directly or via other information channels generated or presented in a digital format.

When registration is performed on an database or service external to the BQR Mediator, as by an public or private entity unaffiliated with the mediator operator, the BQR Mediator may correspond interoperably with the external service when the automated privacy and security officers of each computing domain are in accord with one another.

Resolution tasks or acts may be distributed over the network (i.e. between client and server applications, or between peer server and server, etc.) by using request-response messaging also. Irrespective of the choices as to open or closed compositions, the logic layer of one configuration may consolidate an identification and profile request. One may generate a result set responsive to a request to only identify the otherwise unidentifiable individual if registered. One may only verify the link between a tentatively known identity and a profile, which may be retrieved only upon verification of identity. Similarly, A BQR Mediator may deploy a wide range biometric representation-oriented matching techniques with or without image analysis, and with or without multiple band filters. Some biometrics are more widely acceptable and easily captured when an individual is unconscious. When using fingerprint data, typically, some choices by system integrators, among techniques of image analysis, statistical probabilities, or artificial intelligence, may entail, for example, one or more of the following: biometric encryption templates, two-phase or n-phase examination using one or more classifications approaches, indexing techniques, or segmentation rules, to process or prepare for verification, candidate list ranking, matching, or other operations to advance resolution. Other biometric modalities each offer a separate array of approaches.

Another embodiment allows the registrant's records to contain data, cross-references, hyperlinks, or network links to data entries for any fields of data. For instance, text data, may be normalized using either structured or semi-structured data or compatible formats (i.e. text only, WML, XML, SOAP, RPC-XML, etc.). Another embodiment relies upon use and reuse of formal ontologies, preferably of the OWL DL variety (i.e. SNOMED CT, SNOMED RT, Clinical Terms v. 3, NCI Thesaurus, etc)—in general—and the adoption of a formal, common, upper ontology, in particular (such as one which could be developed through the mapping of the HL-7 RIM into SUMO or Protege). This embodiment favors the use of standard formal representation languages (i.e. Ontology Web Language [OWL], OWL DL, OWL-S, RDF, WSMO, and Simplified Common Logic, etc.). The ontologies may be of particular utility not only in performing remote diagnosis, but also in compliance with registrant directives that are formulated in the conditional based upon a range of vocabularies.

One approach to secure wireless network administration may entail combining RADIUS Server with AES, and using WPA-2 or 802.11i configurations, where every component that is connectable is compliant with such standards. While wireless security often poses a special series of serious challenges, especially across multiple emergency service areas, the BQR Mediator may conscript into its service any conventional methods and standards as may be deployed for each of the several kinds of networks, or combinations thereof, that may be used (i.e. GSM/GPRS, IPv4, IPv6, WLAN, Ethernet, access networks, other wireless networks, etc.). Many new solutions are also conducive to securing wireless transmissions, message flows, or request/response patterns, not otherwise widely known as compatible with this set of new methods of resolution mediation. See e.g., RFC 4942, 4891, 4718, 4621, 4555, 4481, 4225, 4140, 4068, 3963, 3776, 3775 (basic), 3753, and RFCs that are the progeny of any of these (collectively "RFCs"). Another embodiment may be configured using DIAMETER (RFC 3588) as a network protocol for AAA, and also is conditioned to be compatible with the Diameter Policy Application as described in RFC 5224 (March, 2008), or updated X.509 standards.

In one example, locator functionality or geo-tagging of EMR requests can be provided also, in whole or in part, by the mediator using a WFC 83, definition files, and a central registry 82, with a location application, hereinafter collectively "a location server." The location server may communicate with mobile devices via one or more wireless networks 114. Again, any mobile electronic device can provide or invoke Web services via the location server, using the wireless network 114, as represented by generic device 18A at FIG. 11.

Another embodiment provides a reliable and intelligent software-custodian of biometric records, even if unattended by any human (i.e., human privacy officer, etc.), which can use these technologies for personalizing and customizing emergency medical responses, with multilevel security protection (i.e. hardware, operating system, network, authentication, failover, etc.) and extended privacy at least over dual confidentiality interests of the registrants in personal biometrics and profile data. The mediator's process management software implements a multilevel strategy to protect the BQR Mediator by relying on wireless network firewalls and certain benchmark standards of the Center for Internet Security and encryption with WiFi Protected Access (WPA/WPA-2).

7.0 Other Optional Features

A. Features May be Extended Optionally, Beyond Core Functions of the Method

The composition of a BQR Mediator varies under an open biometric approach to permit configuration choices by mediator operators, rather than an approach that dictates any exclusive BCD technique. The BQR Mediator may use a protean framework that is variable during design time, but will favor clear and authoritative recommendations at runtime as to resolution processes for designated BCD modalities. The mediator operator has several choices as to BCD sources, techniques, measurement, sampling, encoding, encryption, reduction, transformation, abstraction, metadata translation, cancelability, compilation, combination, distribution, emulation, or composition. The consistency across federated BQR Mediators, or external corresponding services, may be promulgated by service, process, or geographic market, or any other suitable basis, as desired.

By running specialized software, a mediator may deploy a new logic layer of a server system, so it can process distinct kinds of queries in at least one of several scenarios. One scenario may entail, for instance, a request by an EMR where a possible registrant is unidentifiable without preliminary inquiries to the mediator. Another scenario might entail an EMR's request that concerns an identifiable registrant, but where the mediator is not trusted to read the plaintext content of the registrant's profile. Sometimes a mediator will be queried to resolve to an appropriate result set at least partially from BCD metadata that represents a transformed biometric sample, or from a PIN derived therefrom. In some configurations, the mediator may need to rely upon the logic or instructions in the software to identify a registrant either between receiving an authentication assertion and compiling authorized data, or otherwise as described above.

Parenthetically, those who are designing or implementing mediators have the choice to leverage certain new interoperability standards as well, which may also extend to reliable privacy and security at a threshold not weaker than current best practices of AAA. See also, RFC 4962 at pp. 20-21. Some earlier techniques were built upon the self-authoring model of the web, analogously using network interoperability standards. Some other conventional techniques also indicate how to couple a practice of self-submittal of records for registration with third-party verification of an identified person, to permit matching so as to ascertain consensual access (i.e., for downloads, payments, or editing, etc.) to a registrant's data.

As long as a registrant's raw biometric data is neither transmitted to, nor stored on, the side of the network communicably connected with the server system, any BQR Mediator operations of processing, resolving, associating, matching, encrypting, or using a representation of biometric data or a substitute therefor may be performed on either the client-side or the server-side of a network, or anywhere therebetween, which again may be comprised in whole or part of a secure wireless network, WLAN, or an enhanced mobility network. For example, a mediator may transmit a servlet to emulate the server on the WCD or remote terminal. Mediation hubs of biometric-driven information, like interchange hubs for modes of transportation, commonly galvanize data into information while enabling adaptation, reuse, and growth across autonomous new sources, new means of secure transport, or new participants.

A BQR Mediator that is enabled to apply compounded techniques for a thumbprint, for example, might process metadata from transformation or abstraction techniques using two or more forms of image-analyses either based upon minutia-based, gray-scale, ridge patterns, orientation, scaling, finger code, minutia triplets, Gabor filters, or combinations, etc. Other biometrics may further use Fourier transforms, Daugman's IrisCode, wavelets, eigenfunctions, or sequences, etc. Using a single biometric source, the BQR Mediator may resolve queries by applying indexing, segmenting, or filtering mechanisms to identify the right registrant and generate a link to his or her profile. It may optionally entail multiple indexing techniques of the same transformed biometric sample to narrow down eligible candidates to be matched later, so as to expedite a matching process.

Error reduction in the biometric arts may often be attained with combinations of biometrics or of cancelable biometrics from the same or different biometric sample. Still other transformation or abstraction techniques may use a different finger or thumbprint, than the one that is used to descramble secret data from a later provided biometric encryption template or other biometric source. Still other measures for assigning metadata to transformed biometrics or initial transformation techniques may use abstraction techniques derived from unrelated or discrete sources of raw biometric data (i.e. face, iris, hand configurations, or fingerprints, etc.). The performance specifications may also vary depending upon the quality of the enrollment data. Some embodiments will support a set of Registration APIs. In the context of generating metadata to disambiguate registrants by their fingerprints, for instance, the master raw biometric sample, notably, is typically accrued through compiling, compositing, or collating of multiple passes or biometric templates both at enrollment time and at the time of identification or verification. See e.g. Peter Wrage, U.S. Patent Application 20060177113, Method and apparatus for determining a stable repeatable code from biometric information (Aug. 10, 2006). The implementation of selected biometric techniques for verification will generally be constrained to some subset of configurations compatible with the biometric techniques deployed at enrollment to register biometric data.

B. Mediation may be extended using networking conventions, security standards, interoperability techniques, even with wireless facilities while maintaining security safeguards.

Like other Web services, mediation services may execute over an IP network other than the Internet as well. An IP network transmits and receives packet-switched messages from one address in IP network to another address. IP network may comprise any number of available packet-switched networks and use IPsec. IP network may, for example, comprise a Local Area Network or a Wide Area Network. An IP phone and a workstation may also be coupled to IP network. An IP network may also be coupled to an external data network such as Internet, an WLAN, CDMA/EDGE network, a UDP network, GSM/GPRS, Ethernet, WAN, WiFi, WiMAX, VPN, OpenVPN, TDMA, radio, ISDN/PSTN, or to an external voice network like a public land mobile network (PLMN). Security considerations for coupling IP and non-IP networks may require the use of special security protocols, tunnels, stacks, gateways, packet filters, routers, route optimization programs, and other software. See, e.g., RFCs.

Some embodiments may entail interoperability beyond the primary health care provider of registrants, which ensure security and privacy. For example, some configuration choices include federations that may also blend private medical care response features with public health functions like emergency notification, etc. Preferably these federations would be designed to share data with publicly affiliated servers compatible with AAA best practices or some equivalent and transparent customary rules. Many existing or new public health databases could readily be verified as, or upgraded to become, compatible with the best practices of AAA, as specified in RFC 4962. Once vetted and upgraded for compliance on security and privacy standards, these public health databases could include without limitation U.S. federal health networks, CDC or NIH resources or servers, domestic or foreign pandemic monitoring services, servers or databases [like GPHIN], local or state agency server systems, as well as the Department of Homeland Security's mass casualty database, and other public health resources, etc.

In the case of more scalable configurations of one of the methods using multiple servers, the servers or nodes may be tightly integrated, federated, or loosely coupled, for instance, to form a network of interoperable server systems. Such a network may be global, national, regional or local. A plurality of servers may alternatively be used autonomously as silos, perhaps each dedicated to one locality or region, at the risk of limiting access to EMRs or registrants outside their usual geography. For instance, mediator operator preferably would log and publish statistics or quantification data that transparently reflects network performance, cryptographic reliability or risks, or other analytical processing constraints or metrics. Analytical parameters include accuracy levels, error rates, or rejection rates of biometric processes, transformation techniques, classification conventions, or algorithms reliability. For any claimed methods that extend to require transparency as to performance specifications, that requirement would promote optimizing the alignment between performance factors and expectations as to privacy and security by actual or potential operators, requesters, or registrants. The imperative of mediator operators for continuous optimization of the grade of service, especially for accuracy and reliability is ordinarily intensified through transparency.

Since automation can rarely settle all questions of access, preferably all instances where automated rules are inadequate are displayable to a human privacy officer for a higher-tier evaluation. The human privacy officer is advised when the rules indicate a possible violation or an appeal for an exception, and can, if appropriate, override the rules and permit release of any or all the profile content or health information requested. Having a human in the loop to deal with exceptions also provides a mechanism for dealing with unusual emergencies in a disciplined way, which is certainly preferential in certain known, unknown, or unknowable medical or urgent care situations.

For instance, an authentication rejection during a civil disaster due to some improper failure to authenticate (i.e. both the device and EMR separately, etc.), may in some circumstances be modified by human intervention that beneficially overrides the BQR Mediator's default rules. This could occur, for example, when a known EMR partner calls, on voice or data lines, who has no choice but to use another's device due to the critical situation like the usual custodian's disability, and this exception passes human scrutiny. Preferably some compositions include an interface to contact the mediator operator's supervisory privacy officer, as needed. The BQR Mediator also may provide a log so that patterns of either too stringent or too liberal policies can be recognized and the rule system can be adjusted accordingly.

Different embodiments of the BQR Mediator may include a user interface schema that deploys different designs as well (i.e. to disambiguate WCD inquiries from registrant access, or differentiate Registration APIs from Query APIs, etc.). For Query APIs, the sequence of the request data in a request, in some configurations of the BQR Mediator, preferably determines the structure of the instance of mediation application that is invoked, and the structure of the query processed preferably determines the function of the BQR Mediator in relation to the request. The level of trust required or associated with various methods using authentication, or the legal context surrounding a method, for example, may be governed by the security needed (i.e., high protection usually for private systems or services with highly confidential data to low protection for public systems without confidential data, etc.). Some of the embodiments are extensible to accommodate the adaptive authentication variability. Among these, no authentication at all may present an elegant runtime or design-time solution for some operators, but it is a configuration choice. It may alternatively be delegated to the registrants to chose the appropriate level of authentication security they prefer in some implementations, or at least within a designated range of levels.

In another embodiment, to enable query mediation, the BQR Mediator processes EMR requests by detecting if the request contains (a) a name and PIN of a registrant, or if not, (b) a transformed BCD and name, or if not, (c) a transformed BCD only, or if not, (d) a name only. Under (a), the BQR Mediator substantiates the name by processing a result set with a name, photograph, and profile. Under (b), the BQR Mediator substantiates the name by processing a result set with a name, photograph, and profile. Under (c), the BQR Mediator identifies and substantiates the registrant's identity by processing transformed BCD or metadata into a result set with a name, RSI, photograph, or profile. Under (d), the BQR Mediator substantiates the name by processing a result set with a photograph, and upon follow-up request that is specially authenticated, processes a result set for the profile that matches the name, if any.

The BQR Mediator simplifies mediation with persistence to bridge the temporal divide or interregnum between the time that a registrant submits, composes, enters, uploads, or completes a profile with any directives for entry into accessible storage and the time that an EMR makes a request. The processing method of resolution mediation anticipates the need to release certain non-private data with limited confidentiality by submitting the query and retrieving the results. In one embodiment, the BQR Mediator accordingly stores instruction that enables a processor-based system, composed of a plurality of terminals connectable to a network that is at least in part a secure wireless network, to resolve a data query that contains transformed biometric data of one person by comparing the query data with prestored files with some similarly transformed biometric data of a plurality of persons enrolled in a network-accessible database. To execute a query, the specialized software provides the search command to database that contains said prestored data of a plurality of persons. The database generate a result set derived from the comparison, to enable generating a result set that refers to personal information of one person whose prestored data resolves the query.

Another embodiment of a method of mediation, that deploys transformed BCD or metadata as a key to identify registrants, entails another convention of personally notifying one or more EMRs when an individual is a registrant of the BQR Mediator without any mediated automation. Some embodiments, to the contrary presume, that an EMR would scan BCD of a patient or victim as a part of a prevailing community custom or practice. The use of a mediation process, however, may not be enshrined immediately or ubiquitously as the default practice or custom to reduce BCD into metadata for resolution. A notification convention, accordingly, may become useful to extend the BQR Mediator's use, especially to bridge any transition interval until such early detection of the BCD becomes ensconced as a customary default practice among EMRs in the industry or in a geographic area.

Notification or other resolution mediator mechanisms may also serve to permit mediation to enhance, or operate as a complement to, other health websites or mobile emergency medical care platforms. Such notification conventions may comprise enabling the displaying or affixing a distinctive symbol, insignia, or device (notifier means) to show participation as a registrant. Such notifier means, for instance, may be attached to the person's keys, ring, wallet, driver's license, Real ID card, mobile phone, bracelet, vehicle dashboard or tail light, necklace, pendant, dog tag, fingernail, skin, ring, eyeglasses, handbag, purse, shoes, belt, or other location, accoutrement, or place conspicuously. Alternatively, a notifier worn by a registrant may be inverted so notifiers are to be worn solely by those who expressly opt-out of participating.

In other embodiments, such a mediation method may be a capability or component of a broader framework, process, health services, or business method. The mediation methods may offer resolution services or PHR access, and premium services in transformed BCD use, such as notification, logistical or triage services, health news, medical information, ancillary health support services, or access to enhanced personalized information, hyperlink-extended PHR files, certain documents or directives, or qualified third-parties' data on the registrant. Similarly, these or certain other services may be offered on a graduated schedule of subscription fees, which may include some free services.

Because these servers and communication networks may be disrupted, another embodiment will apply failover techniques at one or more levels of processing, failure mode recovery at one or more layers of network node topology or sets of protocol of communications.

Instruction sets for query processing may use algorithms suitable to various tasks that depend upon the composition of the BQR Mediator or its configuration. For many, but not all, of these approaches there must be compatibility of certain logically or conceptually paired algorithms, with respective applicability at enrollment time and query time.

Otherwise, in some configurations, performance or privacy may be jeopardized without the use of compatibly paired algorithms, or when any pair requires interdependence between scrambling and descrambling algorithms, but the linkage is disrupted. In certain cases, for instance, when one is neither symmetrically or asymmetrically paired, nothing will promptly suffice to descramble the registrant-specific identifier, associate data, or match transformed representations. In the event the database includes an ontology of biometric abstraction models, which can rely upon various kinds of algorithms (i.e. that may advance image analysis, Gabor band pass filters, Daugman's IrisCode, or vector translations, etc.), the resolution processing may comprise executing a query to extract database information for making a rapid determination as to which, if any, of a very large number (i.e. millions, etc.) of samples, within one or more kinds of biometric abstraction models, and within a searchable database, exhibit a desired level of similarity, as compared to a target biometric abstraction model. See also, Wendt, U.S. Pat. No. 6,895,104, Image Identification System (May 15, 2005).

While a multitude of applications that perform analysis, classification, indexing, and other programming techniques are available that may effectively split, divide, multiply, or redirect one or more subsets of queries based upon either computational techniques (i.e. using Java, C++. C, or another programming language etc.), query categorization, sequenced processing approaches, or other techniques, these approaches and others are now largely interchangeable by the artisan, and may be encompassed under the rubric of logic layer applications. The logic layer subsists of one or more resolution applications that form a conceptual building block, but is not necessarily monolithic in character or composition. See, e.g., Hsieh, Ming, U.S. Patent Application No. 20060104493, System and method for fast biometric pattern matching (May 18, 2006). Similarly, query resolution processes that use the same instruction set for both identification and verification, are fulfilling discovery functions of a logic layer building block also, since the logic layer of a BQR Mediator denotes the availability of preprocessing, processing, or post-processing operations, as needed, for either separate or consolidated resolution to perform identification, verification, or both In contrast, many other health website or system operators would have registrants incorrectly believe the operator uses methods that are secure when either it is an untrustworthy entity, an entity that fails to require compliance with current best practices of AAA, fails the leakage-free test of storage or transmission, fails to rely upon a trusted authority that authenticates requests and certifies the privacy and security of sensitive personal data, manages private data in a way that fails to reduce the actual or potential material risk of the operator's (or its correspondent's) conflict of interest, or provides access to some registrant's sensitive information other than the health data such as a registrant's IP address, without registrant authorization or consent to collection, access, use, or onward transfer.

While less than five percent of physicians use fully function electronic record systems today, the building blocks of technology may be composed by mediator operators to enable registrants to anticipatorily improve their remote health care support, consistent with their personalized needs and privacy constraints. Even though the standalone electronic medical systems of hospitals are still largely composed of stand-alone silos, and even though when patients walk out of hospitals none of that data flows with them, the new methods permit just enough mediation to create a mobile resource driven by biometrics so that selected data does follow them to extend a safety net when beneficial for rapid care assistance.

These embodiments exemplify only a few of the implementations of the invented mediation method of resolution in the context of improving timely access to personalized or customized medical information for identification or profile data. Some extend the method to enable requester access to a registrant's self-submitted content in a result set. Some extend the method to be compatible with other wireless request methods. Some extend the method to support advancing a registrant's self-administered privacy rules. Some extend the method to ensure security, multilayer security, or variable security platforms for different networks. Some extend the method to add a response capability beyond result set generation, by augmenting the request/response messaging acts or subroutines. Some extend the method beyond solely trusted computing domains or to environments across mobility networks. Some extend the method to ensure against failover or provide failure mode recovery. Some ensure alternative de-identification safeguards of BCD using biometric abstractions, cancelable BCD techniques, or permit lower error risk using compound BCD techniques, or both.

Further, some extend the transformed BCD resolution in these health care contexts to method of blocking databases from completing result sets, that might otherwise be realized from transformed BCD or metadata resolution either at a preprocessing, processing or post-processing stage. Some use a rules database that comprises a rule that excludes from a result some portion of stored data associated with the individual if said portion of the data does not satisfy all rules applicable to said portion of the data. One example of such a constraint arises if there is a rule to exclude all personal information from a result if a requester's service model is incompatible with every accessible providers' service model. So, some portion may include all.

Further, some extend the method by combining one or more of these extensions together, or employing other techniques, methods, devices, means, apparatuses, products, standards, components, software, hardware, network facilities, or communications capabilities. Operational specification may also extend to performance specifications or quality of service criteria like reduced rejections, errors, or grade of service parameters, etc. The invented methods encompass these described variations as well as other ways to make or use a BQR Mediator not described, but that come within the know-how of the artisan of ordinary skill in the field.

Conclusions, Ramifications, and Scope

Accordingly, the reader will see that, according to one embodiment of the invention, I have provided methods using mediation software for rapid health care support over a secured wireless network. While the above description contains many specificities, these should not be construed as limitations on the scope of any embodiment, but as exemplifications of the presently preferred embodiments thereof. Many other ramifications and variations are possible within the teaching of the various embodiments. For example, the BQR Mediator may use data or process mediation software to identify or verify registrants by interchangeably deploying various biometric abstraction models or message patterns to resolve queries to either produce results or enable transmission of responses to the requesting applications. By using one or more kinds of secure wireless network, the remote requests may support a mobility network while, in some cases, extensibly utilizing the resources of local or external services for data, process, or protocol mediation to expedite rapid health care support via secure wireless network facilities. Thus the scope of the invention should be determined by the appended claims and their legal equivalents, and not by the examples given.

The invention claimed is:

1. A non-transitory computer-readable medium storing instructions executable by at least one processor, the non-transitory computer-readable medium comprising: at least one instruction to compatibly facilitate associating a transformed recognition biometric, that was irreversibly derived from a live raw biometric of an individual, with a transformed reference biometric that was stored, within a predetermined tolerance, for biometric identification over at least one wireless session securely.

2. The non-transitory computer-readable storage medium of claim 1, wherein at least one stored instruction when executed is also operable to authorize access to a wireless device, which transmits a message comprising said transformed recognition biometric, and wherein said wireless device is communicably connectable to said at least one wireless network via an Authentication Centre (AuC) and its associated Home Location Register (HLR), to enable processing subscription data of said wireless device for access over a serving network.

3. The non-transitory computer-readable storage medium of claim 2, wherein at least one stored instruction when executed is also operable to enable a node of said serving network to receive at least one SIP INVITE from said wireless device to establish a session, and wherein said AuC communicates only with its associated HLR to use the data needed for authentication and ciphering from the AuC, wherein said AuC uses services of a 3GPP AAA server to initiate a session to facilitate biometric identification by comparing said transformed recognition biometric securely.

4. The non-transitory computer-readable storage medium of claim 1, wherein at least one stored instruction when executed is also operable to authorize a wireless device to request access a serving packet switched network so as to transmit at least one message comprising an attach request, and wherein said at least one wireless network comprises a node of a EUTRAN that relays back to said wireless device an attach reply from an LTE network that allocates emergency bearer services for conducting a supervised remote biometric identification on behalf of said individual, to enable personalized rapid healthcare support.

5. The non-transitory computer-readable storage medium of claim 1, wherein at least one stored instruction when executed is also operable enable a wireless device to (i) discover an accessible IP network inside the home public land mobile network (H-PLMN); (ii) transmit an attach request over at least one wireless access channel, and (ii) enable said attach request to be processed by a Home Subscriber Server (HSS), which selectively controls access across the signaling plane of said H-PLMN by using subscriber and location data, to return an attach reply provide said wireless device access stored transformed reference biometrics securely.

6. The non-transitory computer-readable storage medium of claim 1, wherein at least one stored instruction when executed is also operable to (i) verify that said transformed recognition biometric is application-specific so as to facilitate a supervised remote biometric identification on behalf of said individual; (ii) authorize a wireless device to transmit data securely over said at least one wireless network, which is communicably connectable to a packet data network, and (iii) and enables an application server to generate output that provide biometric identification, wherein said that transformed reference biometric was stored during a prior encounter by said individual in case of an uncertain event.

7. The non-transitory computer-readable storage medium of claim 1, wherein at least one stored instruction when executed is also operable to initiate an emergency session using a Packet Data Network Gateway (PDN GW) and access to retrieve individual-specific health information via a 3GPP wireless access network using roaming architecture of an LTE network for local breakout with visited operator's application function only.

8. A system that transforms a serving network, already configured to interoperate with heterogeneous wireless access networks, by integrating biometric identification into a gateway of said serving network, said system comprising: a gateway communicably connectable to said serving network, and a processor, communicably connectable to said gateway, wherein said serving network is configured to manage packet routing, and said system executes at least one instruction to expedite biometric identification to support personalized rapid healthcare for a wireless device.

9. The system of claim 8, wherein said system also execute at least one instruction operable to detect that a communication from said wireless device comprises an attach request from a wireless device for emergency bearer services and enables processing an Emergency Access Point Name (APN).

10. The system of claim 8, wherein said system also executes at least one instruction to process an attach request without an APN from said wireless device that seeks emergency bearer services as an indication, when the HSS does not provide an Emergency APN in subscription data, that a Mobile Management entity (MME), must provide a default Emergency APN to process the emergency connection.

11. The system of claim 8, wherein said system also executes at least one instruction, upon detecting that said wireless device is a visiting said serving network, to set up a session within the area of the visited public land mobile network (VPLMN) for IMS Emergency Session Support by using roaming architecture for local breakout, with visited operator's application functions only.

12. The system of claim 8, wherein said system also executes at least one instruction to initiate an emergency session using a Packet Data Network Gateway (PDN GW) and access to retrieve individual-specific health information by using a packet data network with a trusted 3GPP wireless access network.

13. The system of claim 8, wherein said system also executes at least one instruction to initiate an emergency session using a Packet Data Network Gateway (PDN GW) and access to retrieve individual-specific health information over an non-3GPP access network for an untrusted connection, if the serving PLMN, can route data through an ePDN using PMIPv6 and tunneling consistently with authentication.

14. The system of claim 8, wherein said system that executes at least one instruction to also detach a default bearer services of said wireless device, wherein at least a portion of a communication from said wireless device also comprises biometric-derived data from a wireless application, unless said at least a portion of a communication also surmounts an access control rule consisting of at least one of the following: (a) validation that a network channel traversed by said at least a portion of a communication was wireless in at least one part; and (b) validation that said at least a portion of a communication was from an application, other than one invoked by the individual who is the subject of the request.

15. The system of claim 8, wherein said system executes at least one instruction to receive said data of a request over said serving data network wherein said request comprises a query with biometric-derived data from a wireless application, and at least one instruction to validate said request for biometric identification if said biometric-derived data of said request is consistent with at least one biometric abstraction model recognized by said system.

16. A method performed by an apparatus of a network entity, the method comprising:
   receiving, at said network entity, a request that is transmitted over a wireless access network from said wireless device;
   controlling at least one session of a serving network, which enables securely transferring data of said request for biometric identification, to support personalized rapid healthcare; and
   comparing at least a portion of a transformed recognition biometric data of an individual, which was irreversibly derived from a live biometric sample collected by a sensor integrated with said wireless device, with a transformed reference biometric that was previously stored during an earlier encounter, by using inexact matching, within a predetermined tolerance.

17. The method of claim 16, wherein said request also comprises an attach request to establish an emergency session to permit said inexact matching to attain a key specific for said individual, wherein said transformed reference biometric was stored in case of an uncertain health event, and wherein said network entity operates compatibly with a mobility management node of said serving network to at least partly control the signaling of said at least one session.

18. The method of claim 17, which also comprises attaining said key identifying said individual, and permitting said wireless device to use said key to retrieve of at least one data element of the health profile of said individual from a database consistently with any constraining rule of said database; wherein said any constraining rule comprises at least one rule that excludes from said result any portion of stored health profile associated with the individual if said portion does not satisfy all rules applicable to said portion.

19. The method of claim 16, which also comprises ensuring that said network entity is communicably connectible to a Mobility Management Entity (MME) and to a Server Gateway (S-GW) of said serving network, which comprises and LTE network that coordinates the IP bearer server parameters to enable retrieving information comprised of intermodal content over a packet data network (PDN) via a Packet Data Network Gateway (PDN GW); and wherein said MME also supports bearer controls, selection of said PDN-GW, and a request for PDN connectivity.

20. The method of claim 16, which also comprises supporting roaming by said wireless device, and provisioning said network element to operate compatibly with at least one MME of a visited public land mobile network (VPLMN) to utilize a PDN GW, which exchanges data with a V-PCRF node, to permit access over the Visited Operator's IP Services, and transmittal of an identifier attained by biometric identification to enable retrieval of individual-specific health profile information by said wireless device.

21. The method of claim 20, wherein said Visited Operator's IP Services also enables retrieval using connectivity between said PDN GW and its logically connected S-GW by employing an interface using PMIPv6 between a Local Mobility Anchor (LMA) and a Mobile Access Gateway (MAG).

22. The method of claim 16, wherein said network entity also operates compatibly with said wireless access network and at least one IP Network to transform a VPLMN into a rapid healthcare support network, and wherein said request also comprises an attach request; and wherein said VPLMN, if not disallowed by the HPLMN, stores and manages VPLMN-specific Closed Subscriber Group (CSG) subscription information for supporting roaming wireless devices without interactions relying upon an interface between an HSS and an MME for any transfer of data for controlling user access.

23. A method of allocating a wireless channel to enable emergency access from a portable device on behalf of an individual by provisioning a gateway to process a request from said portable device, comprising steps of:
  enabling the initiation of a session to access a database by signaling said portable device to send an authentication key that represents an irreversible transformation of a live raw biometric data sample of said individual as at least part of an authentication assertion;
  processing said authentication assertion automatically using specialized software running compatibly with said database, to associate said at least part of said authentication assertion with a reference biometric, which was stored by said individual during a previous encounter, in anticipation of an event; and
  attaining said key, using said specialized software to permit subsequent communication over at least one wireless channel securely between said portable device and said gateway, wherein said gateway is communicably connectable to said database to retrieve individual-specific health profile information.

24. The method of claim 23, wherein said portable device is also provisioned with an integrated biometric information input unit (BIIU) that resists replacement, and wherein said gateway determines the location of said initiation of a wireless session and the last location of said portable device to ensure session continuity over at least one serving network between said portable device and said database, and wherein a Mobile Management Entity (MME) uses at least an Emergency APN to derive a PDN GW for said portable device so as to provide emergency bearer services.

25. The method of claim 23, wherein said portable device is also provisioned as user equipment (UE) configured for mission critical push to talk service and wherein portable device uses a radio access network to connect with a network node that is an evolved base node (eNodeB), which also enables intermodal communications of said portable device through at least one IP network, by connecting said eNodeB with a gateway that is an EPC Serving Gateway (S-GW).

26. The method of claim 25, wherein said at least one IP network comprises an LTE network with an Evolved Packet Core (EPC) and said EPC supports UE communications over an EUTRAN to transmit data through said gateway of said EPC, wherein said gateway and comprises a Serving Gateway (S-GW) that compatibly permits transmitting intermodal content over the same radio link securely using Orthogonal Frequency-Division Multiplexing (OFDMA).

27. The method of claim 26, wherein said portable device is located in the area of a VPLMN while sending said authentication assertion, and said portable device connects with an eNodeB that uses a radio interface to access the EPC network, wherein said EPC network uses an interface provisioned with Mobile Proxy IPv6 (PMIPv6) between said S-GW operating as a Mobile Access Gateway (MAG) with a PDN-GW operating as a Local Mobility Anchor (LMA), wherein said PMIPv6 interface supports Serving GW relocation due to mobility of said portable device.

28. The method of claim 27, wherein said eNodeB connects said portable device to an MME that connects to said S-GW via a standard interface designed to manage EPS bearers so that said S-GW routes outgoing and incoming IP packets, including at least some of said IP packets that are routed over an interface between said S-GW and its a logically connected non-collocated PDN GW, which interface provides user plane tunneling and tunnel management between Serving GW and said non-collocated PDN GW using a GTP protocol with a PMIP variant, and wherein said S-GW serves as the anchor point for handovers between eNodes of a LTE network, and for handovers for other 3GPP networks, to ensure continuity of each session to support the transmittal of user data over IPv4 and IPv6 channels.

29. The method of claim 28, wherein said MME informs said S-GW of the last known location of the portable device and provides information to enable determination of the time at which the portable device was in that location and said MME also at least governs the signaling for EUTRAN access, which signaling concerns mobility and security for at least said subsequent communications with said portable device, and wherein said collocated PDN GW, which was selected by said MME, exchanges data with a V-PCRF, which uses a standard interface to transmit data with an H-PCRF node, so as to enable said portable device to connect with said database over a PDN by using an Application Function.

30. The method of claim 27, wherein said portable device comprises user equipment (UE) that is located in the coverage territory of said VPLMN, and said UE is connectable with an EPC network operating in the area of said VPLMN, and said EPC network supports interoperability of heterogeneous wireless access networks, and wherein said gateway is a S-GW of said EPC network and interoperates compatibly with at least one PDN GW, which negotiates security parameters, to provide access to at least one external packet data network.

31. The method of claim 23, wherein said gateway is also collocated with a node on an LTE's Evolved Packet Core that compatibly supports at least voice service over LTE to said portable device via a backhaul capability.

32. The method of claim 23, wherein said database comprises a database that is capable of processing data using a scalable and distributed database system that is also extensible to interoperate seamlessly with an external database, upon negotiating security parameters, and wherein said distributed database system also utilizes an extraction mechanism to provide individual specific data.

33. The method of claim 23, also comprising enabling emergency access wherein said MME detects that an active member of a Closed Subscriber Group (CSG) of healthcare support professionals has initiated a session using said portable device; and wherein said database is interoperable with an external service provider, provided said service provider uses certifiable cryptographic techniques of protecting the confidentiality of all individual-specific information under the classifications and security parameters of said specialized software, and said external service provider shares a verifiable credential to confirm it operates in an acceptable role as external service provider wherein said role has been prequalified by said database.

34. The method of claim 23, wherein said specialized software also facilitates the sharing of encrypted data between at least one service model employed by said portable device and at least one service model of an external provider of services to perform biometric recognition securely for rapid personalized health support, so as to transmit to said portable device at least one encrypted data element specific to said individual.

35. A method of specially adapting a network with scalable coverage by using a node of said network for biometric identification, wherein the steps of said node comprises:
establishing a wireless session securely between an authenticating cryptographic module provisioned for biometric identification on behalf of an individual and a wireless device with an integrated BIIU, wherein said module has access to a plurality of stored transformed biometrics including at least one saved during a prior encounter by said individual;
receiving, from said wireless device, identity-binding information, comprising a irreversibly transformed biometric, of said individual; and
associating said identity-binding information uniquely with an identifier of said individual upon biometric authentication.

36. The method of claim 35, further comprising attaining said identifier by executing a query with a database mechanism to extract individual-specific information from a database to produce a result having at least one data object consistently with at least one enforced rule; and wherein said at least one enforced rule excludes from said result any portion of stored health data associated with the individual if said portion of the data does not satisfy all rules applicable to said portion of the data.

37. The method of claim 35, wherein said network comprises a network that is communicably connectible to at least one PDN GW of a LTE network; and wherein said node is also a node that mediates the routing and transfer of said identity-binding information and consists of at least one of the following LTE network components: (a) a S-GW; (b) a MME; (c) an HHS; (d) a Policy Charging and Rule Function (PCRF) node; (e) a PDN GW; (f) an extended PDN (ePDN); (g) an eNodeB; and (h) an Application Function.

38. The network of claim 37, wherein said emergency bearers are assigned upon an emergency attach request, under an emergency services model applied by the VPLMN operator, wherein said model requires that all User Equipment (UEs) at least share an International Mobile Subscriber Identity (IMSI) for authentication.

39. The method of claim 35, wherein said wireless device automatically signals the MME of said serving network, which is backwardly compatible with 2G, 3G, and WCDMA networks, of an attach request to enable using an external packet data network for emergency level network services, so as to enable said serving network to detach any default bearer that is in limited service state by allocating a dedicated emergency bearer to ensure continuous availability of wireless service.

40. The method of claim 35, wherein said node also processes data on the location of said wireless device at the time of session set up and on the last known location of said wireless device, and wherein a MME uses at least a portion of said location data in selecting at least one PDN GW.

41. The method of claim 35, wherein said node also enables associating said identity-binding information uniquely with an identifier of said individual upon remote supervised biometric authentication of said individual by member of a closed subscriber group (CSG) of first responders to ensure emergency bearers are assigned because said wireless device of a CSG also transmits at least a CSG code with said identity-binding information which CSG code signifies an emergency attach request.

42. The method of claim 35, wherein said network also interprets data received from said wireless device as an attach request for emergency service support and to connect through a visited public land mobile network (VPLMN); and said attach request is transmitted by said wireless device from within the service area of said VPLMN, and wherein said emergency service support is a local service of said VPLMN, which does not requires subscriber information from the HSS in the home public land mobile network (HPLMN) of said wireless device.

43. The method of claim 35, wherein said wireless device is a roaming device that when activated automatically emits data comprising an attach request to establish emergency service support and wherein a responsive attach reply is sent to said wireless device.

44. The method of claim 43, wherein said attach request is received by an MME within a service area of a VPLMN, and said MME selects a PDN-GW associated with an Emergency APN that supports PDN type IPv4 and PDN type IPv6, and said PDN-GW, for a positive attach reply, also ascribes IP address and prefix allocation data to establish connectivity for emergency bearer services by assigning a priority value for emergency services, compatibly with the policy control and charging (PCC) of said VPLMN.

45. The network of claim 43, wherein said PCC instructions are retrieved from a module that governs PCC for said selected PDN GW, which is communicable connectable to said node, wherein said module is accessible from said selected PDN GW in said VPLMN via a visited PCRF (V-PCRF) that enables control using the Application Function (AF) of said visited operator.

46. A method of constraining access to individual-specific information in a database in accordance with pre-defined constraints, comprising the steps of:
receiving a remote request to identify an individual by processing a query transmitted with said request by utilizing said database configured to store individual-specific data;
verifying that said request was sent over at least one wireless channel securely from a wireless device with an authorization code;
validating the query based on a transfer by said wireless device of compatible transformed biometric data using a biometric algorithm;
executing said query to determine that at least part of said transformed biometric data can be resolved into a key by comparing a biometric reference stored during a previous encounter; and
producing a key by said database to identify said individual, absent a violation of any rule of said database.

47. The method of constraining access in claim 46, wherein said database comprises a database module that is activated after producing said key to limit post-processing retrieval of individual-specific data corresponding to said key from said database until said module has executed all post-processing rules applicable to the result of said query, for selectively blocking transmission of a data element of the results if any of the post-processing rules applied to said data element of said results are not passed, and for otherwise enabling transmission of said data element of said results.

48. The method of constraining access in claim 46, wherein said at least one wireless channel is communicably connectable to a gateway, comprised of an extended Packet Data Network (ePDN) for untrusted communication over a Non-3GPP network, and said ePDN participates with at least one other core component of an LTE EPC network to ensure local communications route locally and to provide continuous mobile security comprising at least confidentiality policy control and enforcement for roaming.

49. The method of constraining access in claim 46, wherein said database also operates as a distributed database, compatibly with an ePDN, to serve as a virtual privacy officer that applies at least one pre-processing rule to determine whether to permit the packet connection requested via an untrusted non-3GPP network to said ePDN; and said ePDN verifies security via an AAA server to authenticate said wireless device, and if authenticated, allocate a channel using IPSec tunneling.

50. The method of constraining access in claim 46, wherein said at least one wireless channel is communicably connectable to a gateway that enables associating said key with individual specific results upon remote unsupervised biometric authentication by connecting with said database via a session of a trusted network within the area of a VPLMN during roaming, and wherein a required authentication of said wireless device to said trusted network, if any, is enforced in accordance with the policy of said trusted network.

51. The method of constraining access in claim 46, wherein said at least one wireless channel is communicably connectable to a gateway that comprises an ePDG that also selectively enables an untrusted session to associate said key with individual specific results upon remote unsupervised biometric authentication by connecting said ePDG via a non-3GPP network with an access server that constrains access to said database under at least one confidentiality rule, wherein said ePDG uses IPSec tunneling to transmit data selectively between said access server and said wireless device.

52. A computer-implemented method of information retrieval using wireless connectivity and biometric identification, comprising the steps of:
receiving a remote request to identify an individual, from a wireless device employed on the behalf of said individual, over at least one wireless network securely;
processing said remote request by a processor that is communicably connectable to a database that uses at least one biometric modality previously tested to enable reliable identification within a predetermined tolerance; and
comparing irreversibly transformed biometric data of an individual, transmitted from said wireless device, with stored transformed biometric data using said at least one biometric modality to extract output from said database solely associated with said individual to enable information retrieval for rapid healthcare service.

53. The method of claim 52, wherein said processor, said database, and said at least one wireless network are always on, and said at least one wireless network supports vehicular mobility over 2G, 3G, and WCDMA networks with backward compatibility and roaming.

54. The method of claim 53 wherein said wireless device while roaming in an area served by a VPLMN sends a remote request that comprises an attach request to use intra-PLMN access via a visited operator's IP services to a PDN, and at least two MMEs support roaming by transferring information for intra-VPLMN and inter-VPLMN control-plane transfers.

55. The method of claim 54, wherein said wireless device attains access over a General Packet Radio Service (GPRS) while roaming from a GPRS Support Network (GSN) within the area of said VPLMN, by initiating a session a Serving GPRS Support Network (SGSN) that interfaces with S-GW of an LTE network for control and mobility support between a GPRS Core and the 3GPP anchor function of the Serving GW, and wherein if no direct tunnel established, said interface also provides the user plane tunneling, and wherein an MME of said LTE network uses a standard interface with said SGSN to enables user and bearer information exchange for inter 3GPP access network mobility in idle and active state.

56. The method of claim 52, wherein said wireless device comprises a roaming wireless device that initiates a session via a Universal Terrestrial Radio Access Network (UTRAN) that connect with an S-GW of an LTE Network within a service area of a VPLMN, by relying upon a standard interface that is used for connectivity by establishing a direct tunnel using a GPRS Tunneling Protocol (GTP-U) protocol, and wherein said S-GW also transmits user plane data to a selected PDN GW that is communicable connectible the V-PCRF node, wherein said PDG GW permits said wireless device to connect to said database via the visited operators IP services.

57. The method of claim 52, wherein said database also comprises a database that is accessible by said wireless device, while roaming, over a packet data network by using an LTE combined functionalities to facilitate communications by using a distinct APN for urgent healthcare support communications and activating a packet data protocol (PDP) context to ensure access to at least one to the following group: (i) an operator external public packet data network; (ii) an operator external private packet data network; (iii) an intra operator packet data network; (iv) an intra operate packet data network for provision of IMS Emergency services.

58. The method of claim 52, wherein said wireless device also comprises a roaming wireless device that accesses said database by using an LTE roaming architecture for local breakout with visited operator's IP services, wherein the selected PDN GW is communicable connectible the V-PCRF node, as needed, and the LTE network uses an Emergency APN to allocate facilities for IMS emergency services.

59. The method of claim 52, wherein said wireless device also comprises a roaming wireless device that accesses said database by using an Emergency APN so that the LTE network allocates emergency bearer services.

60. The method of claim 52, wherein said wireless device also comprises a roaming wireless device that accesses said database by using an LTE roaming architecture for local breakout with visited operator's IP services.

61. The method of claim 60, wherein said method further comprises using components of said HPLMN that are configured to store and manage VPLMN-specific CSG subscription information for roaming wireless devices without interaction with HSS associated with said wireless device, to provide access to at least one packet data network.

62. The method of claim 52, wherein said wireless device also comprises a roaming wireless device with mobility at vehicular speeds, and said at least one wireless network provides access to an LTE network, which selects a PDN GW, said PDN GW is communicable connectible a V-PCRF node, as needed, and said LTE network process an Emergency APN with a URL to activate a packet data protocol PDP context using at least an IP address, IMSI, and tunnel endpoint data to support connectivity to said database accessible via a PDN.

63. The method of claim 52, wherein said wireless device also comprises a roaming wireless device with mobility at vehicular speeds, and said at least one wireless network provides access to an LTE network operating within the territory of a VPLMN, which LTE network selects a PDN GW, and said LTE network processes an SIP and URL, to activate a packet data protocol PDP context based upon at least an IP address and an IMSI, to support a session to retrieve data from said database.

64. The method of claim 52 wherein said at least one wireless network also supports roaming and mobility at vehicular speeds in cooperation with an LTE network operating in any adjacent VPLMN area, and said wireless device invokes a visited operator's IP services that use the Application Function of said visited operator and to connect with said database via a PDN, wherein said control is governed by a V-PCRF using control-plane transfers that support an IMS emergency session.

65. The method of claim 52, wherein said wireless network supports data communications that support roaming and mobility at vehicular speeds while compatibly handling push-to-talk voice services over backhaul services by using radio resource management to enable at intermodal communications with said one wireless device over at the same radio link.

66. The method of claim 52, wherein said method also comprises transmitting an emergency service identifier to an SIP URL for an emergency services routing proxy (ESRP) to support urgent healthcare communications, by using an internal database that contains the service regions of each ESRP.

67. The method of claim 52, wherein said method also comprises invoking, by an network entity on the serving network communicably connectable to said wireless device, a Proxy Call Session Control Function (CSCF) to attain an Emergency CSCF (E-CSCF), with a Local Retrieval Function (LRF).

68. The method of claim 52, wherein said method also comprises transmitting at least a portion of said irreversibly transformed biometric data over a gateway by default integrates means for biometric identification securely.

69. The method of claim 68, wherein said gateway operates as part of a plurality of distributed gateways, and wherein said gateway is communicably connectable to a a PCRF node, in the service area where said wireless device originates communication, which PCRF node selectively constrains access to emergency bearer services at least under at least one rule.

70. The method of claim 52, wherein said method also comprises transmitting at least a portion of said irreversibly transformed biometric data over a database that is a distributed database, communicably connectable to said system, wherein said distributed database that stores transformed biometric data used for biometric recognition in case of an uncertain health event.

71. The method of claim 52, wherein said method also comprises transmitting at least a portion of said irreversibly transformed biometric data to a central registry that selectively matches (i) a data code, transmitted from said wireless device, that identifies an algorithm used to create an irreversibly transformed biometric data of an individual with (ii) a compatible biometric algorithm among a plurality of biometric algorithms that facilitate comparisons with stored transformed biometric data used for identification to mediate for service differentiation among different biometric identification services with different QoS parameters.

72. The method of claim 52, wherein said method also comprises transmitting data over at least the user plane of the serving network for rapid healthcare support to accessibly connect with IMS-accessible resources via at least one of the following: (a) common IMS access; (b) Emergency IMS access; (c) an operator packet data network; (d) an intra operator packet data network for provision of IMS services; and (e) an IP network access that is also communicably connectable to a Digital Mobile Radio (DMR) network.

* * * * *